(12) United States Patent
Akai et al.

(10) Patent No.: US 10,807,372 B2
(45) Date of Patent: Oct. 20, 2020

(54) LIQUID DROPLET DISCHARGING UNIT, LIQUID DROPLET FORMING DEVICE, AND STIRRING DEVICE

(71) Applicants: Takeshi Akai, Kanagawa (JP); Hiroshi Fujie, Kanagawa (JP); Keisuke Sugiyama, Kanagawa (JP); Daisuke Takagi, Kanagawa (JP); Hiroki Somada, Shizuoka (JP); Manabu Yamanaka, Kanagawa (JP)

(72) Inventors: Takeshi Akai, Kanagawa (JP); Hiroshi Fujie, Kanagawa (JP); Keisuke Sugiyama, Kanagawa (JP); Daisuke Takagi, Kanagawa (JP); Hiroki Somada, Shizuoka (JP); Manabu Yamanaka, Kanagawa (JP)

(73) Assignee: Ricoh Company, Ltd., Tokyo (JP)

(*) Notice: Subject to any disclaimer, the term of this patent is extended or adjusted under 35 U.S.C. 154(b) by 0 days.

(21) Appl. No.: 16/238,570

(22) Filed: Jan. 3, 2019

(65) Prior Publication Data
US 2019/0232661 A1   Aug. 1, 2019

(30) Foreign Application Priority Data

Jan. 29, 2018  (JP) ................................. 2018-012354
Jan. 29, 2018  (JP) ................................. 2018-012358
(Continued)

(51) Int. Cl.
*B41J 2/175*   (2006.01)
*B41J 2/165*   (2006.01)
(Continued)

(52) U.S. Cl.
CPC ......... *B41J 2/1652* (2013.01); *B01F 11/0074* (2013.01); *B05B 15/20* (2018.02);
(Continued)

(58) Field of Classification Search
CPC . B41J 2/175; B41J 2/17596; B41J 2/18; B41J 2/195; B41J 2/1652; B05B 15/20; B01F 11/0074
See application file for complete search history.

(56) References Cited

U.S. PATENT DOCUMENTS

2007/0041874 A1   2/2007 Sukavaneshvar et al.
2007/0183935 A1   8/2007 Clemmens et al.
(Continued)

FOREIGN PATENT DOCUMENTS

EP   3 042 772 A1   7/2016
EP   3 196 288 A1   7/2017
(Continued)

OTHER PUBLICATIONS

Extended European Search Report dated Jun. 14, 2019 in European Patent Application No. 19151850.5, 11 pages.

*Primary Examiner* — Lamson D Nguyen
(74) *Attorney, Agent, or Firm* — Oblon, McClelland, Maier & Neustadt, L.L.P.

(57) ABSTRACT

Provided is a liquid droplet discharging unit including a liquid droplet discharging port, a liquid retaining section including the liquid droplet discharging port, two tubes disposed in communication with the liquid retaining section, and first and second liquid sucking/ejecting members coupled to the two tubes respectively, wherein while the first liquid sucking/ejecting member is in a sucking or ejecting state, the second liquid sucking/ejecting member is in a non-sucking or non-ejecting state correspondingly.

18 Claims, 46 Drawing Sheets

(30) Foreign Application Priority Data

| Mar. 15, 2018 | (JP) | 2018-047526 |
| Mar. 15, 2018 | (JP) | 2018-047527 |
| Mar. 15, 2018 | (JP) | 2018-047529 |
| Mar. 16, 2018 | (JP) | 2018-049803 |

(51) Int. Cl.

| *B41J 2/18* | (2006.01) |
| *B41J 2/195* | (2006.01) |
| *C12M 1/00* | (2006.01) |
| *B05B 15/20* | (2018.01) |
| *B01F 11/00* | (2006.01) |
| *B41J 2/14* | (2006.01) |
| *C12M 1/26* | (2006.01) |

(52) U.S. Cl.
CPC .......... *B41J 2/175* (2013.01); *B41J 2/17596* (2013.01); *B41J 2/18* (2013.01); *B41J 2/195* (2013.01); *C12M 1/00* (2013.01); *B41J 2002/14435* (2013.01); *B41J 2202/15* (2013.01); *C12M 33/00* (2013.01)

(56) References Cited

U.S. PATENT DOCUMENTS

| 2007/0269355 A1 | 11/2007 | Malmqvist |
| 2009/0162885 A1 | 6/2009 | Sukavaneshvar et al. |
| 2010/0167384 A1 | 7/2010 | Clemmens et al. |
| 2011/0102519 A1 | 5/2011 | Koseki |
| 2012/0064597 A1 | 3/2012 | Clemmens et al. |
| 2012/0140003 A1 | 6/2012 | Szusdziara et al. |
| 2012/0194619 A1 | 8/2012 | Smith et al. |
| 2012/0200619 A1 | 8/2012 | Bibl |
| 2012/0286064 A1 | 11/2012 | Chang et al. |
| 2013/0143307 A1 | 6/2013 | Nozaki et al. |
| 2013/0222491 A1 | 8/2013 | Nanjo et al. |
| 2013/0278688 A1 | 10/2013 | Bibl |
| 2014/0002551 A1 | 1/2014 | Smith et al. |
| 2014/0354717 A1 | 12/2014 | Bibl |
| 2015/0314609 A1 | 11/2015 | Bibl |
| 2016/0175834 A1 | 6/2016 | Seo et al. |
| 2016/0176191 A1 | 6/2016 | Kuramochi et al. |
| 2017/0203567 A1 | 7/2017 | Yoshida et al. |
| 2018/0290454 A1 | 10/2018 | Kammerzell et al. |
| 2018/0340880 A1 | 11/2018 | Matsumoto et al. |

FOREIGN PATENT DOCUMENTS

| JP | 08-276599 | 10/1996 |
| JP | 2008-213281 | 9/2008 |
| JP | 2011-093200 | 5/2011 |
| JP | 2011-121344 | 6/2011 |
| JP | 2012-152939 | 8/2012 |
| JP | 2013-199112 | 10/2013 |
| JP | 2014-094485 | 5/2014 |
| JP | 2016-116489 | 6/2016 |
| JP | 2016-203157 | 12/2016 |
| JP | 2017-077197 | 4/2017 |
| JP | 2018-146447 | 9/2018 |
| WO | WO 2008/108245 A1 | 9/2008 |
| WO | WO2016/042722 A1 | 3/2016 |
| WO | WO 2017/071756 A1 | 5/2017 |
| WO | WO 2017/130707 A1 | 8/2017 |

ΔT1, ΔT1': Delay time due to backlash of first sucking/ejecting member

ΔT1, ΔT1': Delay time due to backlash of first sucking/ejecting member
ΔT2, ΔT2': Delay time due to backlash of second sucking/ejecting member

US 10,807,372 B2

LIQUID DROPLET DISCHARGING UNIT, LIQUID DROPLET FORMING DEVICE, AND STIRRING DEVICE

CROSS-REFERENCE TO RELATED APPLICATIONS

The present application claims priority under 35 U.S.C. § 119 to Japanese Patent Application No. 2018-012354 filed Jan. 29, 2018, Japanese Patent Application No. 2018-012358 filed Jan. 29, 2018, Japanese Patent Application No. 2018-047526 filed Mar. 15, 2018, Japanese Patent Application No. 2018-047527 filed Mar. 15, 2018, Japanese Patent Application No. 2018-047529 filed Mar. 15, 2018, and Japanese Patent Application No. 2018-049803 filed Mar. 16, 2018. The contents of which are incorporated herein by reference in their entirety.

BACKGROUND OF THE INVENTION

Field of the Invention

The present disclosure relates to a liquid droplet discharging unit, a liquid droplet forming device, and a stirring device.

Description of the Related Art

Hitherto, there has been known a technique in which a liquid obtained by dispersing cells in a solvent is discharged with an inkjet head in the form of liquid droplets, to dispense the cells by a predetermined number.

However, as compared with the nanoscale particle diameter of pigment inks used in existing inkjet methods, cells in cell dispensing with existing inkjet heads have a particle diameter of from some micrometers through some tens of micrometers. Due to this greater particle diameter, there has been a problem that the cells undergo sedimentation and the cell concentration distribution in the tank changes over time, to degrade discharging stability.

Hence, for example, there has been proposed a technique in which two ink tanks, a flow path linking the two ink tanks, and an inkjet head linked to the flow path between the two ink tanks are provided, and different pressures are applied to these ink tanks respectively, to generate an ink flow and stir the ink in the flow path (for example, see Japanese Unexamined Patent Application Publication No. 2008-213281).

Specifically, as illustrated in FIG. 1, at a pressure from a first pump 13, an ink flows from a first ink tank 10 into an inkjet head 30 through a first flow path 15, while at the same time, at a pressure from a second pump 23 different from the pressure from the first pump, the ink flows from the inkjet head 30 into a second ink tank 20 through a second flow path 25. This makes it possible to generate an ink flow throughout the entire region in which the ink is present, and hence to prevent sedimentation of solid components contained in the ink.

SUMMARY OF THE INVENTION

A liquid droplet discharging unit of the present disclosure includes a liquid droplet discharging port, a liquid retaining section including the liquid droplet discharging port, two tubes disposed in communication with the liquid retaining section, and first and second liquid sucking/ejecting members coupled to the two tubes respectively. While the first liquid sucking/ejecting member is in a sucking or ejecting state, the second liquid sucking/ejecting member is in a non-sucking or non-ejecting state correspondingly.

Figure 1:
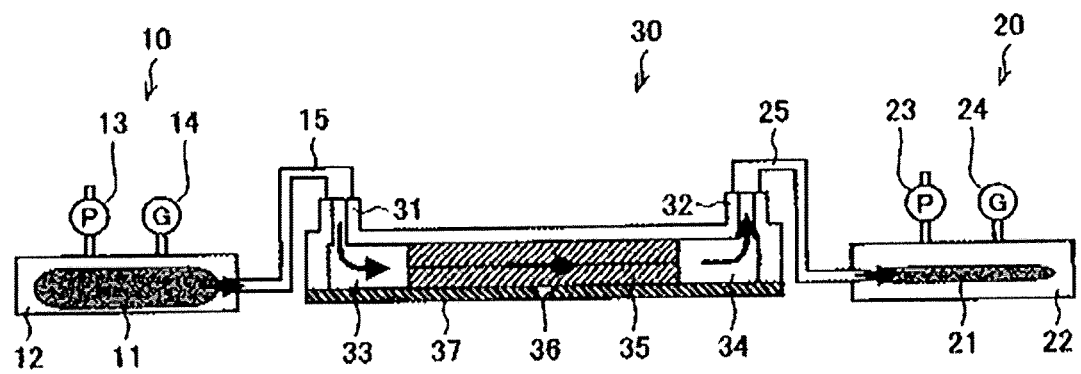
FIG. 1 is a diagram illustrating an example of an existing liquid droplet forming device.

DESCRIPTION OF THE EMBODIMENTS (Liquid Droplet Discharging Unit)

A liquid droplet discharging unit of the present disclosure includes a liquid droplet discharging port, a liquid retaining section including the liquid droplet discharging port, two tubes disposed in communication with the liquid retaining section, and first and second liquid sucking/ejecting members coupled to the two tubes respectively. While the first liquid sucking/ejecting member is in a sucking or ejecting state, the second liquid sucking/ejecting member is in a non-sucking or non-ejecting state correspondingly. The liquid droplet discharging unit further includes other members as needed.

The liquid droplet discharging unit of the present disclosure is based on the following finding. According to existing techniques, a stirring flow can be generated only in one direction, namely a perpendicular direction with respect to a nozzle plate. Therefore, the problem that the particle concentration distribution in the tank changes over time due to stagnation of particles at, for example, the corners of the tank cannot be overcome.

The liquid droplet discharging unit of the present disclosure is also based on the following finding. According to existing sedimentation preventing mechanisms based on an ink flow, an ink flow is less likely to be generated at inkjet head corners at which solid components are most likely to accumulate. Therefore, due to the accumulation of solid components at the corners, it is feared that the ink particle concentration at other than the corners may be reduced over time.

The present disclosure has an object to provide a liquid droplet discharging unit capable of maintaining a particle concentration of a particle-containing liquid constant in a liquid retaining section of the liquid droplet discharging unit.

The present disclosure can provide a liquid droplet discharging unit capable of maintaining a particle concentration of a particle-containing liquid constant in a liquid retaining section of the liquid droplet discharging unit.

The present disclosure includes a liquid droplet discharging port, a liquid retaining section including the liquid droplet discharging port, two tubes disposed in communication with the liquid retaining section, and first and second liquid sucking/ejecting members coupled to the two tubes respectively. Therefore, by causing a liquid from the two tubes to flow along a nozzle plate and a wall surface of the liquid retaining section, it is possible to generate an ascending flow in the liquid retaining section and disperse the particles accumulated on the bottom of the liquid retaining section.

Further, by continuously generating stirring flows in a plurality of directions in the liquid in the liquid retaining section, it is possible to disperse the particles in the liquid and maintain the particle concentration of the particle-containing liquid in the liquid retaining section constant over time.

<Liquid Retaining Section>

It is preferable that the liquid retaining section include: a nozzle plate including a liquid droplet discharging port; and a vibration member, and it is further preferable that the liquid retaining section include other members as needed.

When the liquid droplet discharging unit is an open head, it is preferable that the liquid retaining section include an atmospherically exposed portion at the top. The position of the atmospherically exposed portion is not limited to the top. Bubbles mixed in the liquid can be evacuated through the atmospherically exposed portion.

The shape, size, material, and structure of the liquid retaining section are not particularly limited and may be appropriately selected depending on the intended purpose.

Examples of the material of the liquid retaining section include stainless steel, nickel, and aluminum, and silicon dioxide, alumina, and zirconia.

Among these materials, it is preferable to use a material having a low adhesiveness with cells and proteins, when cells and proteins are used as particles.

Generally, adhesiveness of cells is said to be dependent on the contact angle of the material with respect to water. When the material has a high hydrophilicity or a high hydrophobicity, the material has a low adhesiveness with cells. As the material having a high hydrophilicity, various metal materials and ceramics (metal oxides) can be used. As the material having a high hydrophobicity, for example, fluororesins can be used.

In addition, it is conceivable to reduce cell adhesiveness by coating the surface of the material. For example, it is possible to coat the surface of the material with the metal or metal oxide materials described above, or coat the surface of the material with a synthetic phospholipid polymer mimicking a cellular membrane (e.g., LIPIDURE available from NOF Corporation).

—Nozzle Plate—

The nozzle plate is a member in which a liquid droplet discharging port (nozzle) is formed, and that is configured to discharge a liquid retained in the liquid retaining section through the liquid droplet discharging port in the form of a liquid droplet by means of vibration of an amplitude motion of the nozzle plate.

When the liquid droplet discharging unit is an open head, the nozzle plate is secured at the lower end of the liquid retaining section.

When the liquid droplet discharging unit is a closed head, the nozzle plate is secured at the upper end of the liquid retaining section.

The liquid retained in the liquid retaining section is discharged in the form of a liquid droplet through the liquid droplet discharging port, which is a through hole, by means of vibration of the nozzle plate.

The planar shape, size, material, and structure of the nozzle plate are not particularly limited and may be appropriately selected depending on the intended purpose.

Examples of the planar shape of the nozzle plate include a circular shape, an elliptic shape, a rectangular shape, a square shape, and a rhomboidal shape.

If the material of the nozzle plate is extremely flexible, the nozzle plate easily undergo vibration and is not easily able to stop vibration immediately when there is no need for discharging. Therefore, it is preferable to use a material having a certain degree of hardness. Examples of the material of the nozzle plate include metals, ceramics, and polymeric materials. Specific examples of the material of the nozzle plate include stainless steel, nickel, aluminum, silicon dioxide, alumina, and zirconia. Among these materials, it is preferable to use a material having a low adhesiveness with cells and proteins, when cells and proteins are used as particles, like the liquid retaining section.

—Liquid Droplet Discharging Port—

As regards the liquid droplet discharging port, for example, the number of lines in which liquid droplet discharging ports are arranged, the formation in which liquid droplet discharging ports are arranged, the interval (pitch), the opening shape of the liquid droplet discharging port, and the size of the opening are not particularly limited and may be appropriately selected depending on the intended purpose.

The number of lines in which liquid droplet discharging ports are arranged is not particularly limited and may be appropriately selected depending on the intended purpose. It is preferable that the one or more lines, or more preferably, one or more lines but four or less lines of liquid droplet discharging ports be arranged along a longer direction of the discharging surface of the liquid droplet discharging unit. By arranging one or more lines of liquid droplet discharging ports, it is possible to increase the number of liquid droplets to be discharged per unit time and to discharge different kinds of particles (for example, different kinds of cells) at a time by using different lines.

The number of liquid droplet discharging ports per line is not particularly limited, may be appropriately selected depending on the intended purpose, and is preferably 2 or more but 100 or less, more preferably 2 or more but 50 or less, and yet more preferably 2 or more but 12 or less. When the number of liquid droplet discharging ports per line is 2 or more but 100 or less, it is possible to provide a liquid droplet forming device capable of increasing the number of liquid droplets to be discharged per unit time and having a high productivity.

The formation in which liquid droplet discharging ports are arranged is not particularly limited, may be appropriately selected depending on the intended purpose, and may be a regular arrangement (for example, a staggered arrangement) or an irregular arrangement.

When a plurality of lines of liquid droplet discharging ports are arranged, it is preferable to provide a partitioning member between the lines in order to make it possible to prevent interference between liquid droplets to be discharged from adjoining liquid droplet discharging ports and to improve a detection sensitivity of particles. Examples of the partitioning member include a partitioning plate.

It is preferable that the lines of liquid droplet discharging ports be arranged side by side at equal intervals. The interval (pitch) P, which is the shortest distance between the centers of adjoining liquid droplet discharging ports is not particularly limited, may be appropriately selected depending on the intended purpose, and is preferably from 50 micrometers or greater but 1,000 micrometers or less.

The opening shape of the liquid droplet discharging port is not particularly limited and may be appropriately selected depending on the intended purpose. Examples of the opening shape of the liquid droplet discharging port include a circular shape, an elliptic shape, and a quadrangular shape.

The average diameter of the liquid droplet discharging ports is not particularly limited, may be appropriately selected depending on the intended purpose, and is preferably twice or more greater than the size of particles in order to avoid clogging of particles in the liquid droplet discharging ports.

When the particle is, for example, an animal cell, particularly, a human cell, the average diameter of the liquid droplet discharging ports is preferably 10 micrometers or greater but 100 micrometers or less in conformity with the cell used, because a human cell typically has a size of about 5 micrometers or greater but 50 micrometers or less.

On the other hand, when a liquid droplet is extremely large, it is difficult to achieve an object of forming a minute liquid droplet. Therefore, the average diameter of the liquid droplet discharging ports is preferably 200 micrometers or less. Hence, the average diameter of the liquid droplet discharging ports is more preferably 10 micrometers or greater but 200 micrometers or less.

—Vibration Member—

The vibration member is a member configured to vibrate the nozzle plate to cause liquid droplets to be discharged through the liquid droplet discharging ports (nozzles).

When the liquid droplet discharging unit is an open head, the vibration member is formed on the lower surface side of the nozzle plate.

When the liquid droplet discharging unit is a closed head, the vibration member is formed on the upper surface side of the nozzle plate.

The shape, size, material, and structure of the vibration member are not particularly limited and may be appropriately selected depending on the intended purpose.

The shape of the vibration member is not particularly limited and may be appropriately designed to match the shape of the nozzle plate. For example, when the planer shape of the nozzle plate is a circular shape, it is preferable to provide a vibration member having a circular shape in the case of a closed head. It is preferable to form a vibration member having an annular (ring-like) planar shape around a liquid droplet discharging port in the case of an open head.

As the vibration member, a piezoelectric element is suitably used.

The piezoelectric element may have a structure obtained by providing the upper surface and the lower surface of a piezoelectric material with electrodes across which a voltage is to be applied. In this case, when a driving unit applies a voltage across the upper and lower electrodes of the piezoelectric element, a compressive stress is applied in the horizontal direction in the surface of a film, making it possible for the nozzle plate to vibrate in the upward-downward direction of the surface of the film.

The piezoelectric material is not particularly limited and may be appropriately selected depending on the intended purpose. Examples of the piezoelectric material include lead zirconate titanate (PZT), bismuth iron oxide, metal niobate, barium titanate, or materials obtained by adding metals or different oxides to these materials. Among these piezoelectric material, lead zirconate titanate (PZT) is preferable.

The liquid retaining section is configured to retain a particle-containing liquid, which is discharged through the liquid droplet discharging ports of the nozzle plate in the form of liquid droplets.

<Liquid Droplet>

It is preferable that a liquid droplet contain a particle.

The number of particles contained in a liquid droplet is preferably 1 or more and more preferably 1 or more but 5 or less.

The diameter of a liquid droplet is not particularly limited and may be appropriately selected depending on the intended purpose, and is preferably 25 micrometers or greater but 150 micrometers or less. When the diameter of a liquid droplet is 25 micrometers or greater, a particle to be contained in the liquid droplet has an appropriate diameter, making it possible to use many kinds of particles. When the diameter of a liquid droplet is 150 micrometers or less, liquid droplet discharging is stable.

When it is assumed that the diameter of a liquid droplet is R and the diameter of a particle is r, it is preferable that $R>3r$ be satisfied. When $R>3r$ is satisfied, the relationship between the diameter of a particle and the diameter of a liquid droplet is appropriate, and a particle is not to be influenced by the edge of the liquid droplet. Hence, a particle number counting accuracy is improved.

The liquid amount in a liquid droplet is not particularly limited, may be appropriately selected depending on the intended purpose, and is preferably 1,000 pL or lower and more preferably 100 pL or lower.

The liquid amount in a liquid droplet can be measured by, for example, a method of obtaining the size of a liquid droplet based on a liquid droplet image and calculating the liquid amount.

Examples of the particle to be contained in a liquid droplet include metallic particles, inorganic particles, and cells. Among these particles, cells are preferable.

Cells are not particularly limited and may be appropriately selected depending on the intended purpose. All kinds of cells can be used regardless of whether the cells are eukaryotic cells, prokaryotic cells, multicellular organism cells, and unicellular organism cells. One of these kinds of cells may be used alone or two or more of these kinds of cells may be used in combination.

The eukaryotic cells are not particularly limited and may be appropriately selected depending on the intended purpose. Examples of the eukaryotic cells include animal cells, insect cells, plant cells, fungi, algae, and protozoans. One of these kinds of eukaryotic cells may be used alone or two or more of these kinds of eukaryotic cells may be used in combination. Among these eukaryotic cells, animal cells and fungi are preferable, and cells derived from humans are more preferable.

Adherent cells may be primary cells directly taken from tissues or organs, or may be cells obtained by passaging primary cells directly taken from tissues or organs a few times. Adherent cells may be appropriately selected depending on the intended purpose. Examples of adherent cells include differentiated cells and undifferentiated cells.

Differentiated cells are not particularly limited and may be appropriately selected depending on the intended purpose. Examples of differentiated cells include: hepatocytes, which are parenchymal cells of a liver; stellate cells; Kupffer cells; endothelial cells such as vascular endothelial cells, sinusoidal endothelial cells, and corneal endothelial cells; fibroblasts; osteoblasts; osteoclasts; periodontal ligament-derived cells; epidermal cells such as epidermal keratinocytes; epithelial cells such as tracheal epithelial cells, intestinal epithelial cells, cervical epithelial cells, and corneal epithelial cells; mammary glandular cells; pericytes; muscle cells such as smooth muscle cells and myocardial cells; renal cells; pancreatic islet cells; nerve cells such as peripheral nerve cells and optic nerve cells; chondrocytes; and bone cells.

Undifferentiated cells are not particularly limited and may be appropriately selected depending on the intended purpose. Examples of undifferentiated cells include: pluripotent stem cells such as embryonic stem cells, which are undifferentiated cells, and mesenchymal stem cells having pluripotency; unipotent stem cells such as vascular endothelial progenitor cells having unipotency; and iPS cells.

Fungi are not particularly limited and may be appropriately selected depending on the intended purpose. Examples of fungi include molds and yeast fungi. One of these kinds of fungi may be used alone or two or more of these kinds of fungi may be used in combination. Among these kinds of fungi, yeast fungi are preferable because the cell cycles are adjustable and monoploids can be used.

The cell cycle means a cell proliferation process in which cells undergo cell division and cells (daughter cells) generated by the cell division become cells (mother cells) that undergo another cell division to generate new daughter cells.

Yeast fungi are not particularly limited and may be appropriately selected depending on the intended purpose. For example, Bar1-deficient yeasts with enhanced sensitivity to a pheromone (sex hormone) that controls the cell cycle at a G1 phase are preferable. When yeast fungi are Bart-deficient yeasts, the abundance ratio of yeast fungi with uncontrolled cell cycles can be reduced. This makes it possible to, for example, prevent a specific nucleic acid from increasing in number in the cells contained in a container.

The prokaryotic cells are not particularly limited and may be appropriately selected depending on the intended purpose. Examples of the prokaryotic cells include eubacteria and archaea. One of these kinds of prokaryotic cells may be used alone or two or more of these kinds of prokaryotic cells may be used in combination.

As the cells, dead cells are preferable. With dead cells, it is possible to prevent occurrence of cell division after fractionation.

As the cells, cells that can emit light upon reception of light are preferable. With cells that can emit light upon reception of light, it is possible to land the cells on a landing target while having a highly accurate control on the number of cells.

Reception of light means receiving of light.

An optical sensor means a passive sensor configured to collect, with a lens, any light in the range from visible light rays visible by human eyes to near infrared rays, short-wavelength infrared rays, and thermal infrared rays that have longer wavelengths than the visible light rays, to obtain, for example, shapes of target cells in the form of image data.

—Cells that can Emit Light Upon Reception of Light—

The cells that can emit light upon reception of light are not particularly limited and may be appropriately selected depending on the intended purpose so long as the cells can emit light upon reception of light. Examples of the cells include cells stained with a fluorescent dye, cells expressing a fluorescent protein, and cells labeled with a fluorescent-labeled antibody.

A cellular site stained with a fluorescent dye, expressing a fluorescent protein, or labeled with a fluorescent-labeled antibody is not particularly limited. Examples of the cellular site include a whole cell, a cell nucleus, and a cellular membrane.

—Fluorescent Dye—

Examples of the fluorescent dye include fluoresceins, azo dyes, rhodamines, coumarins, pyrenes, cyanines. One of these fluorescent dyes may be used alone or two or more of these fluorescent dyes may be used in combination. Among these fluorescent dyes, fluoresceins, azo dyes, and rhodamines are preferable, and eosin, Evans blue, trypan blue, rhodamine 6G, rhodamine B, and rhodamine 123 are more preferable.

As the fluorescent dye, a commercially available product may be used. Examples of the commercially available product include product name: EOSIN Y (available from Wako Pure Chemical Industries, Ltd.), product name: EVANS BLUE (available from Wako Pure Chemical Industries, Ltd.), product name: TRYPAN BLUE (available from Wako Pure Chemical Industries, Ltd.), product name: RHODAMINE 6G (available from Wako Pure Chemical Industries, Ltd.), product name: RHODAMINE B (available from Wako Pure Chemical Industries, Ltd.), and product name: RHODAMINE 123 (available from Wako Pure Chemical Industries, Ltd.).

—Fluorescent Protein—

Examples of the fluorescent protein include Sirius, EBFP, ECFP, mTurquoise, TagCFP, AmCyan, mTFP1, Midoriishi-Cyan, CFP, TurboGFP, AcGFP, TagGFP, Azami-Green, ZsGreen, EmGFP, EGFP, GFP2, HyPer, TagYFP, EYFP, Venus, YFP, PhiYFP, PhiYFP-m, TurboYFP, ZsYellow, mBanana, KusabiraOrange, mOrange, TurboRFP, DsRed-Express, DsRed2, TagRFP, DsRed-Monomer, AsRed2, mStrawberry, TurboFP602, mRFP1, JRed, KillerRed, mCherry, mPlum, PS-CFP, Dendra2, Kaede, EosFP, and KikumeGR. One of these fluorescent proteins may be used alone or two or more of these fluorescent proteins may be used in combination.

—Fluorescent-Labeled Antibody—

The fluorescent-labeled antibody is not particularly limited and may be appropriately selected depending on the intended purpose so long as the fluorescent-labeled antibody is fluorescent-labeled. Examples of the fluorescent-labeled antibody include CD4-FITC and CD8-PE. One of these fluorescent-labeled antibodies may be used alone or two or more of these fluorescent-labeled antibodies may be used in combination.

It is preferable that the cells include a specific nucleic acid. The cell number of cells including a specific nucleic acid is not particularly limited and may be appropriately selected depending on the intended purpose so long as the cell number is a plural number.

—Specific Nucleic Acid—

The specific nucleic acid is not particularly limited and may be appropriately selected depending on the intended purpose. Examples of the specific nucleic acid include base sequences used for infectious disease testing, naturally non-existent nucleic acids, animal cell-derived base sequences, and plant cell-derived base sequences. One of these specific nucleic acids may be used alone or two or more of these specific nucleic acids may be used in combination. As the specific nucleic acid, a plasmid can also be suitably used.

A nucleic acid means a polymeric organic compound in which a nitrogen-containing base derived from purine or pyrimidine, sugar, and phosphoric acid are bonded with one another regularly.

The specific nucleic acid is not particularly limited and may be appropriately selected depending on the intended purpose. Examples of the specific nucleic acid include DNA and RNA. Of these specific nucleic acids, for example, DNA corresponding to RNA derived from a fixed area of an infectious disease such as norovirus and naturally non-existent DNA can be suitably used.

The specific nucleic acid included in a plurality of cells may be a specific nucleic acid derived from the cells to be used, or a specific nucleic acid introduced by transgenesis. When a specific nucleic acid introduced by transgenesis and a plasmid are used as the specific nucleic acid, it is preferable to confirm that one copy of the specific nucleic acid is introduced per cell. The method for confirming that one copy of the specific nucleic acid is introduced is not particularly limited and may be appropriately selected depending on the intended purpose. Examples of the method include a sequencer, a PCR method, and a Southern blotting method.

The method for transgenesis is not particularly limited and may be appropriately selected depending on the intended purpose so long as the method can introduce an intended number of specific nucleic acid sequence molecules at an intended position. Examples of the method include homologous recombination, CRISPR/Cas9, TALEN, Zinc finger nuclease, Flip-in, and Jump-in. Particularly, in the case of yeast fungi, homologous recombination is preferable in terms of a high efficiency and ease of controlling.

The metallic particles are not particularly limited and may be appropriately selected depending on the intended purpose. Examples of the metallic particles include silver particles and copper particles. These metallic particles can be used for drawing wiring with liquid droplets discharged.

The inorganic particles are not particularly limited and may be appropriately selected depending on the intended purpose. For example, titanium oxide and silicon oxide are used as white inks or for spacer material coating.

When aggregation of particles occurs, adjustment of the concentration of particles in the particle-containing liquid enables appropriate adjustment of the number of particles in the liquid, based on the theory that the concentration of particles in a liquid and the number of particles in a liquid conform to a Poisson distribution.

The liquid is not particularly limited and may be appropriately selected depending on the intended purpose. For example, various organic solvents such as ion-exchanged water, distilled water, pure water, saline, alcohols, mineral oils, and vegetable oils can be used.

When water is used as a solvent, it is preferable that the water contain a humectant for suppressing water evaporation and a surfactant for reducing the surface tension. For prescription of these agents, common materials used in inkjet inks can be used.

<Two Tubes>

The two tubes (first tube and second tube) are disposed in communication with the liquid retaining section.

For example, the shape, material, size, and structure of the first tube and the second tube are not particularly limited and may be appropriately selected depending on the intended purpose.

Examples of the shape of the first tube and the second tube include a tubular shape and a pipe shape.

Examples of the material of the first tube and the second tube include resins, rubbers, elastomers, and metals. Among these materials, resins are preferable. Examples of the resins include silicon rubbers, nylon, and urethane.

It is preferable that the first tube and the second tube be replaceable, because when changing the kind of the discharging target, the changing only entails replacement of the tubes.

It is preferable that the volume of the first tube and the volume of the second tube be changeable in terms of adjustability to the minimum volume needed, because the amount of the liquid needed for stirring is different depending on the discharging target and a volume that is larger than needed may cause air compression, resulting in a wrong liquid amount and a wrong timing at which the liquid starts to be sucked or ejected, as measured from when a stirring operation is started. The volume of the first tube and the volume of the second tube can be changed by adjusting, for example, the internal diameter, length, and shape of the first and second tubes.

The volume of the first tube and the volume of the second tube can be obtained according to the following formula: volume=$(A/2)^2 \pi \times B$ where A represents the internal diameter of the first tube and the second tube and B represents the length of the first tube and the second tube.

It is preferable that the volume of the first tube and the volume of the second tube be equal to each other, because making the amounts of air to be compressed equal makes it possible to make the intervals from when a stirring operation is started and until when the liquid is actually sucked or ejected equal.

It is preferable that the two tubes be disposed in communication with the liquid retaining section and to be inclined with respect to the liquid droplet discharging ports (nozzle plate). It is more preferable that the two tubes be disposed to be inclined with respect to the center axis passing through the liquid droplet discharging ports.

It is preferable that the angle of inclination of the two tubes be 45 degrees or greater but 80 degrees or smaller with respect to the liquid droplet discharging ports (nozzle plate). With the two tubes having an angle of inclination of 45 degrees or greater but 80 degrees or smaller, it is possible to generate an ascending flow in the liquid retaining section and disperse particles accumulated on the bottom of the liquid retaining section.

It is preferable that the two tubes be disposed symmetrically with respect to the center axis passing through the liquid droplet discharging ports, in terms of making the distribution of particles in the liquid retaining section uniform.

It is preferable that the center axes of the two tubes be not on the same plane, in terms of making it also possible to disperse particles that are present near the internal wall of the liquid retaining section.

For example, the shape, material, size, and structure of the two tubes are not particularly limited and may be appropriately selected depending on the intended purpose.

<First and Second Liquid Sucking/Ejecting Members>

The first and second liquid sucking/ejecting members are coupled to the two tubes (first tube and second tube) respectively.

The first and second liquid sucking/ejecting members are members configured to suck and eject the liquid in the liquid retaining section.

For example, the shape, material, size, and structure of the first and second liquid sucking/ejecting members are not particularly limited and may be appropriately selected depending on the intended purpose.

Examples of the first and second liquid sucking/ejecting members include a pump capable of sucking, retaining, and ejecting a constant amount of a liquid, such as syringe-type and plunger-type motor pumps.

It is preferable that in synchronization with a sucking operation of any one liquid sucking/ejecting member of the first and second liquid sucking/ejecting members, the other liquid sucking/ejecting member perform an ejecting operation. This is preferable because a discharging operation performed by the liquid droplet forming device while maintaining the uniformly dispersed state of the particles contained in the solution in the liquid retaining section does not change the liquid surface height measured from the liquid droplet discharging ports (nozzle plate) and maintains the static pressure applied to the liquid droplet discharging ports (nozzle plate) constant, making it possible to keep the fall velocity of liquid droplets unchanged and discharge liquid droplets at a constant fall velocity with a constant concentration of particles contained.

It is preferable that the first liquid sucking/ejecting member and the second liquid sucking/ejecting member be switchable to a plurality of liquid sending amounts, because this makes it possible to switch to a liquid sucking/ejecting amount needed for sufficiently stirring the discharging target when the kind of the discharging target or the volume of the liquid retaining section is changed.

It is preferable that the liquid sending amount of the first liquid sucking/ejecting member and the liquid sending amount of the second liquid sucking/ejecting member be equal to each other, because this makes it possible to keep the liquid amount in the liquid retaining section unchanged and maintain the liquid surface height constant during stirring.

Here, examples of the liquid sending amount include a liquid sucking amount and a liquid ejecting amount. The highest liquid sucking amount is referred to as the maximum liquid sucking amount, and the highest liquid ejecting amount is referred to as the maximum liquid ejecting amount.

It is preferable that the maximum liquid sucking amounts of the first and second liquid sucking/ejecting members be lower than the volumes of the first tube and the second tube respectively. This makes it possible for the liquid that is being stirred in the liquid retaining section to be adjusted so as not to enter the first and second liquid sucking/ejecting members. This eliminates the need for washing the interior of the first and second liquid sucking/ejecting members or replacing the first and second liquid sucking/ejecting members each time the kind of the discharging target is changed.

It is preferable that in synchronization with a sucking operation of any one liquid sucking/ejecting member of the first and second liquid sucking/ejecting members, the other liquid sucking/ejecting member perform an ejecting operation. This is preferable because a discharging operation performed by the liquid droplet forming device while maintaining the uniformly dispersed state of the particles contained in the solution in the liquid retaining section does not change the liquid surface height measured from the liquid droplet discharging ports (nozzle plate) and maintains the static pressure applied to the liquid droplet discharging ports (nozzle plate) constant, making it possible to keep the fall velocity of liquid droplets unchanged and discharge liquid droplets at a constant fall velocity with a constant concentration of particles contained.

It is preferable that the first liquid sucking/ejecting member and the second liquid sucking/ejecting member be switchable to a plurality of liquid sending velocities.

Here, examples of the liquid sending velocity include a sucking velocity and an ejecting velocity.

It is preferable that the first and second sucking/ejecting members be switchable to a plurality of liquid sending amounts, in terms of preventing liquid amount changes in the liquid retaining section and maintaining discharging stability.

Examples of the liquid sending amount include a liquid sucking amount and a liquid ejecting amount.

It is preferable that the sucking/ejecting member include at least first and second sucking/ejecting members, that while the first sucking/ejecting member is in a sucking or ejecting state, the second sucking/ejecting member be in a non-sucking or non-ejecting state correspondingly, and that sucking/ejecting operations be performed repeatedly in a first sucking or ejecting mode and a second sucking or ejecting mode in which the ejecting velocity is lower than in the first sucking or ejecting mode, because this enables a stirring/sedimentation preventing operation to be performed with a small stirring amount.

It is preferable that a first ejecting mode and a second ejecting mode be continuous, because this makes a stirring operation constant rather than intermittent.

It is preferable that the first ejecting mode and the second ejecting mode be continuous and a first sucking mode be continuous from the second ejecting mode, because this makes a stirring operation constant rather than intermittent from ejecting to sucking.

It is preferable that the time of the first ejecting mode be shorter than the time of the second ejecting mode, because the operation duty of a first dispersing mode is shorter.

It is preferable that the sucking/ejecting member include at least first and second sucking/ejecting members, that while the first sucking/ejecting member is in a sucking or ejecting state, the second sucking/ejecting member be in a non-sucking or non-ejecting state correspondingly, and that the ejecting velocity be lower at the end of sucking/ejecting than at the start of sucking or ejecting, because this makes it possible to perform swirling up at a high ejecting velocity at the start and prevent sedimentation at a low ejecting velocity at the end.

It is preferable that an ejecting operation and a next sucking operation be continuous, because this makes a stirring operation constant rather than intermittent from ejecting to sucking It is preferable to provide a sensing member configured to sense the dispersion state of particles in the liquid retaining section and to determine the ejecting velocity in the first ejecting mode and the ejecting velocity in the second ejecting mode depending on the dispersion state of particles, in terms of maintaining an intended stirring state.

It is preferable to provide a sensing member configured to sense the dispersion state of particles in the liquid retaining section and to determine the ejecting time of the first ejecting mode and the ejecting time of the second ejecting mode depending on the dispersion state of particles, in terms of maintaining an intended stirring state.

It is preferable to provide a sensing member configured to sense the dispersion state of particles in the liquid retaining section and to determine the ejecting velocity at the start of sucking or ejecting depending on the dispersion state of particles, in terms of maintaining an intended stirring state.

It is preferable to provide a sensing member configured to sense the dispersion state of particles in the liquid retaining section and to determine the slope between the ejecting velocity at the start of sucking or ejecting and the ejecting velocity at the end of sucking or ejecting depending on the dispersion state of particles, in terms of maintaining an intended stirring state.

For example, the sensing member may be configured to sense a stained cell with an optical sensor.

It is preferable to provide a sensing range restricting member configured to restrict the range in which the dispersion state of particles in the liquid retaining section is sensed, in terms of maintaining an intended stirring state and stabilizing the sensing accuracy.

Examples of the sensing range restricting member include a polyethylene terephthalate (PET) sheet.

<Sucking/Ejecting Control Unit>

A sucking/ejecting control unit is configured to control a sucking operation and an ejecting operation of the first and second sucking/ejecting members.

The sucking/ejecting control unit is carried out by a computer including various built-in software and programs. The computer is not particularly limited and may be appropriately selected depending on the intended purpose so long as the computer is a device provided with devices for, for example, memory, computing, and control. Examples of the computer include a personal computer.

It is preferable that the sucking/ejecting control unit control switching between an ejecting operation and a sucking operation of the first and second sucking/ejecting members based on a liquid surface height change detection result of a liquid surface detecting member.

The liquid surface detecting member is a member configured to detect the position of a liquid surface in the liquid retaining section. Examples of the target of detection include the height of the liquid surface, any changes in the liquid surface (due to, for example, increase or decrease of the liquid amount or ruffling), and liquid surface observation except for the height.

The liquid surface detecting member is not particularly limited so long as the liquid surface detecting member is capable of detecting the position of the liquid surface of the liquid in the liquid retaining section. Examples of the liquid surface detecting member include an image sensor, a combination of a light emitting element and a position sensor, and a water detection sensor by a photoelectric sensor.

When the liquid surface detecting member senses that the liquid surface height has risen above a prescribed value, it is preferable to perform the following two, in terms of preventing a liquid amount change in the liquid retaining section and maintaining discharging stability.

(1) To bring any one sucking/ejecting member, which performs an ejecting operation, of the first and second sucking/ejecting members to operation termination first, and after the liquid surface height has returned to within the prescribed value range according to the liquid surface detecting member, bring the other sucking/ejecting member, which performs a sucking operation, to operation termination.

(2) To set any one sucking/ejecting member, which performs a sucking operation, of the first and second sucking/ejecting members at a sucking velocity that is higher than an ejecting velocity of the other sucking/ejecting member, which performs an ejecting operation.

In the next sucking/ejecting operation after the operation control of (1) or (2) above is performed, it is preferable that a sucking operation of any one sucking/ejecting member, which performs a sucking operation, of the first and second sucking/ejecting members be started earlier than the start of an ejecting operation of the other sucking/ejecting member, which performs an ejecting operation, by the difference between the times at which the above-described operation terminations of the of the first and second sucking/ejecting members occur, in terms of preventing a liquid amount change in the liquid retaining section and maintaining discharging stability.

When the liquid surface detecting member senses that the liquid surface height has fallen below the prescribed value, it is preferable to perform the following two, in terms of preventing a liquid amount change in the liquid retaining section and maintaining discharging stability.

(3) To bring any one sucking/ejecting member, which performs a sucking operation, of the first and second sucking/ejecting members to operation termination first, and after the liquid surface height has returned to within the prescribed value range according to the liquid surface detecting member, bring the other sucking/ejecting member, which performs an ejecting operation, to operation termination.

(4) To set any one sucking/ejecting member, which performs a sucking operation, of the first and second sucking/ejecting members at an ejecting velocity that is higher than an ejecting velocity of the other sucking/ejecting member, which performs a sucking operation.

In the next sucking/ejecting operation after the operation control of (3) or (4) above is performed, it is preferable that an ejecting operation of any one sucking/ejecting member, which performs an ejecting operation, of the first and second sucking/ejecting members be started earlier than the start of a sucking operation of the other sucking/ejecting member, which performs a sucking operation, by the difference between the times at which the above-described operation terminations of the first and second sucking/ejecting members occur, in terms of preventing a liquid amount change in the liquid retaining section and maintaining discharging stability.

<Sucking/Ejecting Control Unit>

A sucking/ejecting control unit is configured to control a sucking operation and an ejecting operation of the first and second sucking/ejecting members.

The sucking/ejecting control unit is carried out by a computer including various built-in software and programs. The computer is not particularly limited and may be appropriately selected depending on the intended purpose so long as the computer is a device provided with devices for, for example, memory, computing, and control. Examples of the computer include a personal computer.

In the present disclosure, by controlling the ejecting/sucking operations of the sucking/ejecting members according to the amounts of backlash of the two sucking/ejecting members configured to stir the liquid in the liquid retaining section, it is possible to eliminate a time difference between the two sucking/ejecting members in switching between an ejecting operation and a sucking operation and maintain the liquid surface height in the liquid retaining section constant. The specific measures for achieving this object are as described in (1) and (2) below.

(1) To drive the first sucking/ejecting member to perform sucking/ejecting operations continuously and drive the second sucking/ejecting member to perform sucking/ejecting operations intermittently, and vary the intermittent stop period of the second sucking/ejecting member according to information on a delay time from when each sucking/ejecting member starts to be driven to perform sucking/ejecting operations until the start of sucking/ejecting operations.

(2) To drive the first and second sucking/ejecting members to perform sucking/ejecting operations intermittently, and vary the intermittent stop periods of the first and second sucking/ejecting members according to information on a delay time from when each sucking/ejecting member starts to be driven to perform sucking/ejecting operations until the start of sucking/ejecting operations.

Here, "continuous" means that input signals for driving the first and second sucking/ejecting members do not contain suspension periods at the switch from sucking to ejecting or from ejecting to sucking.

Conversely to "continuous", "intermittent" means that input signals for driving the first and second sucking/ejecting members contain suspension periods at the switch from sucking to ejecting or from ejecting to sucking.

The information on a delay time also includes drive pulses for the first and second sucking/ejecting members, in addition to a delay time.

The information on a delay time from when the first and second sucking/ejecting members start to be driven to sucking/ejecting operations until the start of sucking/ejecting operations is sensed by a delay sensing member.

It is preferable that the delay sensing member sense starts of plunger movement of the first and second sucking/ejecting members, because a delay time of a sucking/ejecting member alone, not of the system, can be measured with ease.

A plunger of a sucking/ejecting member repeats going and returning movements in a cylinder, and a start of plunger movement means a timing at which the plunger starts to move in response to switch of the moving direction of the plunger.

Examples of the delay sensing member configured to sense starts of plunger movement of the first and second sucking/ejecting members include a laser-type displacement sensor.

It is preferable that the delay sensing member sense the liquid surface height in the liquid retaining section.

Examples of the delay sensing member configured to sense the liquid surface height in the liquid retaining section include level sensors utilizing ultrasonic waves, electrical waves, and lasers.

It is preferable that the delay sensing member be operated when the power is turned on, because this makes it possible to adapt to any change of the delay time due to, for example, maintenance during an OFF period of the power.

It is preferable that the delay sensing member be operated when a predetermined operation time has passed, because this makes it possible to adapt to any change of the delay time due to, for example, deterioration of parts over time.

The predetermined operation time means a time for which a sucking/ejecting member has performed sucking/ejecting operations, and may be a time from when the power is turned on or an actual time from when the system was installed.

It is preferable that the delay sensing member be operated when the number of times a sucking or ejecting operation is performed has passed a predetermined number of times, because this makes it possible to adapt to any change of the delay time due to, for example, wear of the parts. It is considered sufficient to sense a delay time each time a sucking or ejecting operation has been performed some tens through some hundreds of times, because wearing does not occur suddenly. However, it is also possible to sense the delay time each time.

The predetermined number of times a sucking or ejecting operation is performed refers to the number of times a sucking/ejecting member has performed a sucking operation or an ejecting operation, or the number of times switching between sucking and ejecting has been performed. Because sucking and ejecting are a set in the liquid droplet discharging unit of the present disclosure, a sucking operation and an ejecting operation may be counted as one operation.

<Correcting Unit>

A correcting unit is configured to determine a correcting amount by which an ejecting amount of any one sucking/ejecting member of the first and second sucking/ejecting members is corrected relative to a sucking amount of the other sucking/ejecting member.

The correcting unit is carried out by a computer including various built-in software and programs. The computer is not particularly limited and may be appropriately selected depending on the intended purpose so long as the computer is a device provided with devices for, for example, memory, computing, and control. Examples of the computer include a controller provided with a microcomputer, a PLC, and a personal computer.

The liquid ejecting amount of the any one sucking/ejecting member of the first and second sucking/ejecting members may be set higher than the sucking amount of a liquid sucking operation of the other sucking/ejecting member by the correcting amount determined by the correcting unit. This maintains the liquid amount in the liquid retaining section constant even when discharging has been performed for a long time, making it possible to maintain the discharging velocity at which liquid droplets are discharged constant.

It is preferable that the correcting amount of the correcting unit be determined based on any one of a liquid amount to be discharged, a discharging frequency, and a time taken by any one of the first and second sucking/ejecting members to perform sucking or ejecting, because this needs no additional correcting member and can prevent cost increase.

<Liquid Amount Detecting Member>

In the present disclosure, it is preferable to provide a liquid amount detecting member configured to detect a liquid amount in the liquid retaining section, because this makes it possible to detect a change in the liquid amount due not only to discharging but also to volatilization.

It is preferable that the correcting amount of the correcting unit be determined based on the amount of change in the liquid amount in the liquid retaining section detected by the liquid amount detecting member, because this makes it possible to correct also an amount of change in the liquid amount due not only to discharging but also to volatilization.

Examples of the liquid amount detecting member include a sensor configured to count the number of liquid droplets discharged, and a sensor configured to capture an image of the liquid surface and detect the position of the liquid surface by image processing.

Examples of the sensor configured to count the number of liquid droplets include a discharging signal output counter in a controller provided with a microcomputer.

Examples of the sensor configured to capture an image of the liquid surface and detect the position of the liquid surface by image processing include a camera, a capacitance-type liquid amount detecting sensor, and in the case of an opaque liquid, a laser displacement sensor provided above.

<Other Members>

The other members are not particularly limited and may be appropriately selected depending on the intended purpose. It is preferable to provide a control member.

(Liquid Droplet Forming Device)

A liquid droplet forming device of the present disclosure includes the liquid droplet discharging unit of the present disclosure, preferably includes a driving unit and a particle number counting unit, and further includes other units as needed.

<Driving Unit>

The driving unit is not particularly limited and may be appropriately selected depending on the intended purpose. When the liquid droplet discharging unit is a piezoelectric pressurizing-type inkjet head, examples of the driving unit include a unit configured to input a drive voltage to the liquid droplet discharging unit. In this case, it is possible to discharge minute liquid droplets, by a piezoelectric element being deformed by the driving unit.

<Particle Number Counting Unit>

The particle number counting unit is a unit configured to count the number of particles contained in liquid droplets, and is preferably a unit configured to count the number of particles contained in liquid droplets with a sensor after the liquid droplets are discharged and before the liquid droplets land on a landing target.

A sensor means a device configured to, by utilizing some scientific principles, change mechanical, electromagnetic, thermal, acoustic, or chemical properties of natural phenomena or artificial products or spatial information/temporal information indicated by these properties into signals, which are a different medium easily handleable by humans or machines.

The particle number counting unit is not particularly limited, may be appropriately selected depending on the intended purpose, and may include an operation for observing particles before discharging and an operation for counting particles after landing.

For counting the number of particles contained in the liquid droplets after the liquid droplets are discharged and before the liquid droplets land on the landing target, it is preferable to observe particles in a liquid droplet at a timing at which the liquid droplet is at a position that is immediately above a well opening and at which the liquid droplet is predicted to enter the well in a plate as the landing target without fail.

The plate is not particularly limited, and a plate that is commonly used in bio fields and in which holes are formed can be used.

The number of wells in the plate is not particularly limited and may be appropriately selected depending on the intended purpose. The number of wells may be a single number or a plural number.

As a plate with a plural number of wells, it is preferable to use plates in which 24, 96, 384, or such a number of wells or holes as commonly used in the industry are formed with dimensions commonly used in the industry.

The material of the plate is not particularly limited and may be appropriately selected depending on the intended purpose. In consideration of a post-treatment, it is preferable to use a material that suppresses adhesion of cells and nucleic acids to wall surfaces.

Examples of the method for observing particles in the liquid droplet include an optical detection method and an electric or magnetic detection method.

<Other Units>

The other units are not particularly limited and may be appropriately selected depending on the intended purpose. Examples of the other units include a control unit and a recording unit.

(Stirring Device)

A stirring device of the present disclosure include a liquid retaining section configured to retain a liquid, two tubes disposed in communication with the liquid retaining section, and first and second liquid sucking/ejecting members coupled to the two tubes respectively. While the first liquid sucking/ejecting member is in a sucking or ejecting state, the second liquid sucking/ejecting member is in a non-sucking or non-ejecting state correspondingly. The stirring device further includes other members as needed.

It is preferable that the two tubes be disposed to be inclined with respect to the bottom of the liquid retaining section.

The stirring device can suppress sedimentation of particles in the liquid retaining section and maintain a uniformly dispersed state of particles constantly.

The liquid retaining section, the two tubes, the first and second liquid sucking/ejecting members, and the other members of the stirring device are the same as the liquid retaining section, the two tubes, the first and second liquid sucking/ejecting members, and the other members of the liquid droplet discharging unit described above.

Because the liquid droplet forming device of the present disclosure includes the liquid droplet discharging unit capable of maintaining the liquid surface height in the liquid retaining section constant, the liquid droplet forming device is suitably used in various fields. Particularly, the liquid droplet forming device is suitably used in a below-described dispensing device used in the present disclosure.

(Dispensing Device)

A dispensing device used in the present disclosure includes the liquid droplet forming device of the present disclosure, preferably includes a control unit, and further includes other units as needed.

The dispensing device is configured to discharge liquid droplets toward a landing target and land the liquid droplets on the landing target.

<Landing Target>

The landing target is a member on which liquid droplets discharged by the liquid droplet discharging unit of the liquid droplet forming device land.

For example, the material, shape, size, and structure of the landing target are not particularly limited and may be appropriately selected depending on the intended purpose, so long as liquid droplet discharged can adhere to the landing target.

The material of the landing target is not particularly limited and may be appropriately selected depending on the intended purpose. Preferable examples of the landing target include landing targets formed of, for example, semiconductors, ceramics, metals, glass, quartz glass, and plastics.

The shape of the landing target is not particularly limited and may be appropriately selected depending on the intended purpose. Examples of the shape of the landing target include a board shape and a plate shape.

The structure of the landing target is not particularly limited and may be appropriately selected depending on the intended purpose. For example, the landing target may have a single-layer structure or a multilayered structure.

Examples of the landing target include a well plate in which a plurality of concaves are formed, and a glass plate including no concaves. Of these landing targets, a well plate is preferable.

Use of a well plate is preferable, because when the particle number counting unit of the liquid droplet forming device judges that the number of particles contained in a liquid droplet is 0 particles, discharging of a liquid droplet again into the same concave by the liquid droplet discharging unit ensures that a particle is dispensed into the concave without fail.

The number of concaves formed in a well plate is a plural number, preferably 2 or greater, more preferably 5 or greater, and yet more preferably 50 or greater.

<Control Unit>

The control unit is a unit configured to control a relative positional relationship between the liquid droplet discharging unit and the landing target. For example, the control unit includes a CPU (Central Processing Unit), a ROM (Read Only Memory), a RAM (Random Access Memory), and a main memory, and is configured to execute various operations according to a control program for controlling the operation of the entire dispensing device.

<Other Units>

The other units are not particularly limited and may be appropriately selected depending on the intended purpose. Examples of the other units include a recording unit, a culturing unit, a heating unit, a stirring unit, and a washing unit.

The dispensing device used in the present disclosure includes a particle number counting device of the present disclosure having an improved accuracy for sensing particles contained in discharged liquid droplets and having a high productivity capable of increasing the number of liquid droplets discharged per unit time. Therefore, the dispensing device is suitably used for producing a tissue, particularly a three-dimensional tissue that can be widely used in various fields such regenerative medicine and evaluation of safety and efficacy of medical drugs, cosmetics, and chemical substances.

The embodiments of the liquid droplet forming device of the present disclosure will be described in detail with reference to the drawings.

The liquid droplet forming device of the present disclosure employs the liquid droplet discharging unit of the present disclosure as a liquid droplet discharging unit, and the liquid droplet discharging unit of the present disclosure is included in the liquid droplet forming device of the present disclosure. Therefore, the embodiments of the liquid droplet discharging unit of the present disclosure will also be described through the following description of the embodiments of the liquid droplet forming device of the present disclosure.

Note that the same constituents may be denoted by the same reference numerals throughout the drawings, and redundant description may be skipped. Further, for example, the number, position, and shape of the constituents to be described below are not limited to the embodiments, and may be set to the preferable number, position, and shape for carrying out the present disclosure.

Embodiment 1A

First, the configuration of the liquid droplet forming device according to an embodiment 1A will be described.

Figure 2:
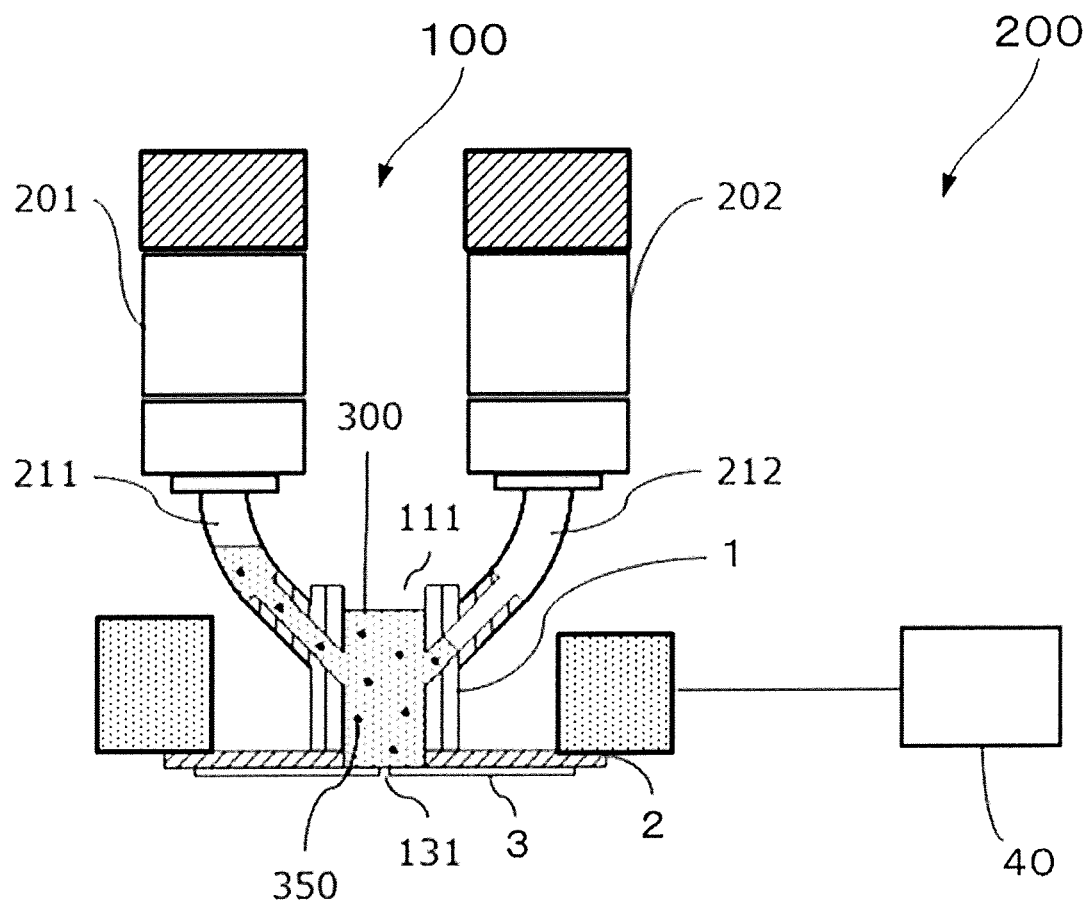
FIG. 2 is a diagram illustrating an example of a liquid droplet forming device according to embodiments 1A and 1B.

FIG. 2 is a diagram illustrating an example of a liquid droplet forming device 200 according to the embodiment 1A. With reference to FIG. 2, the liquid droplet forming device 200 includes a liquid droplet discharging unit 100 and a driving unit 40.

The liquid droplet discharging unit 100 includes a liquid retaining section 1, a vibration member 2, a nozzle plate 3 including liquid droplet discharging ports (nozzles) 131, two tubes (a first tube 211 and a second tube 212), and first and second liquid sucking/ejecting members 201 and 202. FIG. 2 exemplarily illustrates a state that a solution 300 containing particles 350 is retained in the liquid retaining section 1.

In the present embodiment, expediently, the liquid retaining section 1 side is defined as upper side and the nozzle plate 3 side is defined as lower side. A surface of each portion on the liquid retaining section 1 side is defined as upper surface, and a surface of each portion on the nozzle plate 3 side is defined as lower surface. When it is said that a target is seen in a plan-view perspective, it is meant that the target is seen from a perspective normal to the upper surface of the nozzle plate 3. A planer shape refers to the shape of a target seen from the perspective normal to the upper surface of the nozzle plate 3.

In the liquid droplet discharging unit 100, the liquid retaining section 1 retains a solution 300 containing particles 350 (a solution 300 in which particles 350 are dispersed), and may be formed of, for example, a metal, a resin, a silicon, or a ceramic.

At the top, the liquid retaining section 1 includes an atmospherically exposed portion 111 configured to expose the interior of the liquid retaining section 1 to the atmosphere, and bubbles mixed in the solution 300 can be evacuated through the atmospherically exposed portion 111.

The nozzle plate 3 is secured at the lower end of the liquid retaining section 1 via the vibration member 2.

The liquid droplet discharging ports (nozzles) 131, which are through holes, are formed in approximately the center of the nozzle plate 3, and vibration of the nozzle plate 3 causes the solution 300 retained in the liquid retaining section 1 to be discharged through the nozzles 131 in the form of liquid droplets. The planer shape of the nozzle plate 3 may be, for example, a circular shape, but may be, for example, an elliptic shape or a quadrangular shape.

The material of the nozzle plate 3 is not particularly limited and may be appropriately selected depending on the intended purpose. If the material of the nozzle plate 3 is extremely flexible, the nozzle plate 3 easily undergo vibration and is not easily able to stop vibration immediately when there is no need for discharging. Therefore, it is preferable to use a material having a certain degree of hardness. Metallic materials and ceramic materials, or polymeric materials having a certain degree of hardness can be used. A material having a low adhesiveness with the particles 350 is particularly preferable.

It is preferable that the liquid droplet discharging ports (nozzles) 131 be formed in the form of substantially true-circular through holes in approximately the center of the nozzle plate 3. In this case, the diameter of the nozzles 131 is not particularly limited and may be appropriately selected depending on the intended purpose. It is preferable that the diameter of the nozzles 131 be twice or more greater than the size of the particles 350 in order to avoid clogging of the particles 350 in the nozzles 131.

The vibration member 2 is formed on the upper surface side of the nozzle plate 3.

The shape of the vibration member 2 may be designed to match the shape of the nozzle plate 3. For example, when the planer shape of the nozzle plate 3 is a circular shape, it is preferable to form the vibration member 2 having an annular (ring-like) planar shape around the nozzle 131.

The vibration member 2 is a piezoelectric element obtained by providing the upper surface and the lower surface of a piezoelectric material with electrodes across which a voltage is to be applied. When a voltage is applied across the upper and lower electrodes of the vibration member 2, a compressive stress is applied in the horizontal direction of the drawing sheet, making it possible for the nozzle plate 3 to vibrate.

The vibration member configured to vibrate the nozzle plate 3 is not limited to a piezoelectric element. For example, a material having a different coefficient of linear expansion from the coefficient of linear expansion of the nozzle plate 3 may be pasted over the nozzle plate 3. By heating the material, it is possible to vibrate the nozzle plate 3, utilizing the difference between the coefficients of linear expansion. Here, it is preferable to form a heater in the material having the different coefficient of linear expansion and configure the nozzle plate 3 to be vibrated by heating the heater through electrification.

The driving unit 40 is a unit configured to drive the vibration member 2. The driving unit 40 can apply to the vibration member 2, a discharging waveform for vibrating the nozzle plate 3 to form liquid droplets.

That is, by applying the discharging waveform to the vibration member 2 and controlling the vibration state of the nozzle plate 3, the driving unit 40 can cause the solution 300 retained in the liquid retaining section 1 to be discharged through the nozzles 131 in the form of liquid droplets.

Examples of the particles 350 in the solution 300 containing the particles 350 include metallic particles, inorganic particles, and cells. Among these particles, cells are preferable.

Water is the most common as the solvent of the solution 300. However, the solvent is not limited to water, but various organic solvents such as alcohols, mineral oils, and vegetable oils may be used.

The amount of the solution 300 retained in the liquid retaining section 1 is not particularly limited, may be appropriately selected depending on the intended purpose, and is preferably from 1 microliter through 1 milliliter. Particularly, in the case of using an expensive liquid such as a cell suspension, the amount of the solution 300 retained is more preferably from 1 microliter through 200 microliters in terms of forming liquid droplets with a small liquid amount.

Both of the first tube 211 and the second tube 212 are silicone rubber tubes having an internal diameter of 2 mm and a length of 50 mm. The internal diameter and the length of the silicone rubber tubes are not particularly limited and may be appropriately selected.

The first tube 211 and the second tube 212 are replaceable, and the volumes of the first tube 211 and the second tube 212 can be changed by adjusting the length and the internal diameter.

The two tubes (first tube 211 and second tube 212) are disposed to be inclined with respect to the nozzles 131 (nozzle plate 3). That is, the two tubes are disposed to be inclined with respect to the center axis passing through the nozzles 131.

As the disposition of the first tube 211 and the second tube 212, it is preferable to dispose the tubes in a manner that an extension line of the center axis of each tube at the linking portion falls on a corner portion formed by the nozzle plate 3 and the vibration member 2, or is slightly off from the corner portion toward the nozzles 131.

The first and second liquid sucking/ejecting members 201 and 202 are in communication with the liquid retaining section 1 through the two tubes (first tube 211 and second tube 212).

Examples of the first and second liquid sucking/ejecting members 201 and 202 include a pump capable of sucking, retaining, and ejecting a constant amount of a liquid, such as syringe-type and plunger-type motor pumps.

Next, a process through which a liquid droplet is formed by the liquid droplet forming device 200 according to the embodiment 1A will be described.

Figure 3:
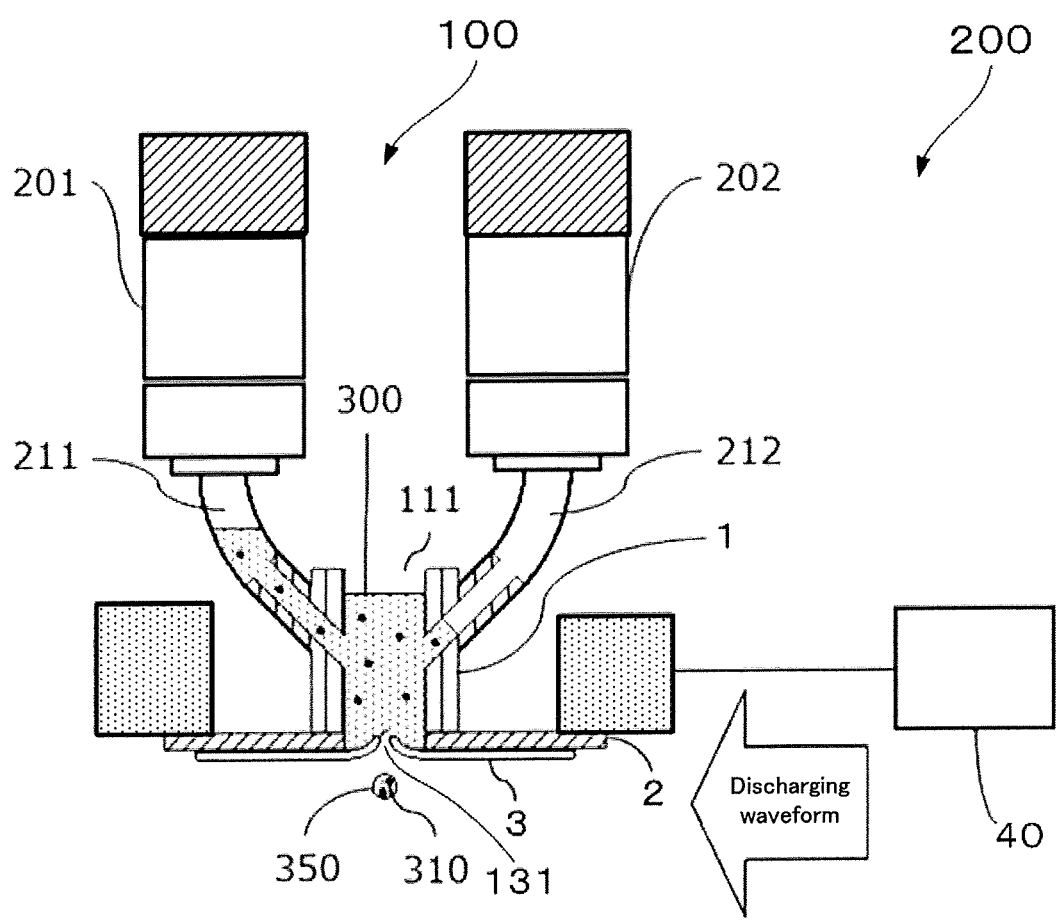
FIG. 3 is a diagram illustrating an example of a process through which a liquid droplet is formed by a liquid droplet discharging unit of a liquid droplet forming device according to the embodiments 1A and 1B.

FIG. 3 is a diagram illustrating the process through which a liquid droplet is formed by the liquid droplet forming device 200. FIG. 3 exemplarily illustrates a state of a liquid droplet 310 being formed by vibration of the nozzle plate 3 with a discharging waveform input to the vibration member 2 from the driving unit 40. Through the vibration member 2, a portion of the nozzle plate 3 free of contact with the vibration member 2 is caused to vibrate in accordance with the discharging waveform, resulting in the highest amplitude at the nozzles 131. The vibration of the nozzles 131 causes the solution 300 in the liquid retaining section 1 to be discharged in the form of liquid droplets 310.

Embodiment 2A

Figure 4A:
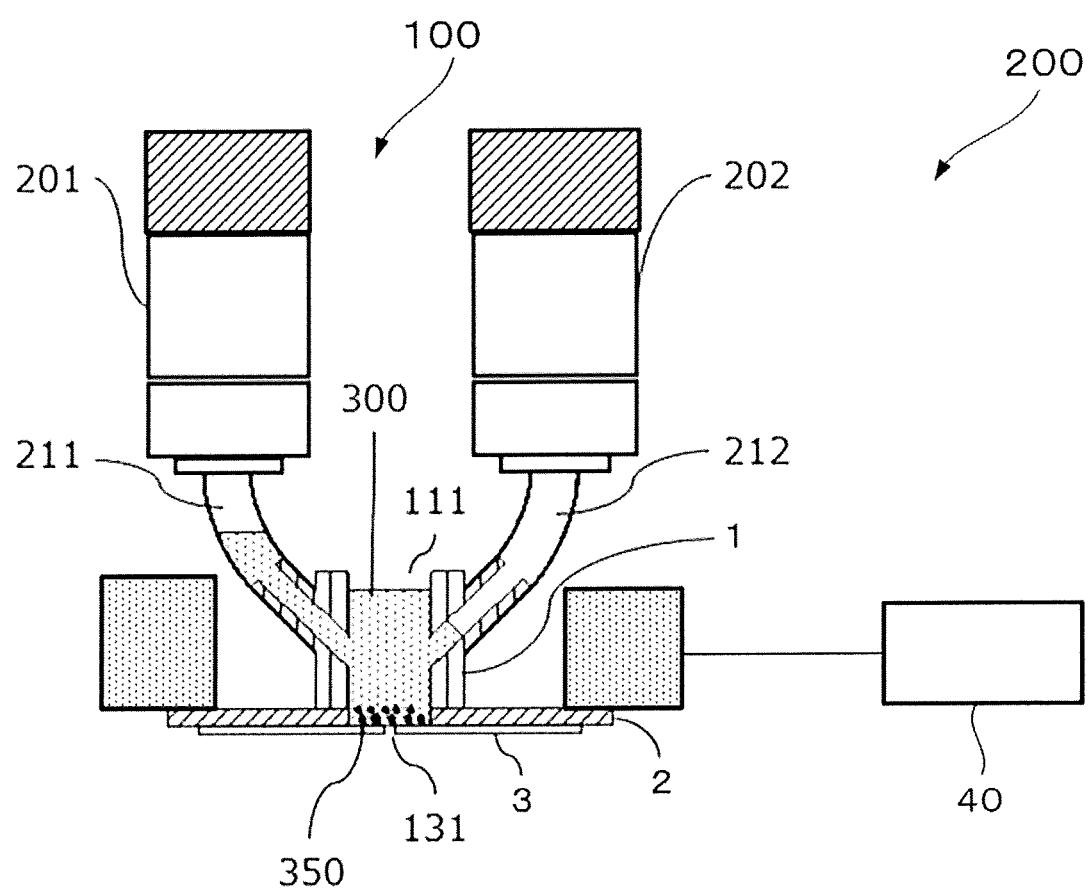
FIG. 4A is a diagram illustrating an example depicting liquid stirring using first and second liquid sucking/ejecting members of a liquid droplet forming device according to an embodiment 2A.
Figure 4B:
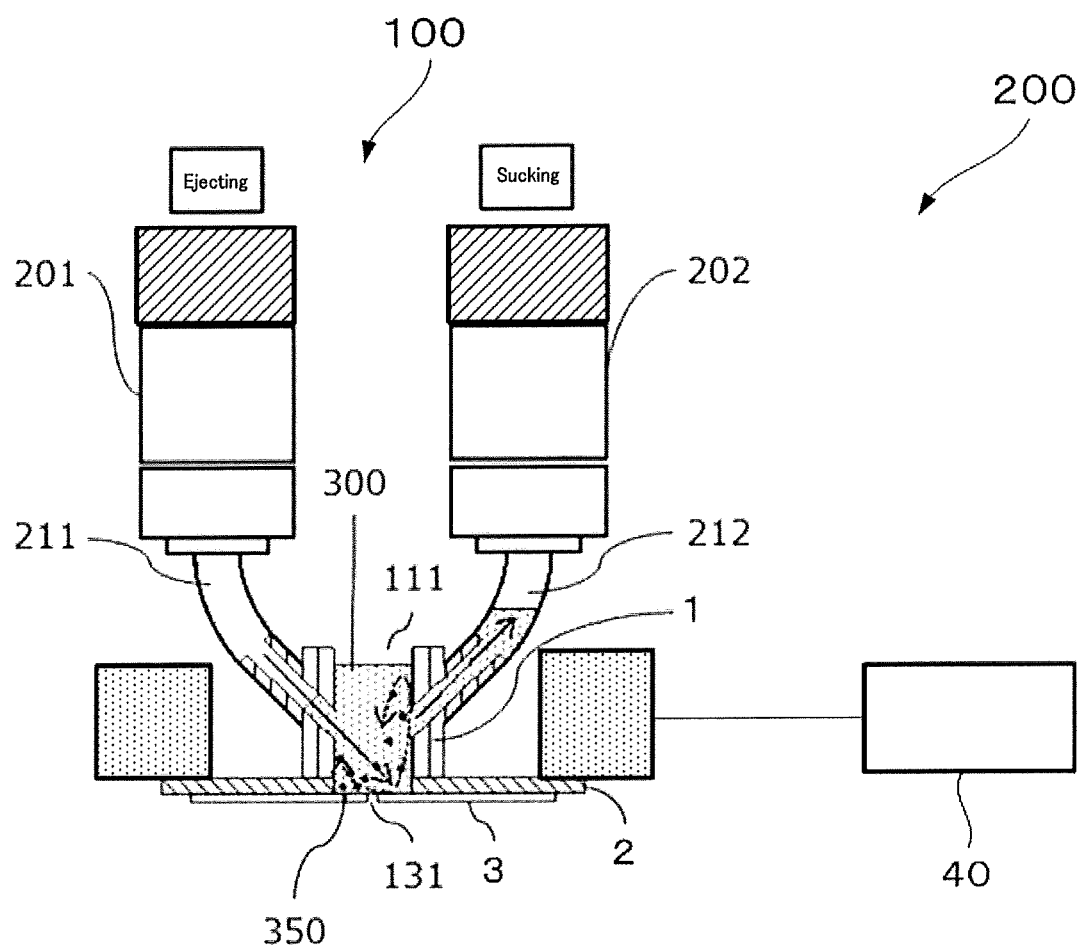
FIG. 4B is a diagram illustrating another example depicting liquid stirring using first and second liquid sucking/ejecting members of a liquid droplet forming device according to an embodiment 2A.
Figure 4C:
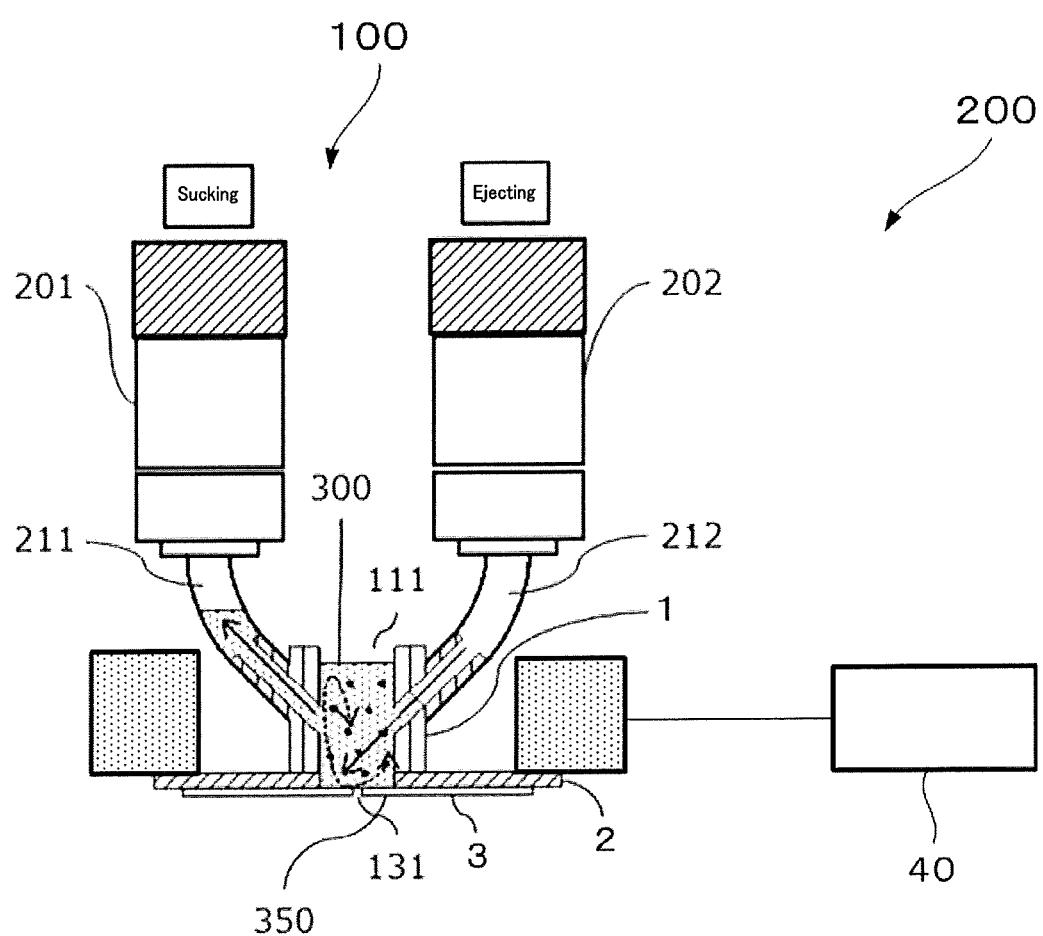
FIG. 4C is a diagram illustrating another example depicting liquid stirring using first and second liquid sucking/ejecting members of a liquid droplet forming device according to the embodiment 2A.

FIG. 4A to FIG. 4C are diagrams depicting a liquid stirring operation using the first and second liquid sucking/ejecting members 201 and 202.

FIG. 4A is a diagram illustrating a state that the solution 300 containing the particles 350 is poured in the liquid retaining section 1 and left to stand still. In this state, the particles 350 have undergone sedimentation and accumulated on the bottom of the liquid retaining section 1 due to free sedimentation of the particles 350. If a discharging waveform is input from the driving unit 40 and a liquid droplet discharging operation is performed while in this state in which the particles 350 have aggregated near the nozzles 131, the aggregated particles 350 may clog the nozzles 131, resulting in the problem of discharging failure in which no liquid droplets are formed.

Even if liquid droplets can be formed, liquid droplets formed initially are discharged in a state of containing particles 350 in a large amount, and the content of particles 350 in the liquid droplets gradually decreases. When the particles 350 above the nozzles have been discharged, only the supernatant will be discharged, resulting in the problem of a large variation in the content of particles 350 in the liquid droplets over time.

FIG. 4B and FIG. 4C are diagrams illustrating a process of re-dispersion of the particles 350 by stirring of the solution 300 retained in the liquid retaining section 1 using the first and second liquid sucking/ejecting members 201 and 202.

The first and second liquid sucking/ejecting members 201 and 202 are in communication with the liquid retaining section 1 through the two tubes (first tube 211 and second tube 212). The first tube 211 and the second tube 212 are disposed to be inclined with respect to the nozzles 131 (nozzle plate 3). That is, the tubes are disposed to be inclined with respect to the center axis passing through the nozzles 131.

As the disposition of the first tube 211 and the second tube 212, it is preferable to dispose the two tubes in a manner that an extension line of the center axis of each tube at the portion linking to the liquid retaining section 1 falls on a corner portion formed by the nozzle plate 3 and the vibration member 2, or is slightly off from the corner portion toward the nozzles 131.

Examples of the first and second liquid sucking/ejecting members 201 and 202 include a pump capable of sucking, retaining, and ejecting a constant amount of a liquid, such as syringe-type and plunger-type motor pumps.

As illustrated in FIG. 4A, any one of the first and second liquid sucking/ejecting members 201 and 202 performs a previous sucking operation to put the interior of the first tube 211 at a negative pressure, in order to suck and hold a certain amount from the solution 300 in the liquid retaining section 1. The present embodiment illustrates an example in which sucking/holding is performed by the first liquid sucking/ejecting member 201.

In FIG. 4B, the first liquid sucking/ejecting member 201 performs an ejecting operation and the second liquid sucking/ejecting member 202 performs a sucking operation.

By the ejecting operation, the first liquid sucking/ejecting member 201 puts the interior of the first tube 211 at a positive pressure and ejects the sucked and held solution 300 into the liquid retaining section 1. The ejected solution 300 forms a flow that is approximately parallel with the center axis of a portion of the first tube 211 linking to the liquid retaining section 1, and acts to swirl up the particles 350 accumulated on the corner portion formed by the nozzle plate 3 and the vibration member 2 upward in the liquid retaining section 1 by an ascending flow along the wall surface of the liquid retaining section 1. The flow that has ascended along the wall surface of the liquid retaining section 1 becomes a flow to head toward the center of the liquid retaining section 1 at about the liquid surface, and this liquid flow brings the particles 350 which are present at the second tube 212 side as seen from the center of the nozzles 131 into a dispersed state.

By performing a sucking operation, the second liquid sucking/ejecting member 202 puts the interior of the second tube 212 at a negative pressure to suck and hold a certain amount from the solution 300 in the liquid retaining section 1.

Successively, as illustrated in FIG. 4C, the second liquid sucking/ejecting member 202 performs an ejecting operation to bring the particles 350 which are present in the liquid retaining section 1 at the first tube 211 side as seen from the center axis passing through the nozzles 131 into a dispersed state.

Through repetition of the operations described above, the particles 350 that have undergone sedimentation onto the bottom of the liquid retaining section 1 can be re-dispersed with a small amount of a liquid. By performing the liquid droplet forming operation illustrated in FIG. 3 in the re-dispersed state, it is possible to prevent a discharging failure due to sedimentation of the particles 350 and temporal variation of the content concentration of particles 350 to be contained in the liquid droplets 310 discharged.

It is preferable that the first tube 211 and the second tube 212 be disposed symmetrically, because one-sided disposition of the tubes with respect to the center axis passing through the nozzles 31 makes the distribution of the particles 350 in the liquid retaining section 1 non-uniform.

It is preferable that the first and second liquid sucking/ejecting members 201 and 202 have the same sucking velocity, the same ejecting velocity, the same liquid sucking amount, and the same liquid ejecting amount with each other, in order to disperse the particles 350 in the liquid retaining section 1 uniformly.

Embodiment 3A

Figure 5:
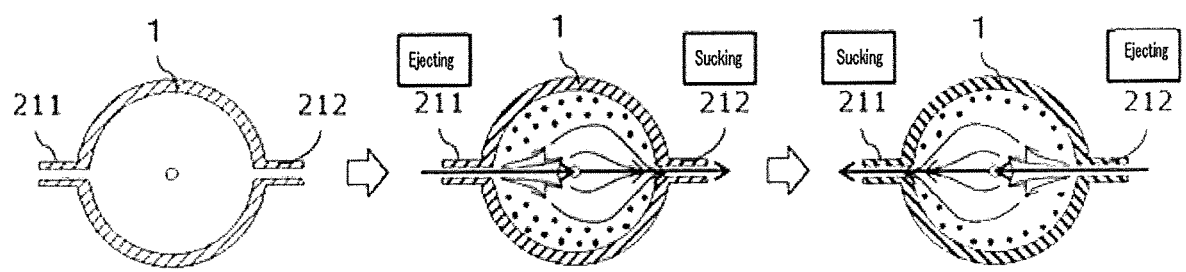
FIG. 5 is a diagram illustrating an example depicting disposition of first and second tubes of a liquid droplet forming device according to an embodiment 3A.
Figure 6:
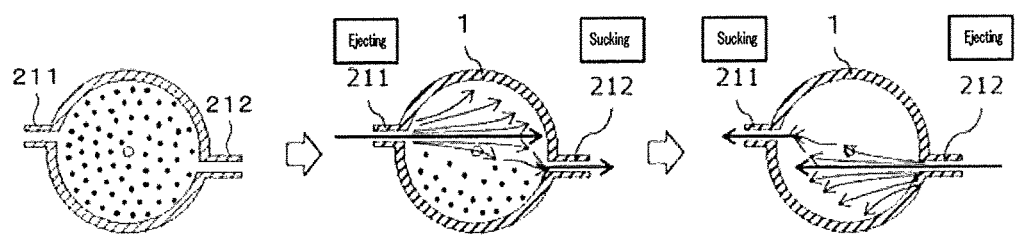
FIG. 6 is a diagram illustrating another example depicting disposition of first and second tubes of a liquid droplet forming device according to the embodiment 3A.

FIG. 5 and FIG. 6 are diagrams depicting the disposition of the first tube 211 and the second tube 212.

FIG. 5 and FIG. 6 are diagrams illustrating the liquid retaining section 1, the first tube 211, and the second tube 212 in a plan-view perspective.

As illustrated in FIG. 5, assume a case where the horizontal sectional area of the liquid retaining section is greater than the diameter of the sucking/ejecting port of the tubes as illustrated in the diagram, and the first tube 211 and the second tube 212 are disposed in a manner that the center axes of the tubes are on the same plane. In this case, there is no problem when the first liquid sucking/ejecting member 201 and the second liquid sucking/ejecting member 202 are operated alternately, but when a sucking operation of any one of the liquid sucking/ejecting members is performed at the same time as a part or the whole of an ejecting operation of the other liquid sucking/ejecting member, it is predicted that a stirring flow generated in the liquid retaining section 1 by an ejecting operation is hindered by a sucking operation of the other liquid sucking/ejecting member from being spread in the liquid retaining section 1, but acts as a stirring flow at only about the plane connecting the center axes of the first tube 211 and the second tube 212. In other words, in the case of a configuration in which the sucking/ejecting ports of the tubes 211 and the 212 fully face each other as seen from the upper surface of the liquid retaining section 1, it is assumed that a partial region where the sucking/ejecting ports face each other is mainly stirred.

As compared, by disposing the first tube 211 and the second tube 212 in a manner that the center axes of the tubes are not on the same plane as illustrated in FIG. 6, it is possible to disperse also the particles 350 near the internal wall of the liquid retaining section 1. It is also possible to vary the height of the sucking ports (or ejecting ports) of the first tube 211 and the second tube 212 or the angle of inclination of the tubes from each other. When the horizontal section of the liquid retaining section 1 has a circular shape as in the present embodiment, the first tube 211 and the second tube 212 may be disposed to face each other, and the vertical section of the sucking/ejecting port of each tube may be disposed to be parallel with a tangent.

Embodiment 4A

Figure 7A:
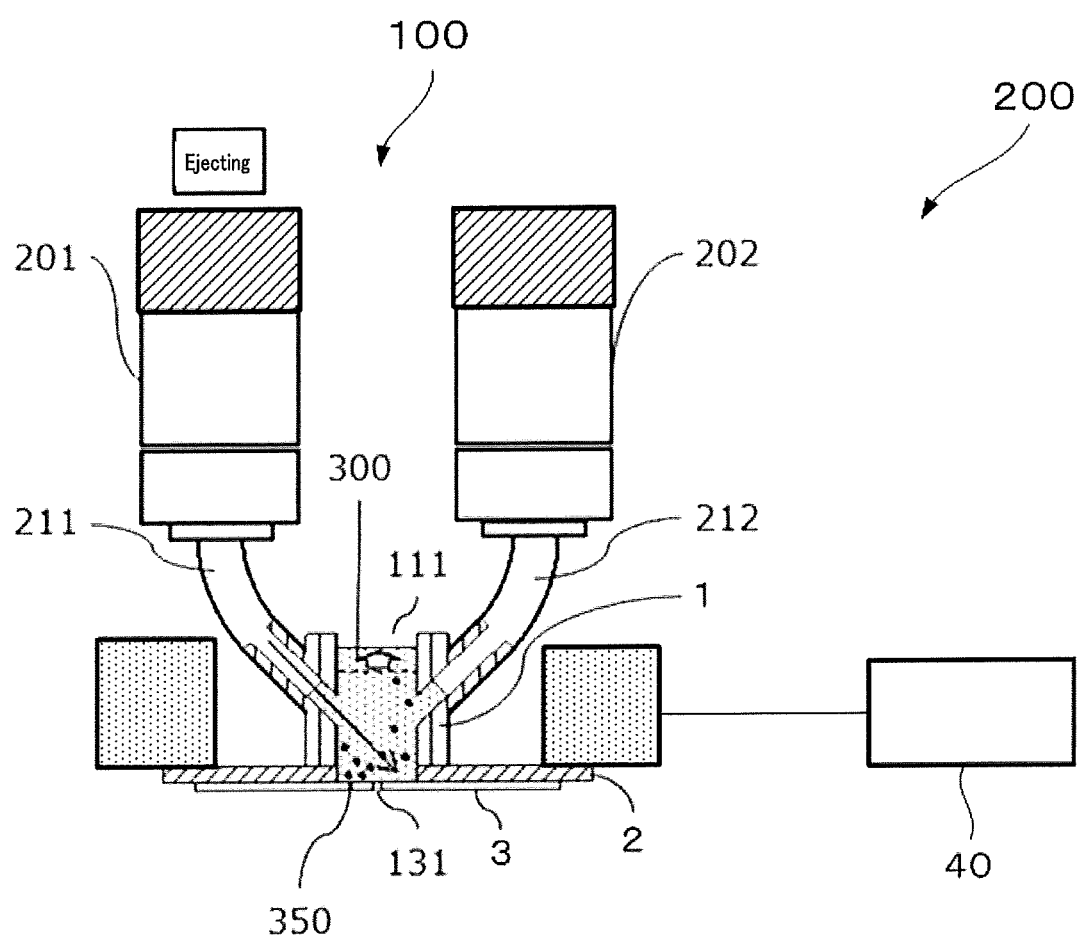
FIG. 7A is a diagram illustrating an example depicting a specific timing of a sucking/ejecting operation of a liquid droplet forming device according to an embodiment 4A.
Figure 7B:
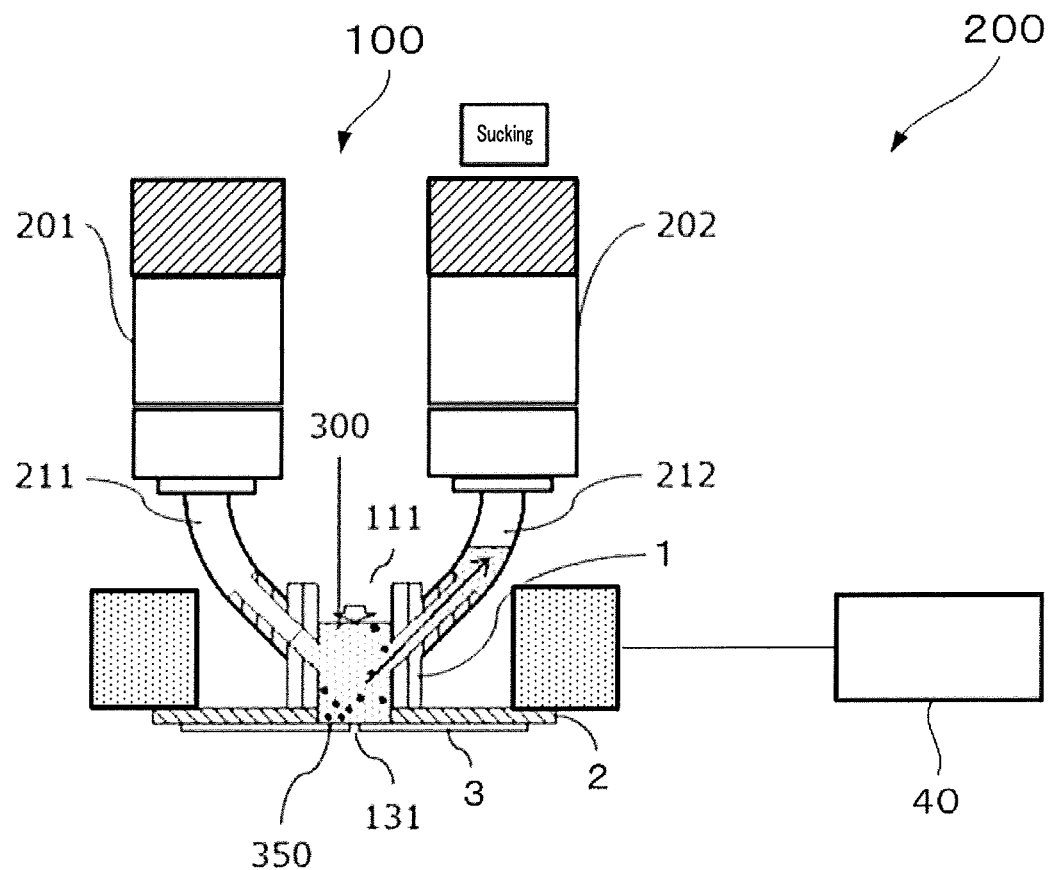
FIG. 7B is a diagram illustrating another example depicting a specific timing of a sucking/ejecting operation of a liquid droplet forming device according to the embodiment 4A.

FIG. 7A and FIG. 7B are diagrams depicting a specific timing of a sucking/ejecting operation.

FIG. 7A and FIG. 7B illustrate a case where the first liquid sucking/ejecting member 201 and the second liquid sucking/ejecting member 202 are operated alternately.

FIG. 7A illustrates a state that the first liquid sucking/ejecting member 201 performs an ejecting operation to generate a stirring flow in the solution 300 in the liquid retaining section 1 to re-disperse the particles 350 that have undergone sedimentation. Here, because the solution that has been previously sucked into the first tube 211 flows into the liquid retaining section 1, the liquid amount of the solution 300 in the liquid retaining section 1 is increased to raise the liquid surface.

FIG. 7B illustrates a state that the second liquid sucking/ejecting member 202 performs a sucking operation during or after completion of the ejecting operation of the first liquid sucking/ejecting member 201. By the second liquid sucking/ejecting member 202 sucking the liquid amount that has flowed in in FIG. 7A into the second tube 212, it is possible to return the liquid amount of the solution 300 in the liquid retaining section 1 to the state before the operation. In the case of re-dispersing the particles 350 that have undergone sedimentation in a state that liquid droplet discharging is stopped, the operation described here can effect re-dispersing.

Meanwhile, stirring the solution 300 can be generally expected to bring about an effect of suppressing sedimentation of the particles 350 that are in a dispersed state, in addition to the effect of re-dispersing the particles that have undergone sedimentation as described above.

A stirring operation performed during the liquid droplet discharging operation of FIG. 3 enables liquid droplets to be discharged while sedimentation of the particles 350 is suppressed and a uniformly dispersed state is maintained constantly, making it possible to maintain the concentration of particles to be contained in the liquid droplets constant over time.

However, when the first and second liquid sucking/ejecting members 201 and 202 are operated alternately as illustrated in FIG. 7A and FIG. 7B, the liquid surface of the solution 300 in the liquid retaining section 1 rises as described above, to increase the water pressure applied to the nozzle plate 3 and increase the fall velocity of the liquid droplets 310 to be discharged. This is non-problematic in the case of continuously discharging the liquid droplets 310 to a single position. However, in the case of locating the liquid droplets 310 at equal intervals, generally, the discharging operation is performed at a constant period while the liquid droplet discharging unit 100 or the liquid retaining section 1 configured to locate the liquid droplets is moved at a constant velocity. Therefore, if the fall velocity of the liquid droplets 310 fluctuates, the liquid droplets 310 may land on wrong positions, making the intervals between the liquid droplets 310 non-uniform on the liquid retaining section 1.

It is possible to stir the solution 300 while maintaining the liquid amount in the liquid retaining section 1 constant as illustrated in FIG. 4A to FIG. 4C, by performing an ejecting operation of the second liquid sucking/ejecting member 202 in synchronization with a sucking operation of the first liquid sucking/ejecting member 201 and performing an ejecting operation of the first liquid sucking/ejecting member 201 in synchronization with a sucking operation of the second liquid sucking/ejecting member 202 and setting the first and second liquid sucking/ejecting members to the same sucking velocity, the same ejecting velocity, the same liquid sucking amount, and the same liquid ejecting amount. With this operation, the fall velocity of the liquid droplets does not fluctuate even when the discharging operation is performed while the particles 350 contained in the solution 300 in the liquid retaining section 1 are maintained in the uniformly dispersed state, making it possible to discharge liquid droplets at a constant fall velocity with a constant concentration of particles contained.

Figure 8A:
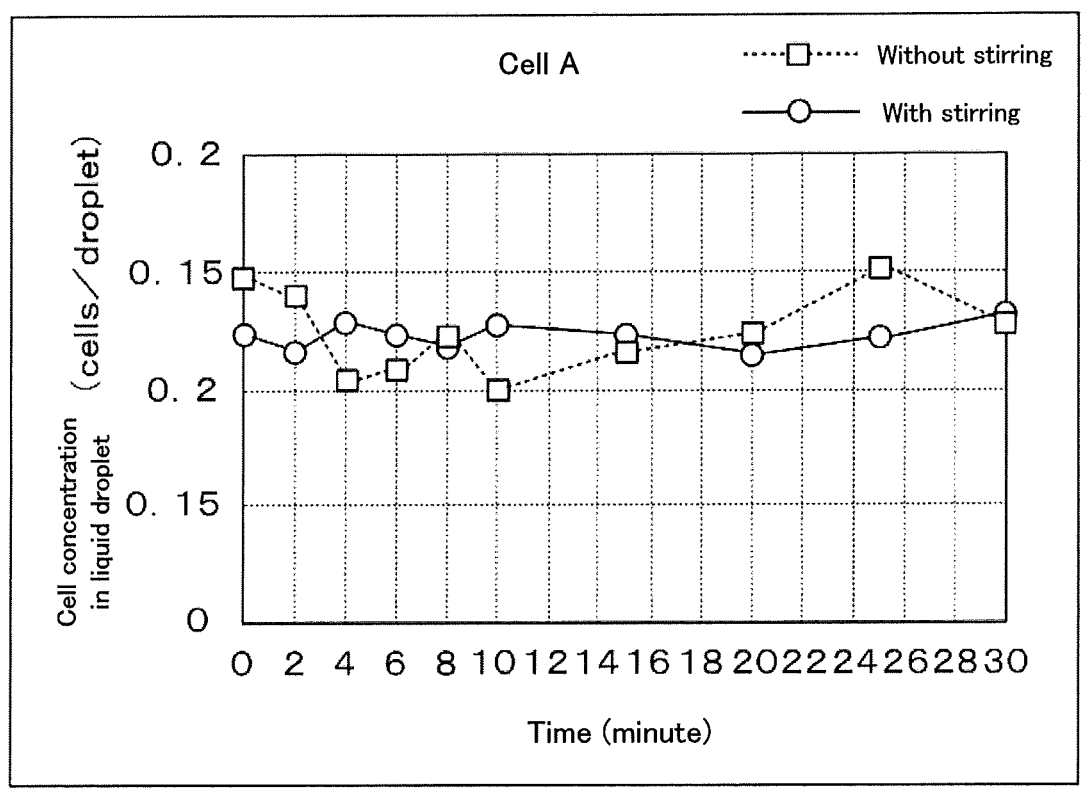
FIG. 8A is a graph plotting results of evaluation of cell concentrations in discharged liquid droplets, depending on presence or absence of a stirring operation in solutions having different cell concentrations.
Figure 8B:
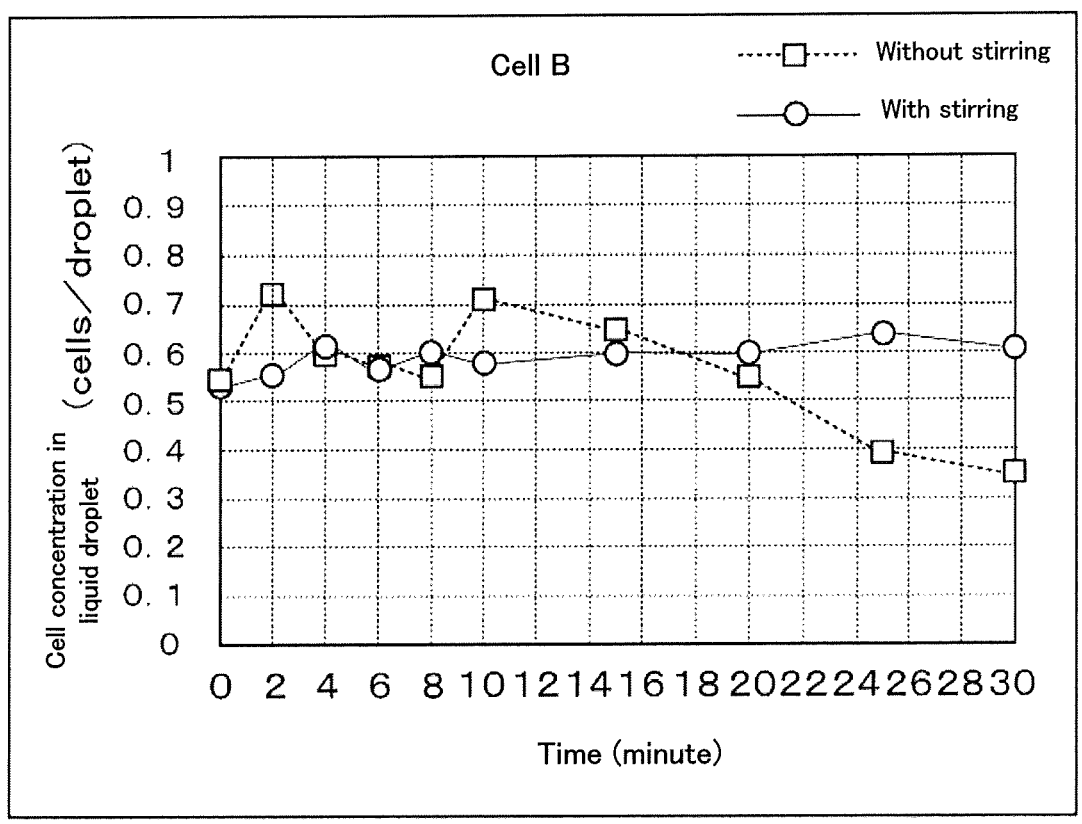
FIG. 8B is a graph plotting results of evaluation of cell concentrations in discharged liquid droplets, depending on presence or absence of a stirring operation in solutions having different cell concentrations.

In this regard, FIG. 8A and FIG. 8B plot an example of results of evaluation of cell concentrations in discharged liquid droplets, depending on presence or absence of a stirring operation in solutions containing different kinds of cells and having different cell concentrations. From the results in FIG. 8A and FIG. 8B, when a stirring operation is absent (dotted-line graph), the cell concentration in discharged liquid droplets rises or falls over time and is not constant. As compared, when a stirring operation is present (solid bold line graph), liquid droplets can be discharged with a constant cell concentration regardless of time elapse. For example, when the liquid amount of the solution 300 in the liquid retaining section 1 is high, when the particle diameter of the particles 350 contained in the solution 300 is large, or when the content concentration of the particles is high, the liquid stirring amount, the sucking velocity, or the ejecting velocity of the first and second liquid sucking/ejecting members 201 and 202 better be high in order to disperse the particles uniformly. On the other hand, when the particles 350 contained are particles that may be damaged by impacts, such as animal cells, the liquid stirring amount, the sucking velocity, or the ejecting velocity better be as low as possible, and the stirring frequency better be low.

Further, the liquid stirring amount, the sucking velocity, or the ejecting velocity needed varies from the case of re-dispersing the particles from the complete sedimentation state of the particles 350 as in FIG. 4A to the case of suppressing sedimentation of the particles 350 that are in a dispersed state as described above. A higher liquid stirring amount, a higher sucking velocity, or a higher ejecting velocity is needed in the former case.

As described above, the liquid stirring amount, the sucking velocity, or the ejecting velocity needed varies depending on, for example, the amount of the solution 300, the kind or concentration of the particles 350, or the sedimentation state. Therefore, it is preferable that the liquid stirring amount, the sucking velocity, or the ejecting velocity be switchable.

Embodiment 5A

—Optical Detection Method—

Figure 9:
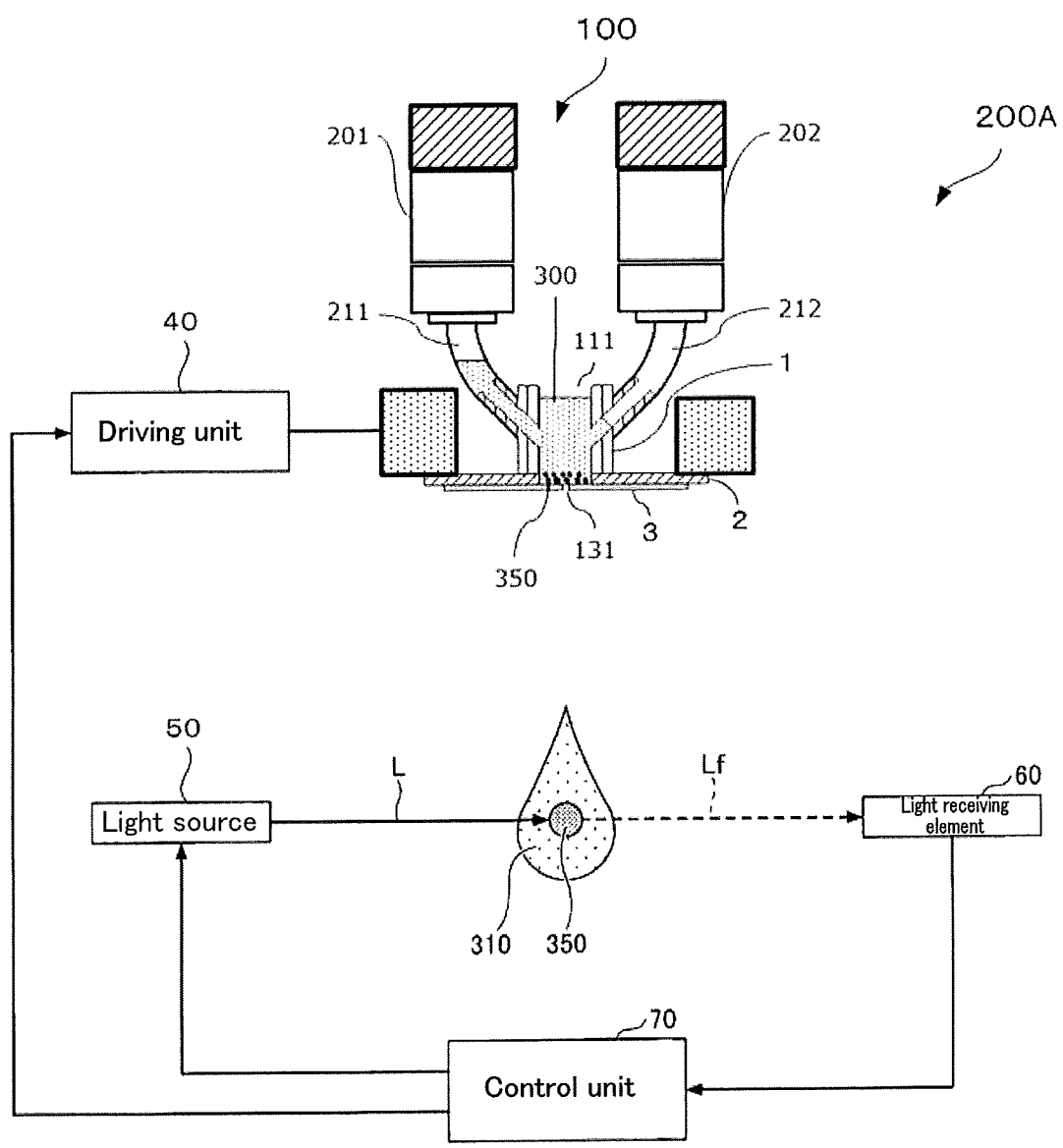
FIG. 9 is an exemplary diagram illustrating an example of a liquid droplet forming device.
Figure 13:
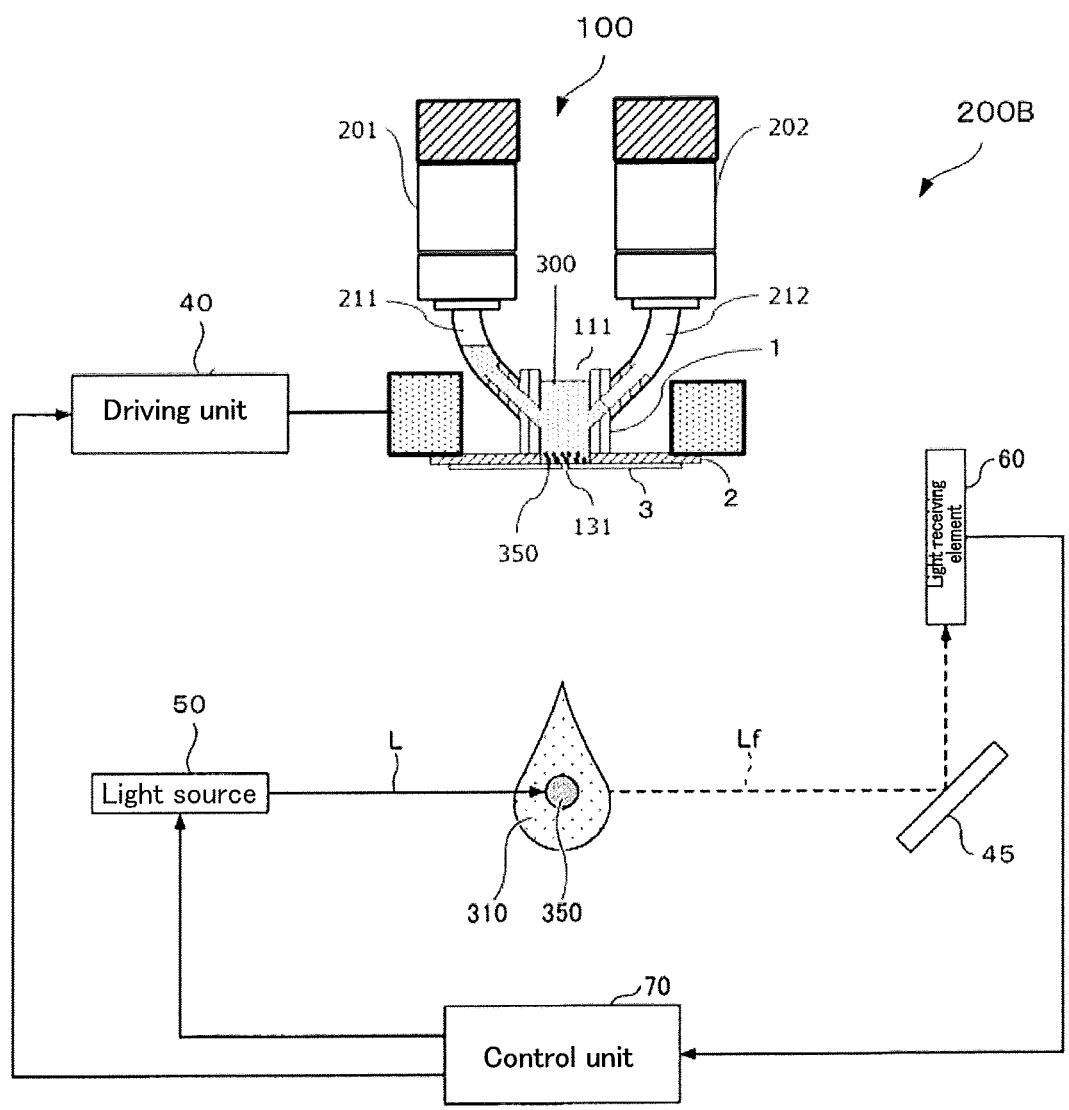
FIG. 13 is a diagram illustrating a modified example of a liquid droplet forming device of FIG. 9.
Figure 14:
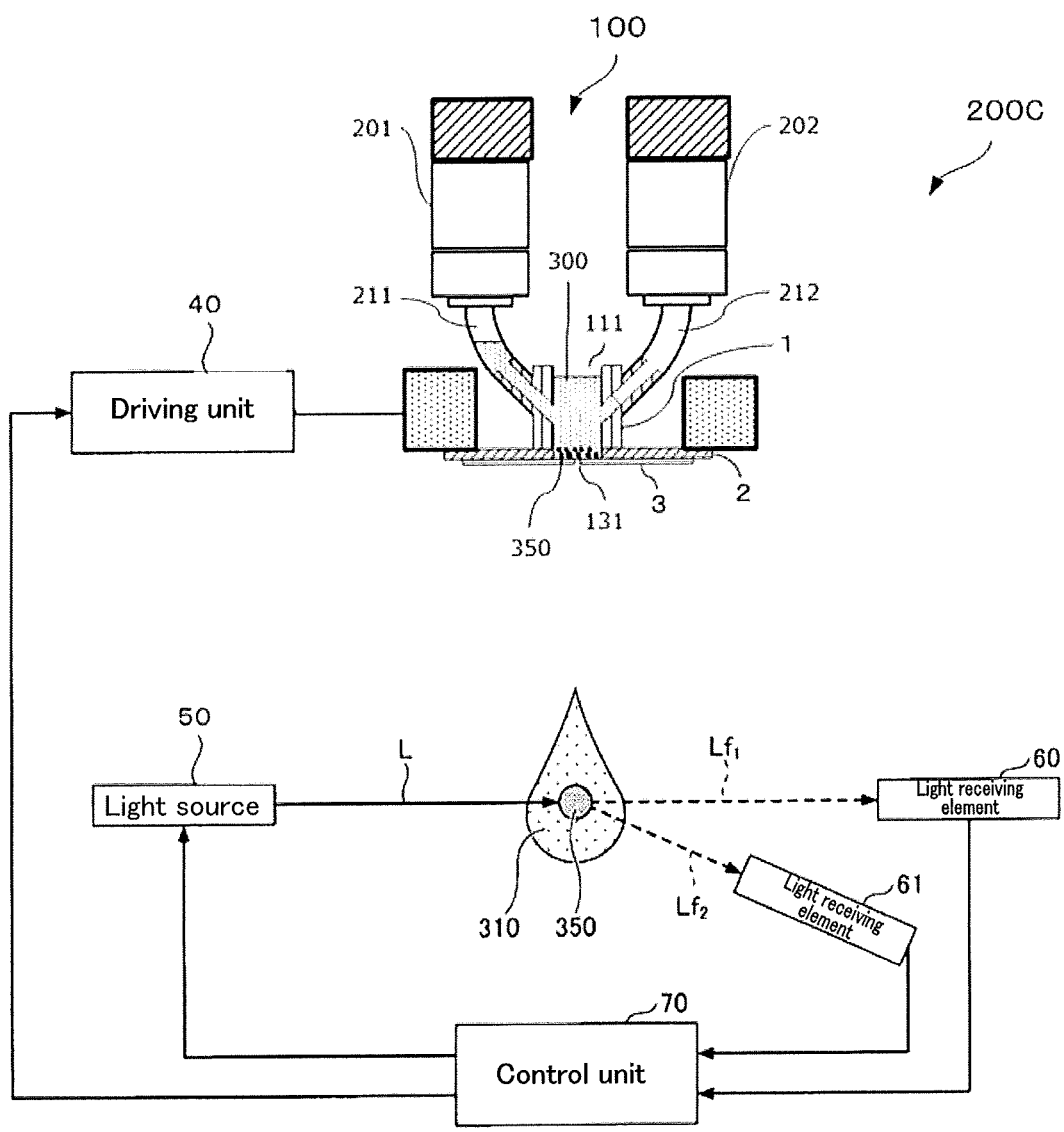
FIG. 14 is a diagram illustrating another modified example of a liquid droplet forming device of FIG. 9.

With reference to FIG. 9, FIG. 13, and FIG. 14, an optical detection method will be described below.

FIG. 9 is an exemplary diagram illustrating an example of the liquid droplet forming device. FIG. 13 and FIG. 14 are exemplary diagrams illustrating other examples of the liquid droplet forming device.

As illustrated in FIG. 9, the liquid droplet forming device 200A includes a liquid droplet discharging unit 100, a driving unit 40, a light source 50, a light receiving element 60, and a control unit 70. The liquid droplet discharging unit 100 is the same as in the embodiment 1.

In FIG. 9, a liquid obtained by dispersing cells in a predetermined solution after fluorescently staining the cells with a specific pigment is used as the cell suspension. Cells are counted by irradiating the liquid droplets 310 formed by the liquid droplet discharging unit 100 with light L having a specific wavelength and emitted from the light source 50 and detecting fluorescence emitted by the cells with the light receiving element 60. Here, autofluorescence emitted by molecules originally contained in the cells may be utilized, in addition to the method of staining the cells with a fluorescent pigment. Alternatively, genes for producing fluorescent proteins (for example, GFP (Green Fluorescent Proteins)) may be previously introduced into the cells, in order that the cells may emit fluorescence.

The light source 50 is configured to irradiate a flying liquid droplet 310 with light L. A flying state means a state from when the liquid droplet 310 is discharged from the liquid droplet discharging unit 100 until when the liquid droplet 310 lands on the landing target. A flying liquid droplet 310 has an approximately spherical shape at the position at which the liquid droplet 310 is irradiated with the light L. The beam shape of the light L is an approximately circular shape.

It is preferable that the beam diameter of the light L be from about 10 times through 100 times as great as the diameter of the liquid droplet 310. This is for ensuring that the liquid droplet 310 is irradiated with the light L from the light source 50 without fail even when the position of the liquid droplet 310 fluctuates.

However, it is not preferable if the beam diameter of the light L is much greater than 100 times as great as the diameter of the liquid droplet 310. This is because the energy density of the light with which the liquid droplet 310 is irradiated is reduced, to lower the light volume of fluorescence Lf to be emitted upon the light L serving as excitation light, making it difficult for the light receiving element 60 to detect the fluorescence Lf.

It is preferable that the light L emitted by the light source 50 be pulse light. It is preferable to use, for example, a solid-state laser, a semiconductor laser, and a dye laser. When the light L is pulse light, the pulse width is preferably 10 microseconds or less and more preferably 1 microsecond or less. The energy per unit pulse is preferably roughly 0.1 microjoules or higher and more preferably 1 microjoule or higher, although significantly depending on the optical system such as presence or absence of light condensation.

The light receiving element 60 is configured to receive fluorescence Lf emitted by a fluorescent-stained cell 350 upon absorption of the light L as excitation light, when the fluorescent-stained cell 350 is contained in a flying liquid droplet 310. Because the fluorescence Lf is emitted to all directions from the fluorescent-stained cell 350, the light receiving element 60 can be disposed at an arbitrary position at which the fluorescence Lf is receivable. Here, in order to improve contrast, it is preferable to dispose the light receiving element 60 at a position at which direct incidence of the light L emitted by the light source 50 to the light receiving element 60 does not occur.

The light receiving element 60 is not particularly limited and may be appropriately selected depending on the intended purpose so long as the light receiving element 60 is an element capable of receiving the fluorescence Lf emitted by the fluorescent-stained cell 350. An optical sensor configured to receive fluorescence from a cell in a liquid droplet when the liquid droplet is irradiated with light having a specific wavelength is preferable.

Examples of the light receiving element 60 include one-dimensional elements such as a photodiode and a photosensor. When high-sensitivity measurement is needed, it is preferable to use a photomultiplier tube and an Avalanche photodiode. As the light receiving element 60, two-dimensional elements such as a CCD (Charge Coupled Device), a CMOS (Complementary Metal Oxide Semiconductor), and a gate CCD may be used.

The fluorescence Lf emitted by the fluorescent-stained cell 350 is weaker than the light L emitted by the light source 50. Therefore, a filter configured to attenuate the wavelength range of the light L may be installed at a preceding stage (light receiving surface side) of the light receiving element 60. This enables the light receiving element 60 to obtain an extremely highly contrastive image of the fluorescent-stained cell 350. As the filter, for example, a notch filter configured to attenuate a specific wavelength range including the wavelength of the light L may be used.

As described above, it is preferable that the light L emitted by the light source 50 be pulse light. However, the light L emitted by the light source 50 may be continuously oscillating light. In this case, it is preferable to control the light receiving element 60 to be capable of receiving light at a timing at which a flying liquid droplet 310 is irradiated with the continuously oscillating light, to make the light receiving element 60 receive the fluorescence Lf.

The control unit 70 has a function of controlling the driving unit 40 and the light source 50. The control unit 70 also has a function of obtaining information that is based on the light volume received by the light receiving element 60 and counting the number of fluorescent-stained cells 350 contained in the liquid droplet 310 (the case where the number is zero is also included).

Figure 10:
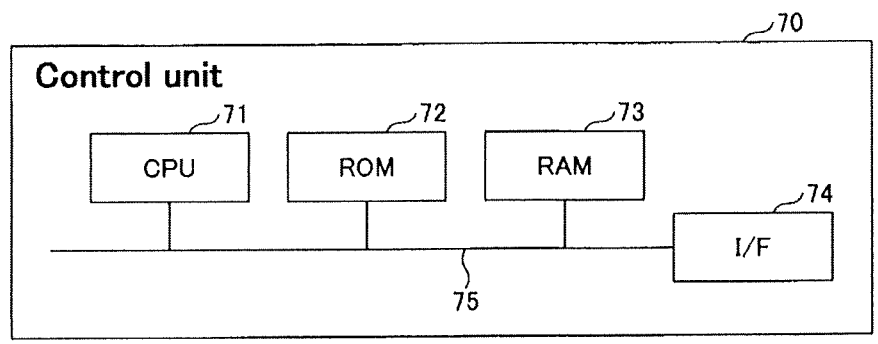
FIG. 10 is a diagram illustrating hardware blocks of a control unit of FIG. 9.
Figure 11:
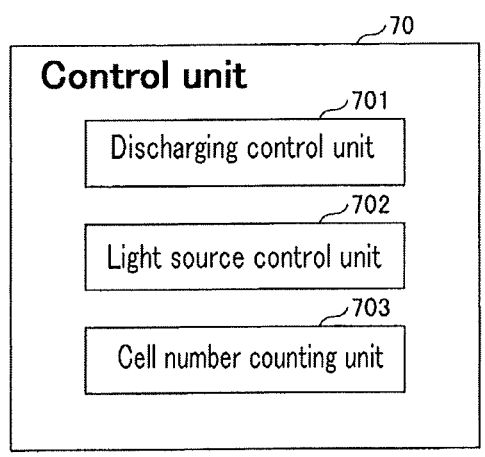
FIG. 11 is a diagram illustrating functional blocks of a control unit of FIG. 9.
Figure 12:
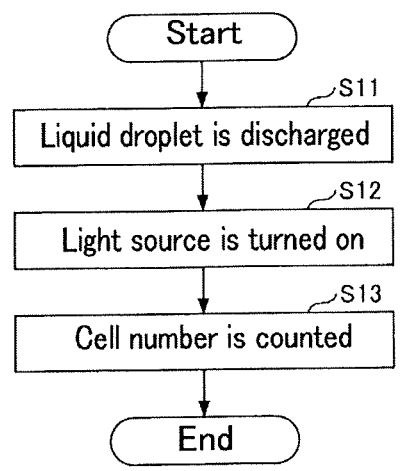
FIG. 12 is a flowchart illustrating an example of an operation of a liquid droplet forming device.

With reference to FIG. 10 to FIG. 12, an operation of the liquid droplet forming device 200A including an operation of the control unit 70 will be described below.

FIG. 10 is a diagram illustrating hardware blocks of the control unit 70 of FIG. 9. FIG. 11 is a diagram illustrating functional blocks of the control unit 70 of FIG. 9. FIG. 12 is a flowchart illustrating an example of the operation of the liquid droplet forming device 200A.

As illustrated in FIG. 10, the control unit 70 includes a CPU 71, a ROM 72, a RAM 73, an I/F 74, and a bus line 75. The CPU 71, the ROM 72, the RAM 73, and the I/F 74 are coupled to one another via the bus line 75.

The CPU 71 is configured to control various functions of the control unit 70. The ROM 72 serving as a memory unit is configured to store programs to be executed by the CPU 71 for controlling the various functions of the control unit 70 and various information. The RAM 73 serving as a memory unit is configured to be used as, for example, the work area of the CPU 71. The RAM 73 is also configured to be capable of storing predetermined information for a temporary period of time. The I/F 74 is an interface configured to couple the liquid droplet forming device 200A to, for example, another device. The liquid droplet forming device 200A may be coupled to, for example, an external network via the I/F 74.

As illustrated in FIG. 11, the control unit 70 includes a discharging control unit 701, a light source control unit 702, and a cell number counting unit (cell number sensing unit) 703 as functional blocks.

With reference to FIG. 11 and FIG. 12, particle number counting by the liquid droplet forming device 200A will be described.

In the step S11, the discharging control unit 701 of the control unit 70 outputs an instruction for discharging to the driving unit 40. Upon reception of the instruction for discharging from the discharging control unit 701, the driving unit 40 supplies a driving signal to the vibration member 2 to vibrate the nozzle plate 3. The vibration of the nozzle plate 3 causes a liquid droplet 310 containing a fluorescent-stained cell 350 to be discharged through the nozzle 131.

Next, in the step S12, the light source control unit 702 of the control unit 70 outputs an instruction for lighting to the light source 50 in synchronization with the discharging of the liquid droplet 310 (in synchronization with a driving signal supplied by the driving unit 40 to the liquid droplet discharging unit 100). In accordance with this instruction, the light source 50 is turned on to irradiate the flying liquid droplet 310 with the light L.

Here, the light is emitted by the light source 50, not in synchronization with discharging of the liquid droplet 310 by the liquid droplet discharging unit 100 (supplying of the driving signal to the liquid droplet discharging unit 100 by the driving unit 40), but in synchronization with the timing at which the liquid droplet 310 has come flying to a predetermined position in order for the liquid droplet 310 to be irradiated with the light L. That is, the light source control unit 702 controls the light source 50 to emit light at a predetermined period of time of delay from the discharging of the liquid droplet 310 by the liquid droplet discharging unit 100 (from the driving signal supplied by the driving unit 40 to the liquid droplet discharging unit 100).

For example, the velocity v of the liquid droplet 310 to be discharged when the driving signal is supplied to the liquid droplet discharging unit 100 may be measured beforehand. Based on the measured velocity v, the time t taken from when the liquid droplet 310 is discharged until when the liquid droplet 310 reaches the predetermined position may be calculated, in order that the timing of light irradiation by the light source 50 may be delayed from the timing at which the driving signal is supplied to the liquid droplet discharging unit 100 by the period of time of t. This enables a good control on light emission, and can ensure that the liquid droplet 310 is irradiated with the light from the light source 50 without fail.

Next, in the step S13, the cell number counting unit 703 of the control unit 70 counts the number of fluorescent-stained cells 350 contained in the liquid droplet 310 (the case where the number is zero is also included) based on information from the light receiving element 60. The information from the light receiving element 60 indicates the luminance (light volume) and the area value of the fluorescent-stained cell 350.

The cell number counting unit 703 can count the number of fluorescent-stained cells 350 by, for example, comparing the light volume received by the light receiving element 60 with a predetermined threshold. In this case, a one-dimensional element may be used or a two-dimensional element may be used as the light receiving element 60.

When a two-dimensional element is used as the light receiving element 60, the cell number counting unit 703 may use a method of performing image processing for calculating the luminance or the area of the fluorescent-stained cell 350 based on a two-dimensional image obtained from the light receiving element 60. In this case, the cell number counting unit 703 can count the number of fluorescent-stained cells 350 by calculating the luminance or the area value of the fluorescent-stained cell 350 by image processing and comparing the calculated luminance or area value with a predetermined threshold.

The fluorescent-stained cell 350 may be a cell or a stained cell. A stained cell means a cell stained with a fluorescent pigment or a cell that can express a fluorescent protein.

In this way, in the liquid droplet forming device 200A, the driving unit 40 supplies a driving signal to the liquid droplet discharging unit 100 retaining the cell suspension 300 suspending fluorescent-stained cells 350 to cause the liquid droplet discharging unit 100 to discharge a liquid droplet 310 containing the fluorescent-stained cell 350, and the flying liquid droplet 310 is irradiated with the light L from the light source 50. Then, the fluorescent-stained cell 350 contained in the flying liquid droplet 310 emits the fluorescence Lf upon the light L serving as excitation light, and the light receiving element 60 receives the fluorescence Lf. Then, the cell number counting unit 703 counts the number of fluorescent-stained cells 350 contained in the flying liquid droplet 310, based on information from the light receiving element 60.

That is, the liquid droplet forming device 200A is configured for on-the-spot actual observation of the number of fluorescent-stained cells 350 contained in the flying liquid droplet 310. This can realize a better accuracy than hitherto obtained, in counting the number of fluorescent-stained cells 350. Moreover, because the fluorescent-stained cell 350 contained in the flying liquid droplet 310 is irradiated with the light L and emits the fluorescence Lf that is to be received by the light receiving element 60, an image of the fluorescent-stained cell 350 can be obtained with a high contrast, and the frequency of occurrence of erroneous counting of the number of fluorescent-stained cells 350 can be reduced.

Embodiment 6A

FIG. 13 is an exemplary diagram illustrating a modified example of the liquid droplet forming device 200A of FIG. 9. As illustrated in FIG. 13, a liquid droplet forming device 200B is different from the liquid droplet forming device 200A (see FIG. 9) in that a mirror 45 is arranged at the preceding stage of the light receiving element 60. Description about components that are the same as in the embodiment already described may be skipped.

In the liquid droplet forming device 200B, arranging the mirror 45 at the perceiving stage of the light receiving element 60 can improve the degree of latitude in the layout of the light receiving element 60.

For example, in the layout of FIG. 9, when a nozzle 131 and a landing target are brought close to each other, there is a risk of occurrence of interference between the landing target and the optical system (particularly, the light receiving element 60) of the liquid droplet forming device 200A. With the layout of FIG. 13, occurrence of interference can be avoided.

That is, by changing the layout of the light receiving element 60 as illustrated in FIG. 13, it is possible to reduce the distance (gap) between the landing target on which a liquid droplet 310 is landed and the nozzle 131 and suppress landing on a wrong position. As a result, the dispensing accuracy can be improved.

Embodiment 7A

FIG. 14 is an exemplary diagram illustrating another modified example of the liquid droplet forming device 200A of FIG. 9. As illustrated in FIG. 14, a liquid droplet forming device 200C is different from the liquid droplet forming device 200A (see FIG. 9) in that a light receiving element 61 configured to receive fluorescence $Lf_2$ emitted by the fluorescent-stained cell 350 is provided in addition to the light receiving element 60 configured to receive fluorescence $Lf_1$ emitted by the fluorescent-stained cell 350. Description about components that are the same as in the embodiment already described may be skipped.

The fluorescences $Lf_1$ and $Lf_2$ represent parts of fluorescence emitted to all directions from the fluorescent-stained cell 350. The light receiving elements 60 and 61 can be disposed at arbitrary positions at which the fluorescence emitted to different directions by the fluorescent-stained cell 350 is receivable. Three or more light receiving elements may be disposed at positions at which the fluorescence emitted to different directions by the fluorescent-stained cell 350 is receivable. The light receiving elements may have the same specifications or different specifications.

With one light receiving element, when a plurality of fluorescent-stained cells 350 are contained in a flying liquid droplet 310, there is a risk that the cell number counting unit 703 may erroneously count the number of fluorescent-stained cells 350 contained in the liquid droplet 310 (a risk that a counting error may occur) because the fluorescent-stained cells 350 may overlap each other.

Figure 15A:
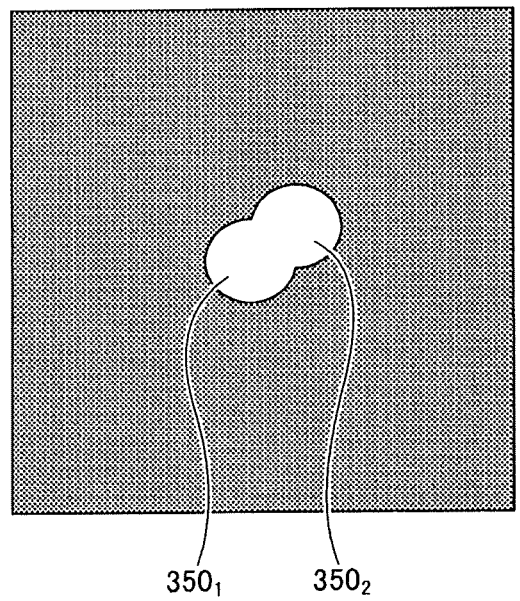
FIG. 15A is a diagram illustrating a case where two fluorescent particles are contained in a flying liquid droplet.
Figure 15B:
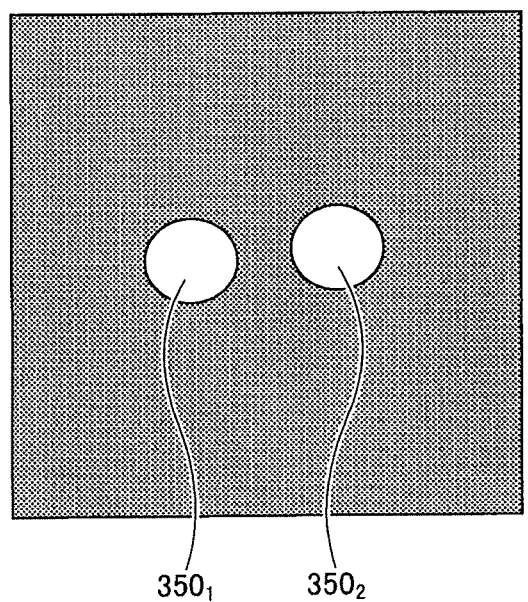
FIG. 15B is a diagram illustrating a case where two fluorescent particles are contained in a flying liquid droplet.

FIG. 15A and FIG. 15B are diagrams illustrating a case where two fluorescent-stained cells are contained in a flying liquid droplet. For example, as illustrated in FIG. 15A, there may be a case where fluorescent-stained cells $350_1$ and $350_2$ overlap each other, or as illustrated in FIG. 15B, there may be a case where the fluorescent-stained cells $350_1$ and $350_2$ do not overlap each other. By providing two or more light receiving elements, it is possible to reduce the influence of overlap of the fluorescent-stained cells.

As described above, the cell number counting unit 703 can count the number of fluorescent particles, by calculating the luminance or the area value of fluorescent particles by image processing and comparing the calculated luminance or area value with a predetermined threshold.

When two or more light receiving elements are installed, it is possible to suppress occurrence of a counting error, by adopting the data indicating the maximum value among the luminance values or area values obtained from these light receiving elements. This will be described in more detail with reference to FIG. 16.

Figure 16:
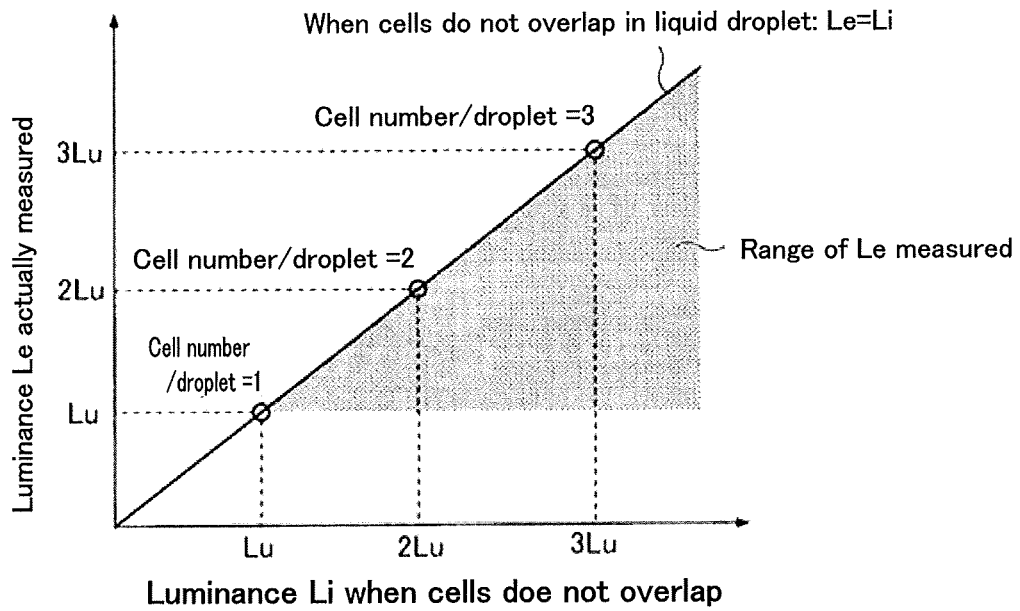
FIG. 16 a graph plotting an example of a relationship between a luminance Li when particles do not overlap each other and a luminance Le actually measured.

FIG. 16 is a graph plotting an example of a relationship between a luminance Li when particles do not overlap each other and a luminance Le actually measured. As plotted in FIG. 16, when particles in the liquid droplet do not overlap each other, Le is equal to Li. For example, in the case where the luminance of one cell is assumed to be Lu, Le is equal to Lu when the number of cells per droplet is 1, and Le is equal to nLu when the number of particles per droplet is n (n: natural number).

However, actually, when n is 2 or greater, because particles may overlap each other, the luminance to be actually measured is $Lu \leq Le \leq nLu$ (the half-tone dot meshed portion in FIG. 16). Hence, when the number of cells per droplet is n, the threshold may be set to, for example, $(nLu-Lu/2) \leq threshold < (nLu+Lu/2)$. When a plurality of light receiving elements are installed, it is possible to suppress occurrence of a counting error, by adopting the maximum value among the data obtained from these light receiving elements. An area value may be used instead of luminance.

When a plurality of light receiving elements are installed, the number of particles may be determined according to an algorithm for estimating the number of cells based on a plurality of shape data to be obtained.

As can be understood, with the plurality of light receiving elements configured to receive fluorescence emitted to different directions by the fluorescent-stained cell 350, the liquid droplet forming device 200C can further reduce the frequency of occurrence of erroneous counting of the number of fluorescent-stained cells 350.

Embodiment 8A

—Electric or Magnetic Detection Method—

Figure 17:
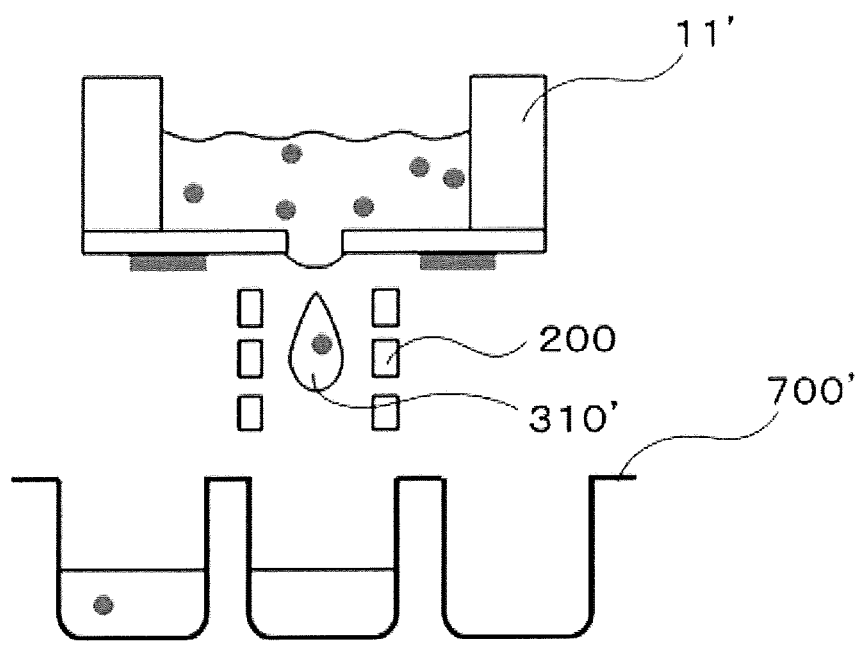
FIG. 17 is a diagram illustrating another modified example of a liquid droplet forming device of FIG. 9.

In the case of the electric or magnetic detection method, as illustrated in FIG. 17, a coil 200 configured to count the number of cells is installed as a sensor immediately below a discharging head configured to discharge the cell suspension onto a plate 700' from a liquid chamber 11' in the form of a liquid droplet 310'. Cells are coated with magnetic beads that are modified with a specific protein and can adhere to the cells. Therefore, when the cells to which magnetic beads adhere pass through the coil, an induced current is generated to enable detection of presence or absence of the cells in the flying liquid droplet. Generally, cells have proteins specific to the cells on the surfaces of the cells. Modification of magnetic beads with antibodies that can adhere to the proteins enables adhesion of the magnetic beads to the cells.

As such magnetic beads, a ready-made product can be used. For example, DYNABEADS (registered trademark) available from Veritas Corporation can be used.

Embodiment 9A

—Operation for Observing Cells Before Discharging—

Figure 18:
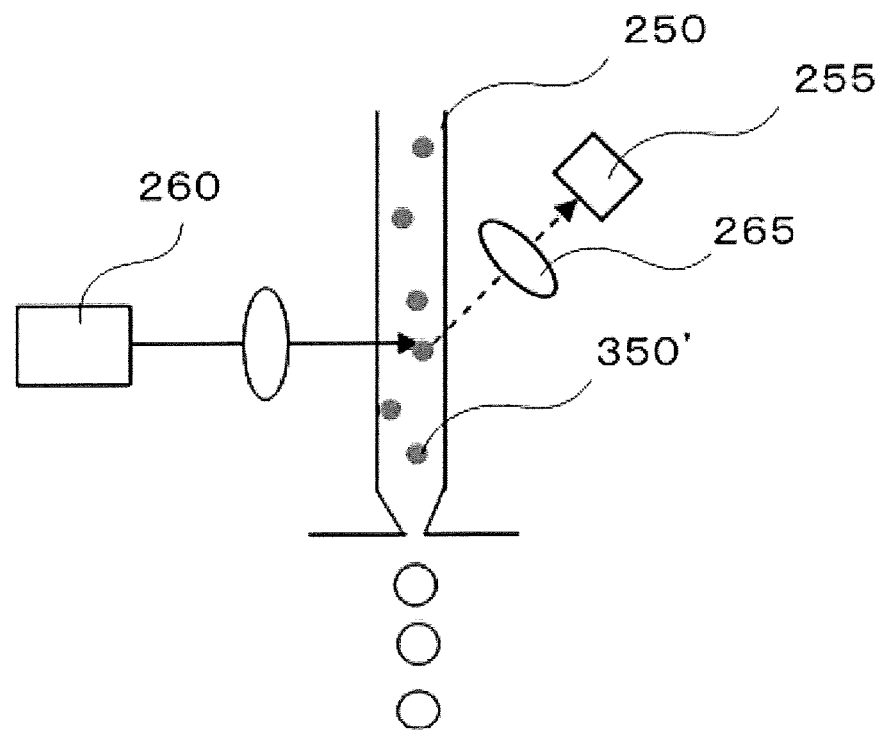
FIG. 18 is a diagram illustrating an example of a method for counting cells that have passed through a micro-flow path.
Figure 19:
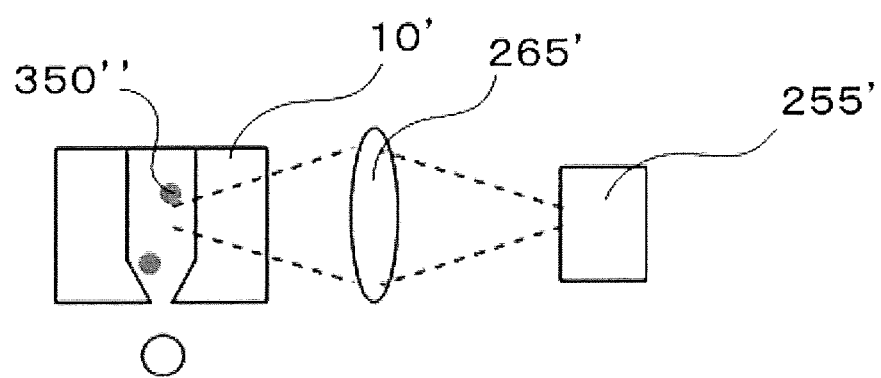
FIG. 19 is a diagram illustrating an example of a method for capturing an image of a portion near a nozzle portion of a discharging head.

The operation for observing cells before discharging may be performed by, for example, a method for counting cells 350' that have passed through a micro-flow path 250 illustrated in FIG. 18 or a method for capturing an image of a portion near a nozzle portion of a liquid droplet discharging unit illustrated in FIG. 19.

The method of FIG. 18 is a method used in a cell sorter device, and, for example, CELL SORTER SH800 available from Sony Corporation can be used. In FIG. 18, a light source 260 emits laser light into the micro-flow path 250, and a detector 255 detects scattered light or fluorescence through a condenser lens 265. This enables discrimination of presence or absence of cells or the kind of the cells, while a liquid droplet is being formed. Based on the number of cells that have passed through the micro-flow path 250, this method enables estimation of the number of cells that have landed in a predetermined well.

As the discharging head 10' illustrated in FIG. 19, a single cell printer available from Cytena GmbH can be used. In FIG. 19, it is possible to estimate the number of cells that have landed in a predetermined well, by capturing an image of the portion near the nozzle portion with an image capturing unit 255' through a lens 265' before discharging and estimating based on the captured image that cells 350" present near the nozzle portion have been discharged, or by estimating the number of cells that are considered to have been discharged based on a difference between images captured before and after discharging.

The method of FIG. 19 is more preferable because the method enables on-demand liquid droplet formation, whereas the method of FIG. 18 for counting cells that have passed through the micro-flow path generates liquid droplets continuously.

Embodiment 10A

—Operation for Counting Cells after Landing—

The operation for counting cells after landing may be performed by a method for detecting fluorescent-stained cells by observing the wells in the plate with, for example, a fluorescence microscope. This method is described in, for example, Sangjun et al., PLoS One, Volume 6(3), e17455.

Methods for observing cells before discharging a liquid droplet or after landing have the problems described below. Depending on the kind of the plate to be produced, it is the most preferable to observe cells in a liquid droplet that is being discharged. In the method for observing cells before discharging, the number of cells that are considered to have landed is counted based on the number of cells that have passed through a flow path and image observation before discharging (and after discharging). Therefore, it is not confirmed whether the cells have actually been discharged, and an unexpected error may occur. For example, there may be a case where because the nozzle portion is stained, a liquid droplet is not discharged appropriately but adheres to the nozzle plate, thus failing to make the cells in the liquid droplet land. Moreover, there may occur a problem that the cells stay behind in a narrow region of the nozzle portion, or a discharging operation causes the cells to move beyond assumption and go outside the range of observation. The method for detecting cells on the plate after landing also have problems.

First, there is a need for preparing a plate that can be observed with a microscope. As a plate that can be observed, it is common to use a plate having a transparent, flat bottom surface, particularly a plate having a bottom surface formed of glass. However, there is a problem that such a special plate is incompatible with use of ordinary wells. Further, when the number of cells is large, such as some tens of cells, there is a problem that correct counting is impossible because the cells may overlap with each other. Accordingly, it is preferable to perform the operation for observing cells before discharging and the operation for counting cells after landing, in addition to counting the number of cells contained in a liquid droplet with a sensor and a particle number (cell number) counting unit after the liquid droplet is discharged and before the liquid droplet lands in a well.

As the light receiving element, a light receiving element including one or a small number of light receiving portion(s), such as a photodiode, an Avalanche photodiode, and a photomultiplier tube may be used. In addition, a two-dimensional sensor including light receiving elements in a two-dimensional array formation, such as a CCD (Charge Coupled Device), a CMOS (Complementary Metal Oxide Semiconductor), and a gate CCD may be used.

When using a light receiving element including one or a small number of light receiving portion(s), it is conceivable to determine the number of cells contained, based on the fluorescence intensity, using a calibration curve prepared beforehand. Here, binary detection of whether cells are present or absent in a flying liquid droplet is common. When the cell suspension is discharged in a state that the cell concentration is so sufficiently low that almost only 1 or 0 cell(s) will be contained in a liquid droplet, sufficiently accurate counting is available by the binary detection. On the premise that cells are randomly distributed in the cell suspension, the cell number in a flying liquid droplet is considered to conform to a Poisson distribution, and the probability P (>2) at which two or more cells are contained in a liquid droplet is represented by a formula (1) below.

Figure 20:
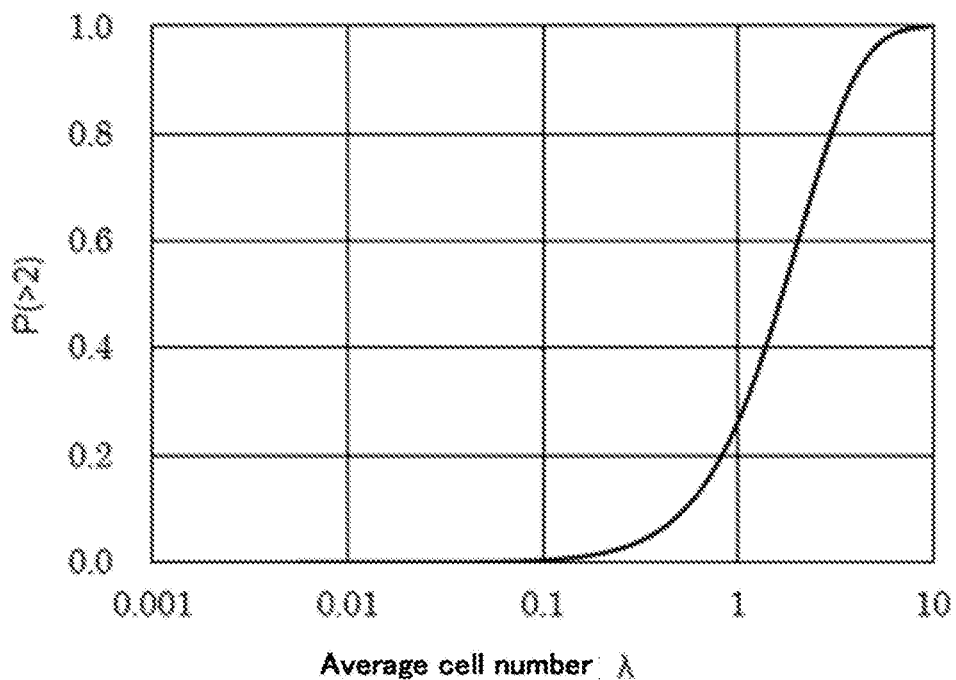
FIG. 20 is a graph plotting a relationship between a probability P (>2) and an average cell number.

FIG. 20 is a graph plotting a relationship between the probability P (>2) and an average cell number. Here, X is a value representing an average cell number in a liquid droplet and obtained by multiplying the cell concentration in the cell suspension by the volume of a liquid droplet discharged.

$$P(>2)=1-(1+\lambda)\times e^{-\lambda} \quad \text{formula (1)}$$

When performing cell number counting by binary detection, in order to ensure accuracy, it is preferable that the probability P (>2) be a sufficiently low value, and that λ satisfy: λ<0.15, at which the probability P (>2) is 1% or lower.

The light source is not particularly limited and may be appropriately selected depending on the intended purpose, so long as the light source can excite fluorescence from cells. It is possible to use, for example, an ordinary lamp such as a mercury lamp and a halogen lamp to which a filter is applied for emission of a specific wavelength, a LED (Light Emitting Diode), and a laser. However, particularly when forming a minute liquid droplet of 1 nL or less, there is a need for irradiating a small region with a high light intensity. Therefore, use of a laser is preferable.

As a laser light source, various commonly known lasers such as a solid-state laser, a gas laser, and a semiconductor laser can be used. The excitation light source may be a light source that is configured to continuously irradiate a region through which a liquid droplet passes or may be a light source that is configured for pulsed irradiation in synchronization with discharging of a liquid droplet at a timing delayed by a predetermined period of time from the operation for discharging the liquid droplet.

Embodiment 1B

A liquid droplet forming device according to an embodiment 1B includes a liquid droplet discharging unit including: a liquid droplet discharging port; a liquid retaining section including the liquid droplet discharging port; first and second liquid sucking/ejecting members configured to suck and eject a liquid in the liquid retaining section; a first tube linking the liquid retaining section to the first liquid sucking/ejecting member; and a second tube linking the liquid retaining section to the second liquid sucking/ejecting member, wherein the maximum liquid sucking amounts of the first and second liquid sucking/ejecting members are lower than the volumes of the first tube and the second tube respectively.

The liquid droplet forming device according to the embodiment 1B is the same as the liquid droplet forming device according to the embodiment 1A except for the following point.

In FIG. 2, the maximum liquid sucking amounts of the first liquid sucking/ejecting member 201 and the second liquid sucking/ejecting member 202 are adjusted to be lower than the volumes of the first tube 211 and the second tube 212 respectively. This makes it possible for the liquid that is being stirred in the liquid retaining section to be adjusted so as not to enter the first and second liquid sucking/ejecting members. This eliminates the need for washing the interior of the first and second liquid sucking/ejecting members or replacing the first and second liquid sucking/ejecting members each time the kind of the discharging target is changed.

The first tube 211 and the second tube 212 are disposed to be inclined with respect to the nozzles 131 (nozzle plate 3). That is, the tubes are disposed to be inclined with respect to the center axis passing through the nozzles 131.

As the disposition of the first tube 211 and the second tube 212, it is preferable to dispose the tubes in a manner that an extension line of the center axis of each tube at the linking portion falls on a corner portion formed by the nozzle plate 3 and the vibration member 2, or is slightly off from the corner portion toward the nozzles 131.

Embodiment 1C

A liquid droplet forming device according to an embodiment 1C includes a liquid droplet discharging unit including: a discharging port; a liquid retaining section including the discharging port; and a sucking/ejecting member configured to suck and eject a liquid in the liquid retaining section, wherein the liquid droplet discharging unit is configured to perform sucking/ejecting operations while varying an ejecting velocity of the sucking/ejecting member.

FIG. 21A to FIG. 21F are diagrams depicting a liquid stirring operation of the liquid droplet forming device 200 according to the embodiment 1C using the first and second sucking/ejecting members 201 and 202. The liquid droplet forming device 200 according to the embodiment 1C is the same as the liquid droplet forming device 200 according to the embodiment 1A except for the following point. Therefore, description about components that are the same as the components already described in the liquid droplet forming device according to the embodiment 1A will be skipped.

Figure 21A:
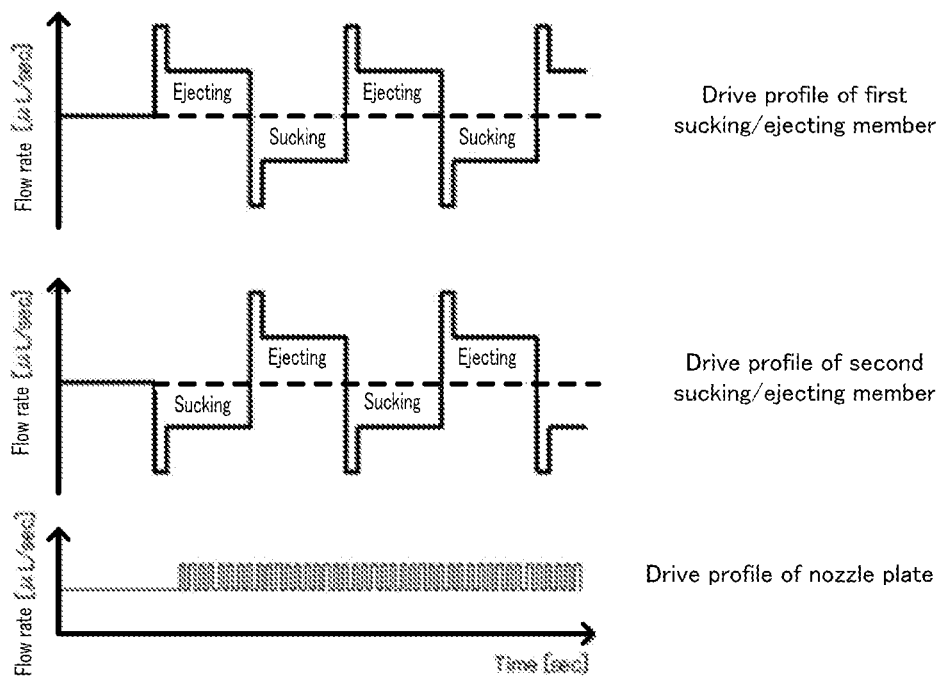
FIG. 21A is a diagram illustrating an example depicting drive profiles of first and second sucking/ejecting members of a liquid droplet forming device according to an embodiment 1C.

FIG. 21A plots the drive profiles of the first and second sucking/ejecting members 201 and 202 and the drive profile of the nozzle plate 3 by representing time [sec] on the horizontal axis and discharging flow rate [microliter/sec] on the vertical axis.

The first sucking/ejecting member 201 performs an ejecting operation first. Here, a primary ejecting operation for swirling up the particles is performed, and then a secondary ejecting operation for suppressing sedimentation of the particles over time is performed. Subsequent to the first ejecting operation, a sucking operation is performed. Here, likewise, a primary sucking operation for swirling up the particles is performed, and then a secondary sucking operation for suppressing sedimentation of the particles over time is performed. As plotted in FIG. 21A where the described ejecting operation and sucking operation constitute one cycle, the first sucking/ejecting member 201 repeatedly performs the ejecting operation and the sucking operation continuously, to perform the stirring operation constantly.

The second sucking/ejecting member 202 performs a sucking operation first. Here, a primary sucking operation for swirling up the particles is performed, and then a secondary sucking operation for suppressing sedimentation of the particles over time is performed. Subsequent to the first sucking operation, an ejecting operation is performed. Here, likewise, a primary ejecting operation for swirling up the particles is performed, and then a secondary ejecting operation for suppressing sedimentation of the particles over time is performed. As plotted in FIG. 21A where the described sucking operation and ejecting operation constitute one cycle, the second sucking/ejecting member 202 repeatedly performs the sucking operation and the ejecting operation continuously, to perform the stirring operation constantly.

Further, while the first and second sucking/ejecting members 201 and 202 are performing the stirring operation constantly, the nozzle plate 3 is vibrated to cause the nozzles 131 to vibrate and discharge the solution 300 in the liquid retaining section 1 in the form of liquid droplets 310. Vibration of the nozzle plate 3 (i.e., discharge of the liquid droplets 310) is started after the primary ejecting operation is terminated in the first sucking or ejecting operation of the first and second sucking/ejecting members 201 and 202.

In order to continue discharging particles at a stable concentration, the first and second sucking/ejecting members 201 and 202 perform the stirring operation in the liquid retaining section 1 constantly. What matters for stabilization of the particle concentration is to perform an ejecting operation or a sucking operation for a long time. The length of a sucking/ejecting operation is determined by the capacity of the liquid retaining section 1, a first flow path 211, and a second flow path 212.

If a sucking/ejecting operation is performed only by the primary ejecting operation (primary flow velocity) for swirling up the particles, the length of time of one cycle is too short to perform a sucking operation for a long time. This gives rise to a need for performing sucking/ejecting operations frequently. On the other hand, only by the secondary ejecting operation (secondary flow velocity) for suppressing sedimentation of the particles over time, the flow velocity is sufficient for suppressing sedimentation, but is energetically weak to swirl up and re-stir the particles. Hence, as described above, the primary ejecting operation for swirling up the particles is performed, and then the secondary ejecting operation for suppressing sedimentation of the particles over time is performed. This enables a long continuous operation with a small amount, and can realize stabilization of the particle concentration.

Figure 21B:
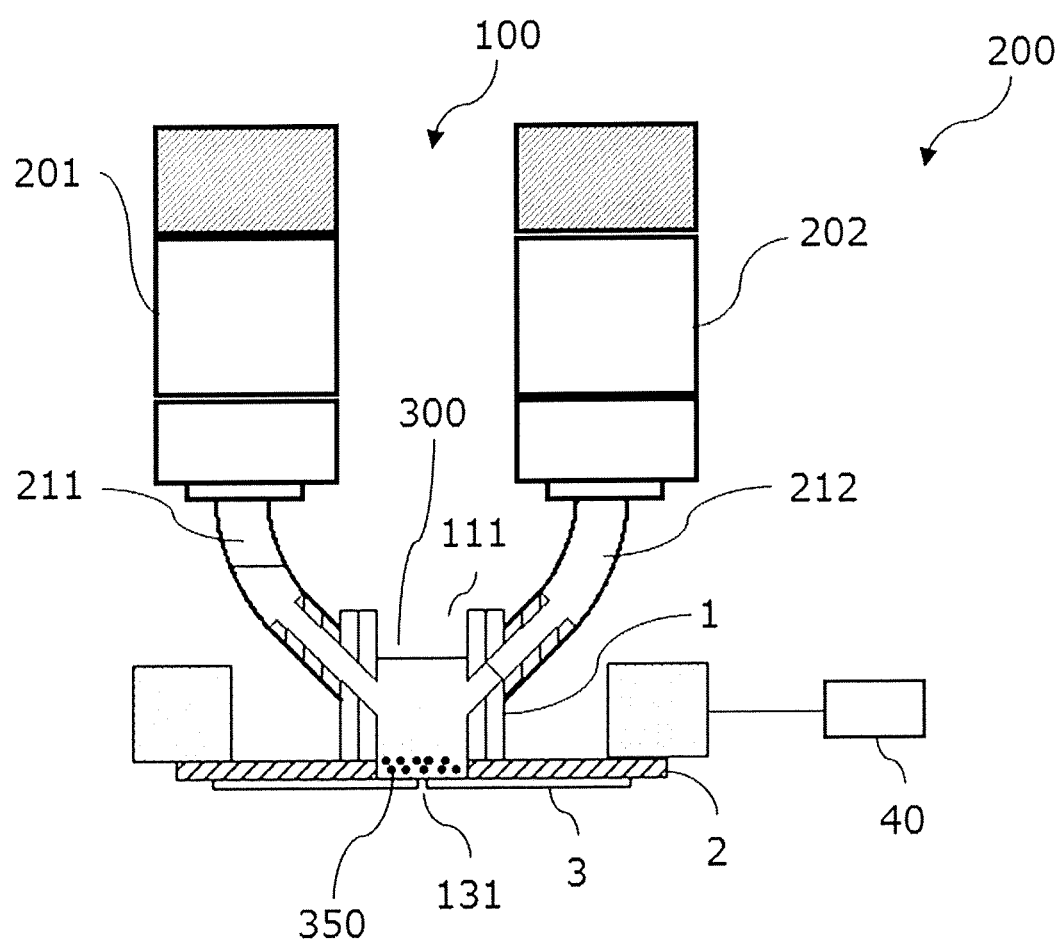
FIG. 21B is a diagram illustrating an example depicting liquid stirring using first and second sucking/ejecting members of a liquid droplet forming device according to the embodiment 1C.

FIG. 21B is a diagram illustrating a state that the solution 300 containing the particles 350 is poured in the liquid retaining section 1 and left to stand still.

The first and second sucking/ejecting members 201 and 202 are in communication with the liquid retaining section 1 through the first flow path 211 and the second flow path 212. The first flow path 211 and the second flow path 212 are disposed to be inclined with respect to the nozzles 131 (or the nozzle plate 3). That is, the flow paths are disposed to be inclined with respect to the center axis passing through the nozzles 131.

As the disposition of the first flow path 211 and the second flow path 212, it is preferable to dispose the two flow paths in a manner that an extension line of the center axis of each flow path at the portion linking to the liquid retaining section 1 falls on a corner portion formed by the nozzle plate 3 and the vibration member 2, or is slightly off from the corner portion toward the nozzles 131.

Examples of the first and second sucking/ejecting members 201 and 202 include a pump capable of sucking, retaining, and ejecting a constant amount of a liquid, such as syringe-type and plunger-type motor pumps.

Due to free sedimentation of the particles 350, the particles 350 are in the state of having undergone sedimentation and accumulated on the bottom of the liquid retaining section 1. If a discharging waveform is input from the driving unit 40 and a liquid droplet discharging operation is performed while in this state in which the particles 350 have aggregated near the nozzles 131, the aggregated particles 350 may clog the nozzles 131, resulting in the problem of discharging failure in which no liquid droplets are formed.

Even if liquid droplets can be formed, liquid droplets formed initially are discharged in a state of containing particles 350 in a large amount, and the content of particles 350 in the liquid droplets gradually decreases. When the particles 350 above the nozzles have been discharged, only the supernatant will be discharged, resulting in the problem of a large variation in the content of particles 350 in the liquid droplets over time.

As illustrated in FIG. 21B, any one of the first and second sucking/ejecting members 201 and 202 performs a previous sucking operation to put the interior of the first flow path 211 at a negative pressure, in order to suck and hold a certain amount from the solution 300 in the liquid retaining section 1. The present embodiment illustrates an example in which sucking/holding is performed by the first sucking/ejecting member 201.

FIG. 21C to FIG. 21F are diagrams illustrating a process of re-dispersing the particles 350 by stirring the solution 300 retained in the liquid retaining section 1 using the first and second sucking/ejecting members 201 and 202.

Figure 21C:
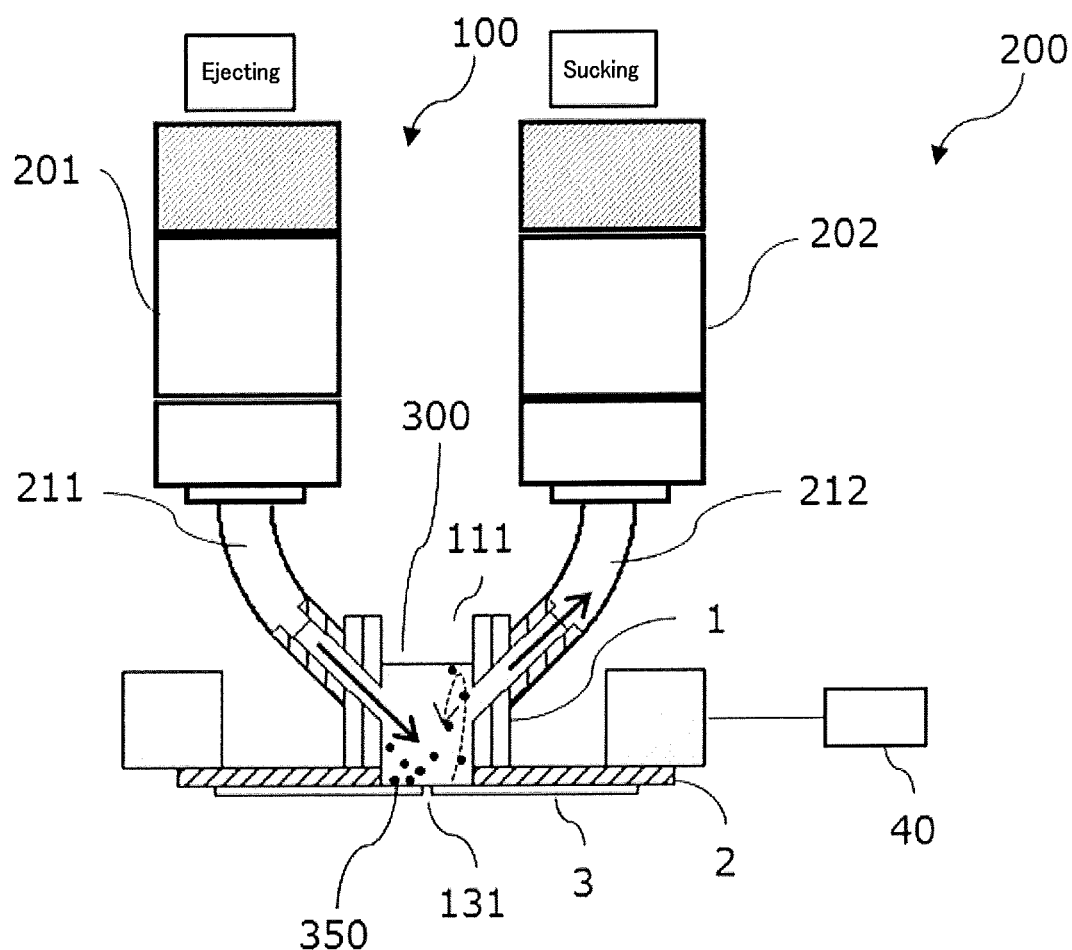
FIG. 21C is a diagram illustrating another example depicting liquid stirring using first and second sucking/ejecting members of a liquid droplet forming device according to the embodiment 1C.

In FIG. 21C, the first sucking/ejecting member 201 performs a primary ejecting operation and the second sucking/ejecting member 202 performs a primary sucking operation.

By the primary ejecting operation, the first sucking/ejecting member 201 puts the interior of the first flow path 211 at a positive pressure and ejects the sucked and held solution 300 into the liquid retaining section 1. The ejected solution 300 forms a flow that is approximately parallel with the center axis of the first flow path 211 at a portion linking to the liquid retaining section 1, and acts to swirl up the particles 350 accumulated on the corner portion formed by the nozzle plate 3 and the vibration member 2 upward in the liquid retaining section 1 by an ascending flow along the wall surface of the liquid retaining section 1. The flow that has ascended along the wall surface of the liquid retaining section 1 becomes a flow to head toward the center of the liquid retaining section 1 at about the liquid surface, and this liquid flow brings the particles 350 which are present at the second flow path 212 side as seen from the center of the nozzles 131 into a dispersed state.

By performing the primary sucking operation, the second sucking/ejecting member 202 puts the interior of the second flow path 212 at a negative pressure to suck and hold a certain amount from the solution 300 in the liquid retaining section 1.

Figure 21D:
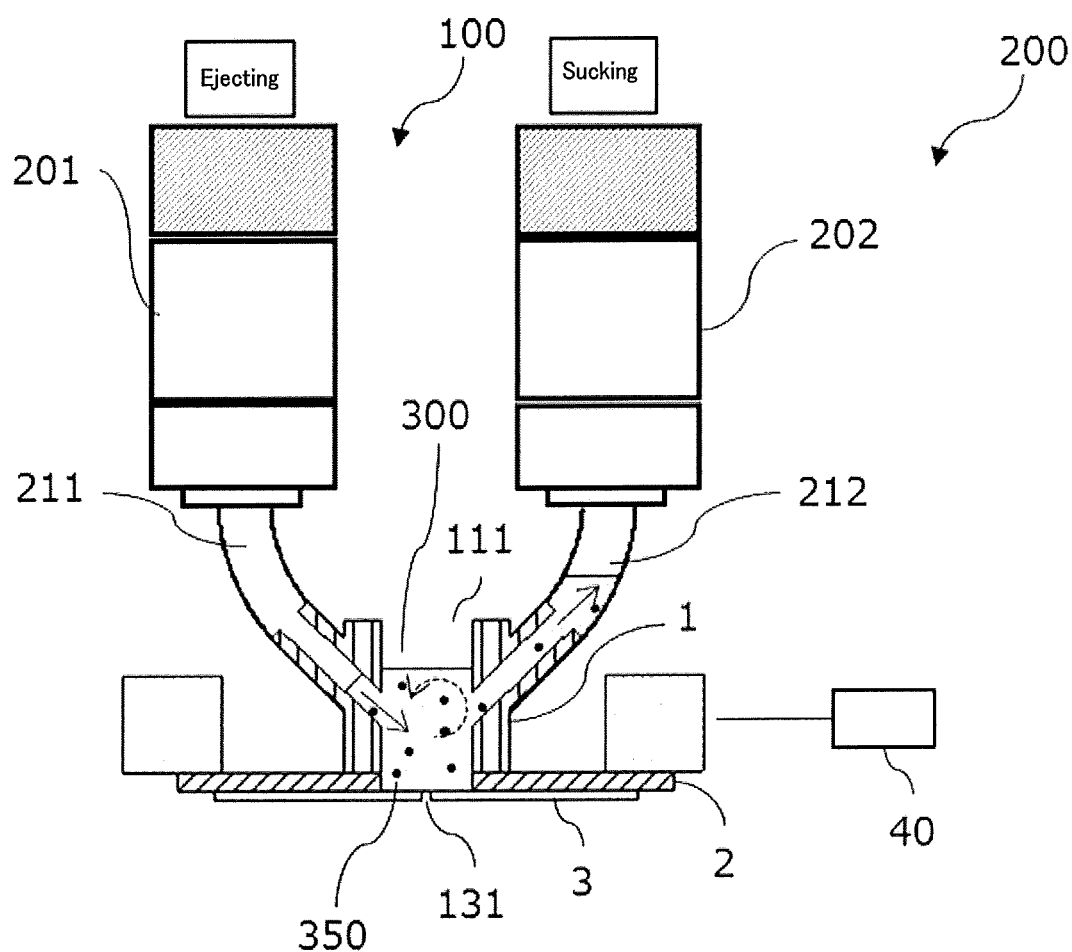
FIG. 21D is a diagram illustrating another example depicting liquid stirring using first and second sucking/ejecting members of a liquid droplet forming device according to the embodiment 1C.

Successively, as illustrated in FIG. 21D, the first sucking/ejecting member 201 performs a secondary ejecting operation and the second sucking/ejecting member 202 performs a secondary sucking operation.

By the secondary ejecting operation, the first sucking/ejecting member 201 puts the interior of the first flow path 211 at a positive pressure and ejects the sucked and held solution 300 into the liquid retaining section 1. The ejected solution 300 generates and maintains a flow for suppressing sedimentation of the particles 350 swirled up by the primary ejecting operation.

Figure 21E:
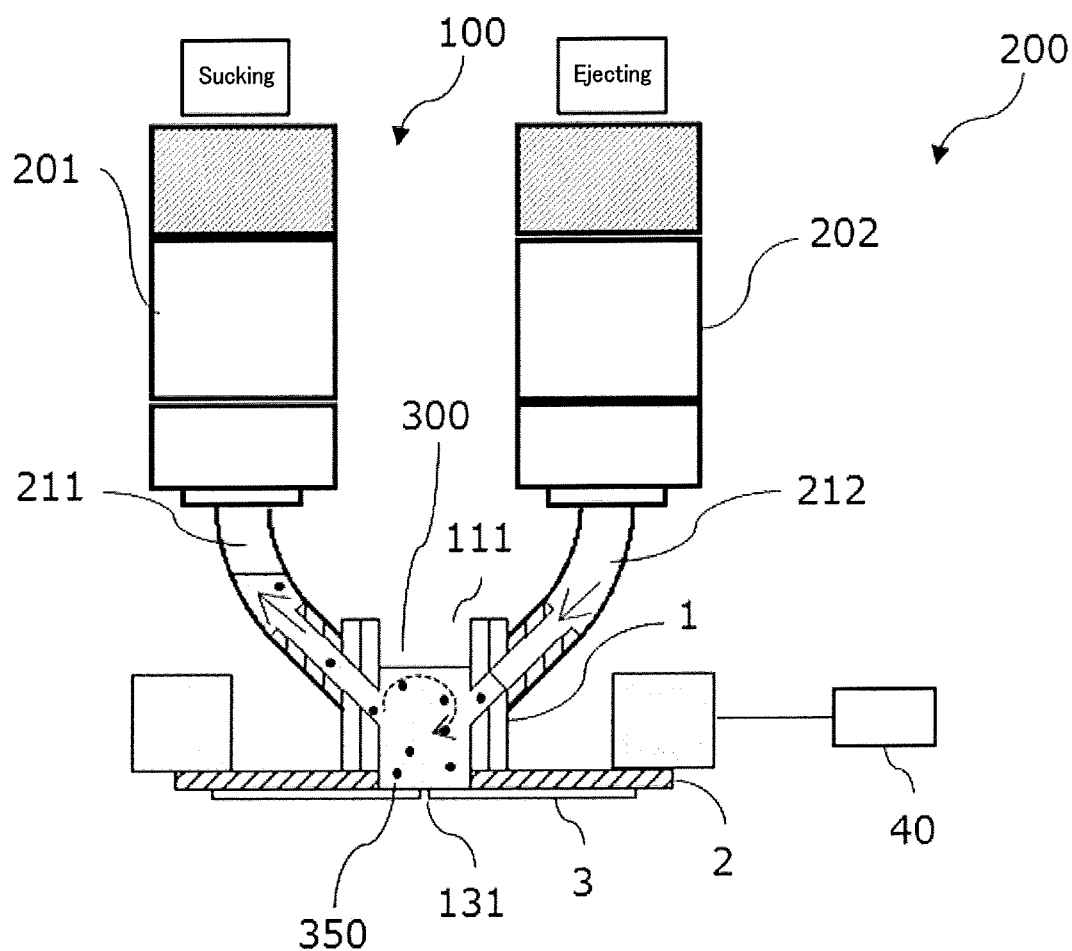
FIG. 21E is a diagram illustrating another example depicting liquid stirring using first and second sucking/ejecting members of a liquid droplet forming device according to the embodiment 1C.

Further, as illustrated in FIG. 21E, the first sucking/ejecting member 201 performs a primary sucking operation and the second sucking/ejecting member 202 performs a primary ejecting operation.

By the primary ejecting operation, the second sucking/ejecting member 202 puts the interior of the second flow path 212 at a positive pressure, and ejects the sucked and held solution 300 into the liquid retaining section 1. The ejected solution 300 forms a flow that is approximately parallel with the center axis of the second flow path 212 at a portion linking to the liquid retaining section 1, and acts to swirl up the particles 350 accumulated on the corner portion formed by the nozzle plate 3 and the vibration member 2 upward in the liquid retaining section 1 by an ascending flow along the wall surface of the liquid retaining section 1. The flow that has ascended along the wall surface of the liquid retaining section 1 becomes a flow to head toward the center of the liquid retaining section 1 at about the liquid surface, and this liquid flow brings the particles 350 which are present at the first flow path 211 side as seen from the center of the nozzles 131 into a dispersed state.

By the primary sucking operation, the first sucking/ejecting member 201 puts the interior of the first flow path 211 at a negative pressure to suck and hold a certain amount from the solution 300 in the liquid retaining section 1.

Figure 21F:
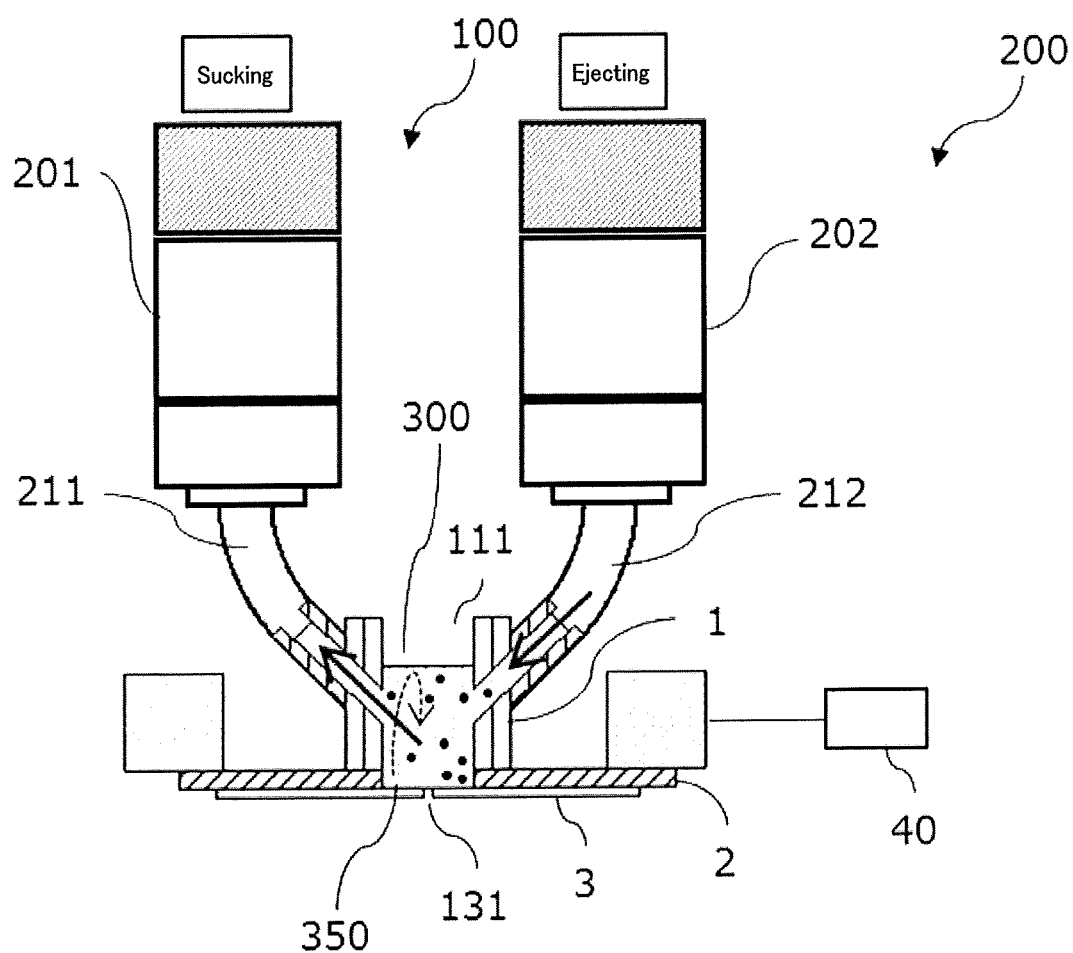
FIG. 21F is a diagram illustrating another example depicting liquid stirring using first and second sucking/ejecting members of a liquid droplet forming device according to the embodiment 1C.

Successively, as illustrated in FIG. 21F, the second sucking/ejecting member 202 performs a secondary ejecting operation and the first sucking/ejecting member 201 performs a secondary sucking operation.

By the secondary ejecting operation, the second sucking/ejecting member 202 puts the interior of the second flow path 212 at a positive pressure and ejects the sucked and held solution 300 into the liquid retaining section 1. The ejected solution 300 generates and maintains a flow for suppressing sedimentation of the particles 350 swirled up by the primary ejecting operation.

Through repetition of the operations described above, the particles 350 that have undergone sedimentation onto the bottom of the liquid retaining section 1 can be re-dispersed with a small amount of a liquid. By performing the liquid droplet forming operation illustrated in FIG. 21B to FIG. 21F in the re-dispersed state, it is possible to prevent discharging failure due to sedimentation of the particles 350 and temporal variation of the content concentration of particles 350 to be contained in liquid droplets 310 discharged.

It is preferable that the first flow path 211 and the second flow path 212 be disposed symmetrically, because one-sided disposition of the flow paths with respect to the center axis passing through the nozzles 131 makes the distribution of the particles 350 in the liquid retaining section 1 non-uniform.

Embodiment 2C

Figure 22:
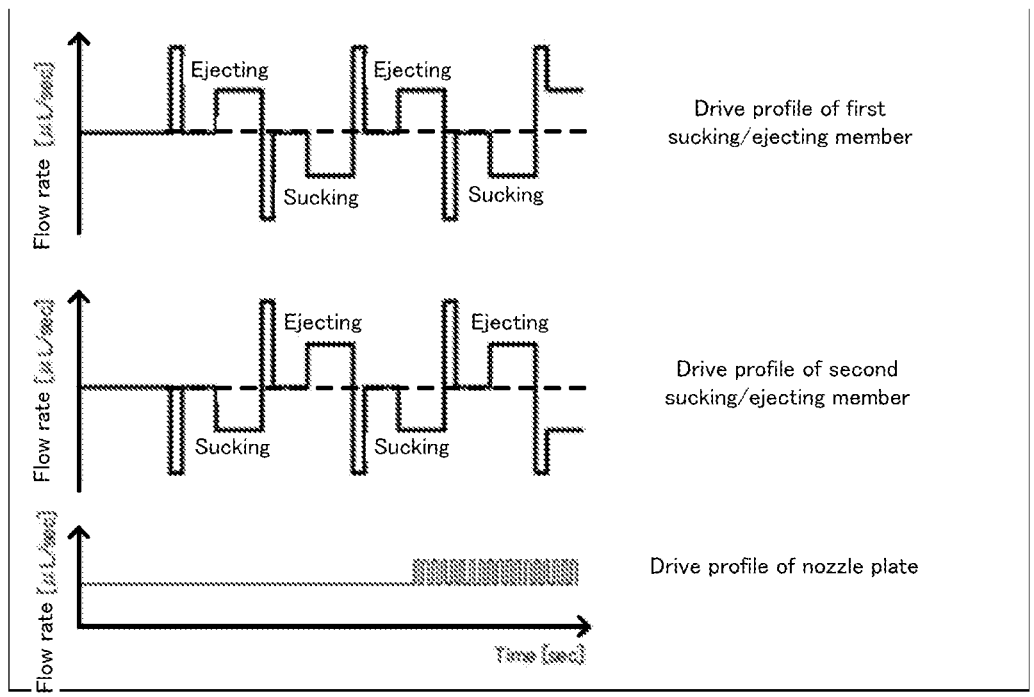
FIG. 22 is a diagram illustrating an example depicting drive profiles of first and second sucking/ejecting members of a liquid droplet forming device according to an embodiment 2C.

FIG. 22 is a diagram depicting a liquid stirring operation of a liquid droplet forming device according to an embodiment 2C using the first and second sucking/ejecting members 201 and 202. Description about the components of the liquid droplet forming device according to the embodiment 2C the same as the components in the embodiments already described will be skipped.

FIG. 22 plots the drive profiles of the first and second sucking/ejecting members 201 and 202 and the drive profile of the nozzle plate 3 by representing time [sec] on the horizontal axis and discharging flow rate [microliter/sec] on the vertical axis.

The first sucking/ejecting member 201 performs an ejecting operation first. Here, a primary ejecting operation for swirling up the particles is performed and then suspended once. Afterwards, a secondary ejecting operation for suppressing sedimentation of the particles over time is performed. Subsequent to the first ejecting operation, a sucking operation is performed. Here, likewise, a primary sucking operation for swirling up the particles is performed and then suspended once. Afterwards, a secondary sucking operation for suppressing sedimentation of the particles over time is performed. As plotted in FIG. 22 where the described ejecting operation, sucking operation, and suspending operation constitute one cycle, the first sucking/ejecting member 201 repeatedly performs the ejecting operation and the sucking operation continuously, to perform the stirring operation constantly.

The second sucking/ejecting member 202 performs a sucking operation first. Here, a primary sucking operation for swirling up the particles is performed and then suspended once. Afterwards, a secondary sucking operation for suppressing sedimentation of the particles over time is performed. Subsequent to the first sucking operation, an ejecting operation is performed. Here, likewise, a primary ejecting operation for swirling up the particles is performed and then suspended once. Afterwards, a secondary ejecting operation for suppressing sedimentation of the particles over time is performed. As plotted in FIG. 22 where the described sucking operation, ejecting operation, and suspending operation constitute one cycle, the second sucking/ejecting member 202 repeatedly performs the sucking operation and the ejecting operation continuously, to perform the stirring operation constantly.

After the primary ejecting operation for swirling up the particles is performed, the operation is intermittently suspended until the motion of the particles stabilizes, and then the secondary ejecting operation for suppressing sedimentation of the particles over time is performed. This makes it possible to reduce the operation of the sucking/ejecting members 201 and 202 to the minimum needed.

Embodiment 3C

Figure 23:
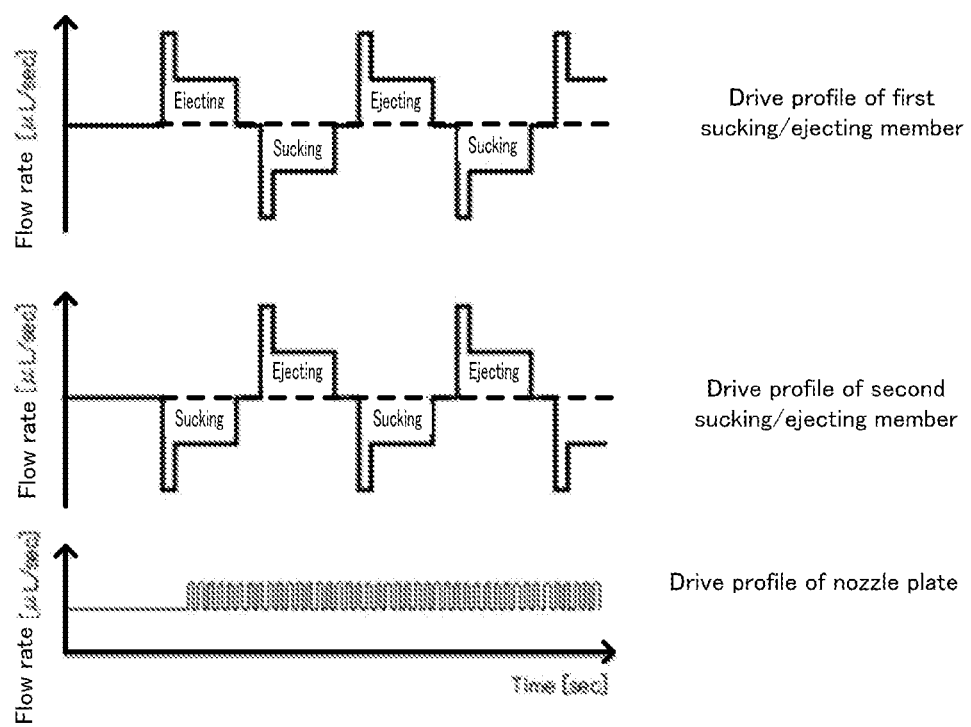
FIG. 23 is a diagram illustrating an example depicting drive profiles of first and second sucking/ejecting members of a liquid droplet forming device according to an embodiment 3C.

FIG. 23 is a diagram depicting a liquid stirring operation of a liquid droplet forming device according to an embodiment 3C using the first and second sucking/ejecting members 201 and 202. Description about the components of the liquid droplet forming device according to the embodiment 3C the same as the components in the embodiments already described will be skipped.

FIG. 23 plots the drive profiles of the first and second sucking/ejecting members 201 and 202 and the drive profile of the nozzle plate 3 by representing time [sec] on the horizontal axis and discharging flow rate [microliter/sec] on the vertical axis.

The first sucking/ejecting member 201 performs an ejecting operation first. Here, a primary ejecting operation for swirling up the particles is performed and then a secondary ejecting operation for suppressing sedimentation of the particles over time is performed. After the first ejecting operation, the operation is suspended once, and then a sucking operation is performed. Here, likewise, a primary sucking operation for swirling up the particles is performed and then a secondary sucking operation for suppressing sedimentation of the particles over time is performed. As plotted in FIG. 23 where the described ejecting operation, sucking operation, and suspending operation constitute one cycle, the first sucking/ejecting member 201 repeatedly performs the ejecting operation and the sucking operation continuously, to perform the stirring operation constantly.

The second sucking/ejecting member 202 performs a sucking operation first. Here, a primary sucking operation for swirling up the particles is performed and then a secondary sucking operation for suppressing sedimentation of the particles over time is performed. After the first sucking operation, the operation is suspended once, and then an ejecting operation is performed. Here, likewise, a primary ejecting operation for swirling up the particles is performed and then a secondary ejecting operation for suppressing sedimentation of the particles over time is performed. As plotted in FIG. 23 where the described sucking operation, ejecting operation, and suspending operation constitute one cycle, the second sucking/ejecting member 202 repeatedly performs the sucking operation and the ejecting operation continuously, to perform the stirring operation constantly.

By suspending the operation intermittently at the switch from an ejecting operation to a sucking operation, it is possible to reduce the burden on the first and second sucking/ejecting members 201 and 202 and extend the service life of the device.

Embodiment 4C

Figure 24:
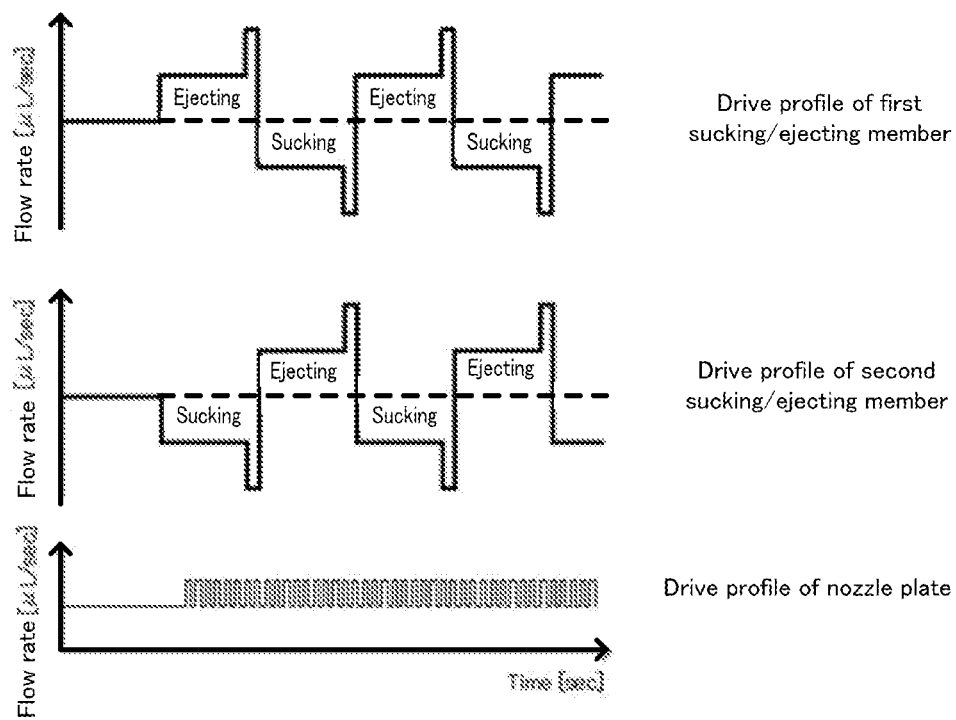
FIG. 24 is a diagram illustrating an example depicting drive profiles of first and second sucking/ejecting members of a liquid droplet forming device according to an embodiment 4C.

FIG. 24 is a diagram depicting a liquid stirring operation of a liquid droplet forming device according to an embodiment 4C using the first and second sucking/ejecting members 201 and 202. Description about the components of the liquid droplet forming device according to the embodiment 4C the same as the components in the embodiments already described will be skipped.

FIG. 24 plots the drive profiles of the first and second sucking/ejecting members 201 and 202 and the drive profile of the nozzle plate 3 by representing time [sec] on the horizontal axis and discharging flow rate [microliter/sec] on the vertical axis.

The first sucking/ejecting member 201 performs an ejecting operation first. Here, a primary ejecting operation for suppressing sedimentation relating to swirling up the particles by a preceding operation is performed, and then a secondary ejecting operation for swirling up the particles is performed. Subsequent to the first ejecting operation, a sucking operation is performed. Here, likewise, a primary sucking operation for suppressing sedimentation relating to swirling up the particles by a preceding operation is performed, and then a secondary sucking operation for swirling up the particles is performed. As plotted in FIG. 24 where the described ejecting operation and sucking operation constitute one cycle, the first sucking/ejecting member 201 repeatedly performs the ejecting operation and the sucking operation continuously, to perform the stirring operation constantly.

Next, the second sucking/ejecting member 202 performs a sucking operation first. Here, a primary sucking operation for suppressing sedimentation relating to swirling up the particles by a preceding operation is performed, and then a secondary sucking operation for swirling up the particles is performed. Subsequent to the first sucking operation, an ejecting operation is performed. Here, likewise, a primary ejecting operation for suppressing sedimentation relating to swirling up the particles by a preceding operation is performed, and then a secondary ejecting operation for swirling up the particles is performed. As plotted in FIG. 24 where the described sucking operation and ejecting operation constitute one cycle, the second sucking/ejecting member 202 repeatedly performs the sucking operation and the ejecting operation continuously, to perform the stirring operation constantly.

Embodiment 5C

Figure 25:
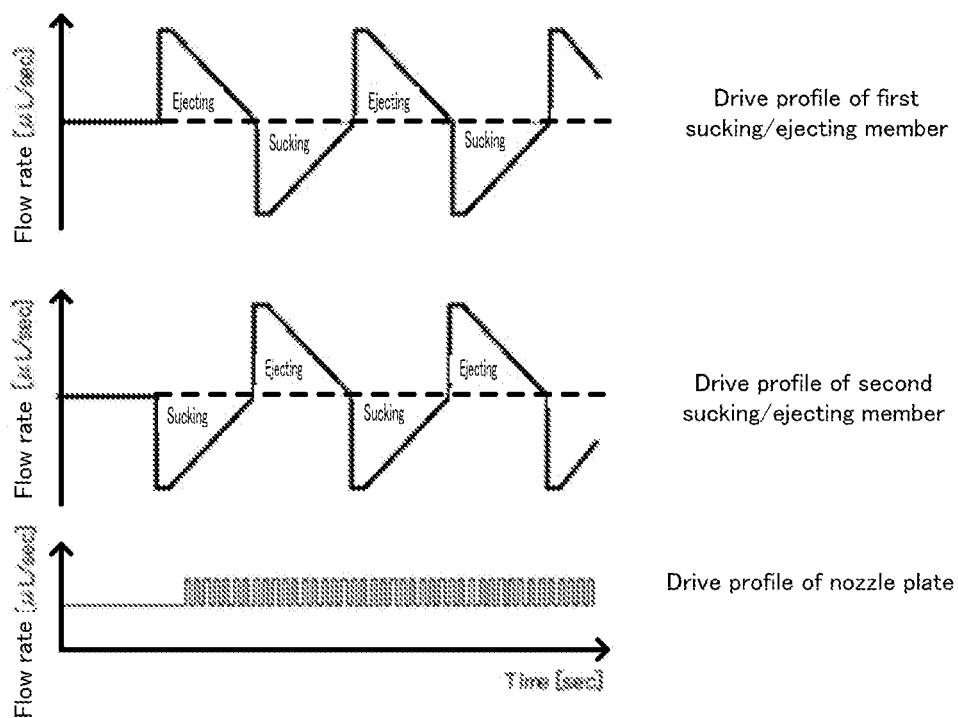
FIG. 25 is a diagram illustrating an example depicting drive profiles of first and second sucking/ejecting members of a liquid droplet forming device according to an embodiment 5C.

FIG. 25 is a diagram depicting a liquid stirring operation of a liquid droplet forming device according to an embodiment 5C using the first and second sucking/ejecting members 201 and 202. Description about the components of the liquid droplet forming device according to the embodiment 5C the same as the components in the embodiments already described will be skipped.

FIG. 25 plots the drive profiles of the first and second sucking/ejecting members 201 and 202 and the drive profile of the nozzle plate 3 by representing time [sec] on the horizontal axis and discharging flow rate [microliter/sec] on the vertical axis.

The first sucking/ejecting member 201 performs an ejecting operation first. Here, an ejecting operation of performing a swirling-up operation first and then decreasing the flow velocity over time for suppressing sedimentation is performed. Subsequent to the first ejecting operation, a sucking operation is performed. Here, likewise, a sucking operation of performing a swirling-up operation first and then decreasing the flow velocity over time for suppressing sedimentation is performed. As plotted in FIG. 25 where the described ejecting operation and sucking operation constitute one cycle, the first sucking/ejecting member 201 repeatedly performs the ejecting operation and the sucking operation continuously, to perform the stirring operation constantly.

The second sucking/ejecting member 202 performs a sucking operation first. Here, a sucking operation of performing a swirling-up operation first and then decreasing the flow velocity over time for suppressing sedimentation is performed. Subsequent to the first sucking operation, an ejecting operation is performed. Here, likewise, an ejecting operation of performing a swirling-up operation first and then decreasing the flow velocity over time for suppressing sedimentation is performed. As plotted in FIG. 25 where the described sucking operation and ejecting operation constitute one cycle, the second sucking/ejecting member 202 repeatedly performs the sucking operation and the ejecting operation continuously, to perform the stirring operation constantly.

Some embodiments have been described. It is possible to obtain the optimum drive profiles by combining these embodiments.

Embodiment 6C

Figure 26:
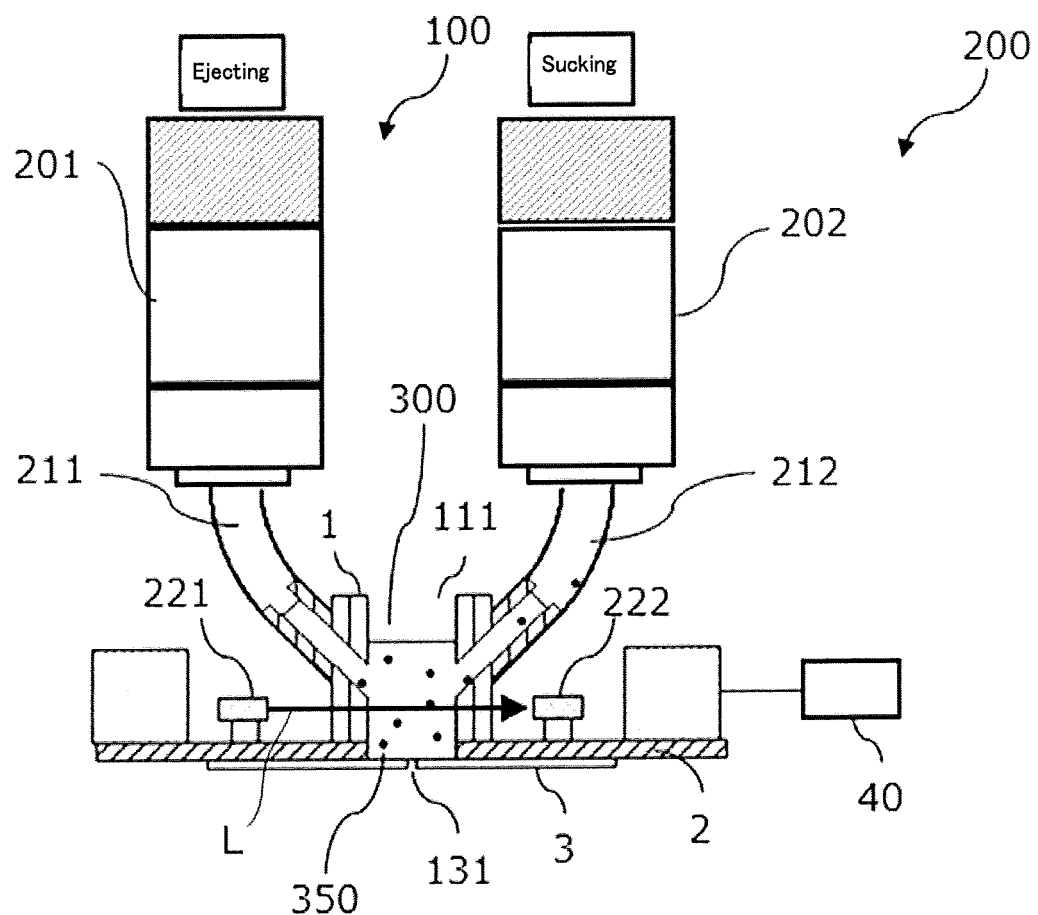
FIG. 26 is a diagram illustrating an example depicting first and second sucking/ejecting members of a liquid droplet forming device according to an embodiment 6C.

FIG. 26 is a diagram depicting an optical method by which a liquid droplet forming device according to an embodiment 6C detects particles in a liquid retaining section. Description about the components of the liquid droplet forming device according to the embodiment 6C the same as the components in the embodiments already described will be skipped.

As illustrated in FIG. 26, the liquid droplet forming device 200 includes a liquid droplet discharging unit 100, first and second sucking/ejecting members 201 and 202, a light source 221, a light receiving element 222, and an illustrated control unit. The liquid droplet discharging unit 100 is the same as the liquid droplet discharging unit 100 according to the embodiment 1.

In FIG. 26, a liquid obtained by dispersing particles (cells) in a predetermined solution after fluorescently staining the particles (cells) with a specific pigment is used as a particle suspension. Particles (cells) are counted by irradiating liquid droplets 310 containing cells, which are particles 350 in the liquid retaining section 1, with light L having a specific wavelength and emitted from the light source 221 and detecting fluorescence emitted by the cells with the light receiving element 222. Here, autofluorescence emitted by molecules originally contained in the cells may be utilized, in addition to the method of staining the cells with a fluorescent pigment. Alternatively, genes for producing fluorescent proteins (for example, GFP (Green Fluorescent Proteins)) may be previously introduced into the cells, in order that the cells may emit fluorescence.

The light source 221 is configured to irradiate the solution 300 containing the particles 350 in the liquid retaining section 1 with light L. The liquid retaining section 1 has a circular-columnar shape or a prismatic shape and is formed of a material having transmissivity to the light L. The beam shape of the light L is an approximately circular shape.

Figure 27:
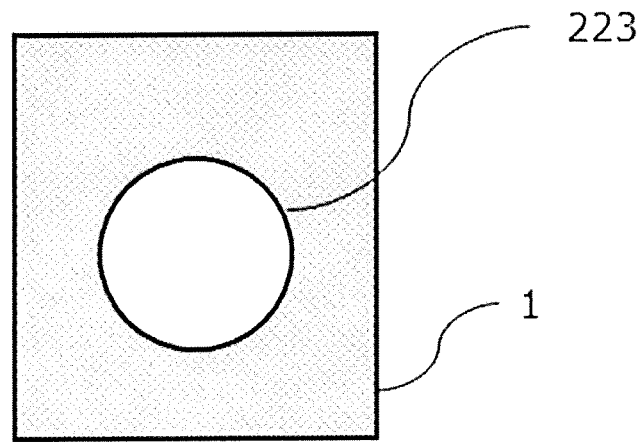
FIG. 27 is a diagram illustrating a method of improving a sensing accuracy by masking a region except for a sensing region in order to let light pass through only the sensing region constituting a part of a liquid retaining section.

As illustrated in FIG. 27, it is effective to improve the sensing accuracy by masking any other regions than a sensing region 223 in order to allow the light L to pass only the sensing region 223, which is part of the liquid retaining section.

It is preferable that the beam diameter of the light L be from about 10 times through 100 times as great as the diameter of the particle 350. This is for ensuring that the particle 350 is irradiated with the light L from the light source 221 without fail even when the position of the particle 350 fluctuates.

However, it is not preferable if the beam diameter of the light L is much greater than 100 times as great as the diameter of the particle 350. This is because the energy density of the light with which the particle 350 is irradiated is reduced, to lower the light volume of fluorescence Lf to be emitted upon the light L serving as excitation light, making it difficult for the light receiving element 222 to detect the fluorescence Lf.

It is preferable that the light L emitted by the light source 221 be pulse light. It is preferable to use, for example, a solid-state laser, a semiconductor laser, and a dye laser. When the light L is pulse light, the pulse width is preferably 10 microseconds or less and more preferably 1 microsecond or less. The energy per unit pulse is preferably roughly 0.1 microjoules or higher and more preferably 1 microjoule or higher, although significantly depending on the optical system such as presence or absence of light condensation.

The light receiving element 222 is configured to receive fluorescence Lf emitted by a fluorescent-stained cell 350 upon absorption of the light L as excitation light, when the fluorescent-stained cell 350 is contained in the solution 300. Because the fluorescence Lf is emitted to all directions from the fluorescent-stained cell 350, the light receiving element 222 can be disposed at an arbitrary position at which the fluorescence Lf is receivable. Here, in order to improve contrast, it is preferable to dispose the light receiving element 222 at a position at which direct incidence of the light L emitted by the light source 221 to the light receiving element 222 does not occur.

The light receiving element 222 is not particularly limited and may be appropriately selected depending on the intended purpose so long as the light receiving element 222 is an element capable of receiving the fluorescence Lf emitted by the fluorescent-stained cell 350. An optical sensor configured to receive fluorescence from a cell in a liquid droplet when the liquid droplet is irradiated with light having a specific wavelength is preferable.

Examples of the light receiving element 222 include one-dimensional elements such as a photodiode and a photosensor. When high-sensitivity measurement is needed, it is preferable to use a photomultiplier tube and an Avalanche photodiode. As the light receiving element 222, two-dimensional elements such as a CCD (Charge Coupled Device), a CMOS (Complementary Metal Oxide Semiconductor), and a gate CCD may be used.

The fluorescence Lf emitted by the fluorescent-stained cell 350 is weaker than the light L emitted by the light source 221. Therefore, a filter configured to attenuate the wavelength range of the light L may be installed at a preceding stage (light receiving surface side) of the light receiving element 222. This enables the light receiving element 222 to obtain an extremely highly contrastive image of the fluorescent-stained cell 350. As the filter, for example, a notch filter configured to attenuate a specific wavelength range including the wavelength of the light L may be used.

As described above, it is preferable that the light L emitted by the light source 221 be pulse light. However, the light L emitted by the light source 221 may be continuously oscillating light.

The control unit has a function of controlling the first and second sucking/ejecting members 201 and 202 and the light source 221. The control unit also has a function of obtaining information that is based on the light volume received by the light receiving element 222 and counting the number of fluorescent-stained cells 350 (the case where the number is zero is also included).

A threshold for a counted number of fluorescent-stained cells 350 may be preset for a primary sucking/ejecting operation and a secondary sucking/ejecting operation of the first and second sucking/ejecting members 201 and 202. Based on the number, the velocity of the primary and secondary sucking/ejecting operations may be determined.

Alternatively, a threshold for a counted number of fluorescent-stained cells 350 may be preset for a primary sucking/ejecting operation and a secondary sucking/ejecting operation of the first and second sucking/ejecting members 201 and 202. Based on the number, the operation time of the primary and secondary sucking/ejecting operations may be adjusted.

Embodiment 1D

A liquid droplet forming device according to an embodiment 1D includes a liquid droplet discharging unit including: a discharging port; a liquid retaining section including the discharging port; first and second sucking/ejecting members configured to suck and eject a liquid in the liquid retaining section; a first flow path linking the liquid retaining section and the first sucking/ejecting member to each other; a second flow path linking the liquid retaining section and the second sucking/ejecting member to each other; a sucking/ejecting control unit configured to control a sucking operation and an ejecting operation of the first and second sucking/ejecting members; and a liquid surface detecting member configured to detect the position of the liquid surface in the liquid retaining section.

Figure 28:
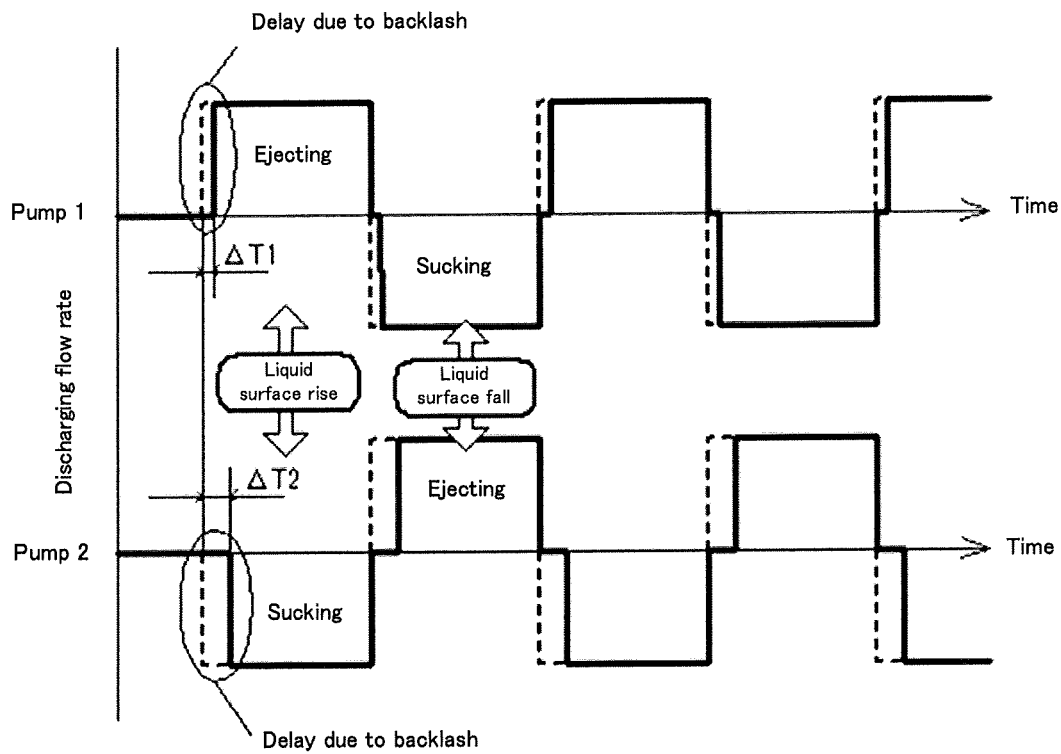
FIG. 28 is a diagram illustrating an example of occurrence of operation gaps due to backlash of first and second sucking/ejecting members of a liquid droplet forming device according to an embodiment 1D.

FIG. 28 is a diagram depicting occurrence of operation gaps due to backlash of the first and second sucking/ejecting members of the liquid droplet forming device 200 according to the embodiment 1D. The liquid droplet forming device 200 according to the embodiment 1D is the same as the liquid droplet forming device 200 according to the embodiment 1A except for the difference described below. Therefore, description about components that are the same as the components already described in the liquid droplet forming device according to the embodiment 1A will be skipped.

However, a delay due to backlash may occur at the switch from an ejecting operation to a sucking operation of the first and second sucking/ejecting members 201 and 202. Therefore, even when the first and second sucking/ejecting members are controlled to be driven at the same timing, a time difference occurs between the starts of an ejecting operation and a sucking operation of the first and second sucking/ejecting members 201 and 202 (the difference between ΔT1 and ΔT2 in FIG. 28). Consequently, a gap occurs between an ejecting amount into the tank and a sucking amount from the tank, to fluctuate the liquid surface height and make liquid droplet discharging from the head unstable.

Embodiment 2D

Figure 29:
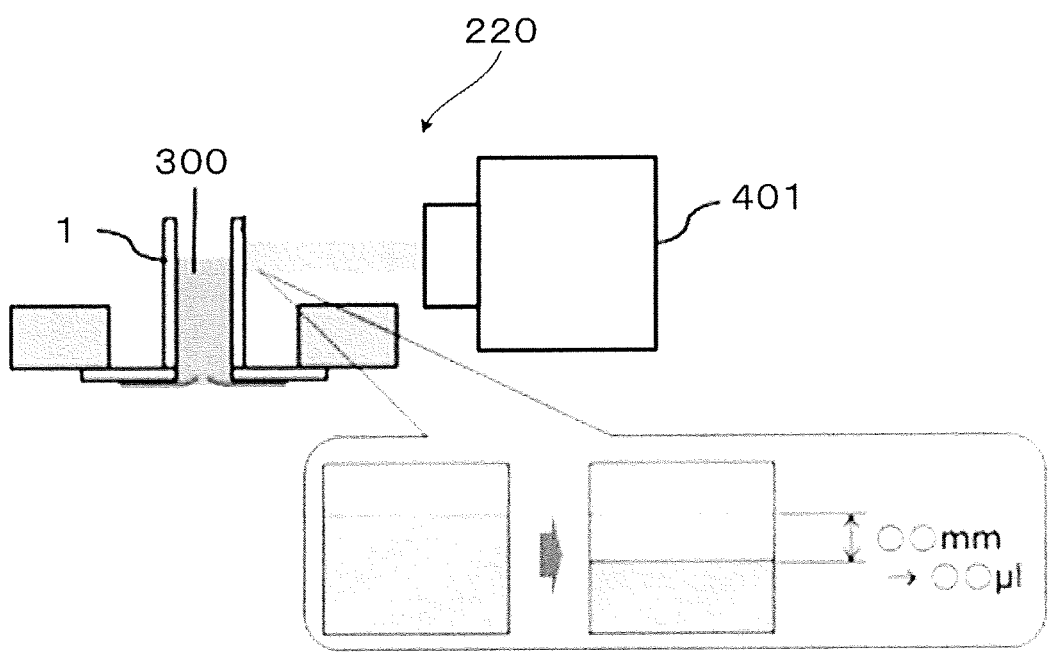
FIG. 29 is a diagram depicting an example of a configuration in which a liquid surface detecting member is disposed in a liquid retaining section of a liquid droplet forming device according to an embodiment 2D.

FIG. 29 is a diagram depicting a configuration in which a liquid surface detecting member is disposed in a liquid retaining section 1 of a liquid droplet forming device 200 according to an embodiment 2D. Description about the components of the liquid droplet forming device according to the embodiment 2D the same as the components in the embodiments already described will be skipped.

Hence, an image sensor 401 is provided as a liquid surface detecting member capable of constantly detecting liquid surface changes in the liquid retaining section 1 of the liquid droplet discharging unit. When the liquid surface shifts from the prescribed value, control for switching between sucking/ejecting operations of the two sucking/ejecting members is performed based on the detection result, to synchronize an ejecting operation and a sucking operation of the two sucking/ejecting members with each other, and maintain the liquid amount in the liquid retaining section 1 of the liquid droplet discharging unit constant, to maintain the liquid surface height.

As the liquid surface detecting member, any other unit than the image sensor, such as a unit based on a light emitting element and a position sensor, and a water detection sensor by a photoelectric sensor may be used.

For the prescribed value of the liquid surface height for the control of switching between ejecting/sucking operations of the two sucking/ejecting members, the upper limit value or the lower limit value or both may be set externally by a human operator by using, for example, an SP mode of the control unit.

An output device configured to output the detection result of the liquid surface detecting member may be provided, and the liquid surface height may be digitally displayed on an operation unit of the output device. This makes it possible for a human operator to constantly monitor liquid surface changes in the liquid retaining section 1 of the head.

Further, for example, a LED lamp may be provided. This makes it possible to display any liquid surface shift from the prescribed value by luminescence, based on a signal from the output device configured to output the detection result of the liquid surface detecting member.

Embodiment 3D

Figure 30:
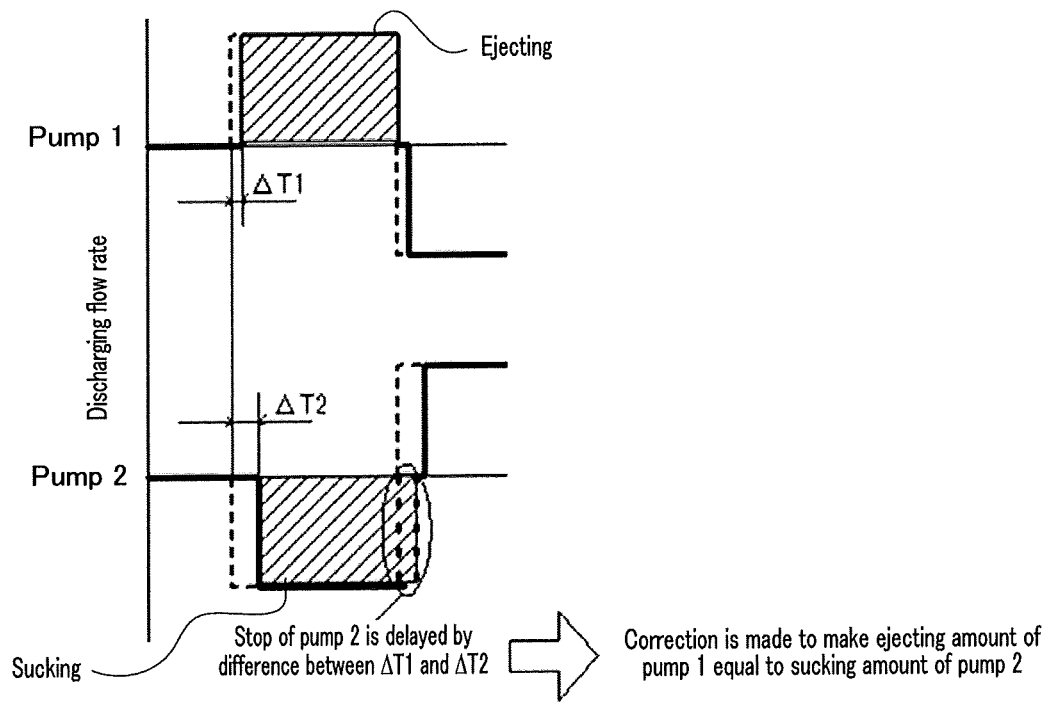
FIG. 30 is a diagram depicting an example of an operation of two sucking/ejecting members under a liquid surface change correcting control when a change of a liquid surface is detected for the first time in a liquid droplet forming device according to an embodiment 3D.

FIG. 30 is a diagram depicting an operation of two pumps under a liquid surface change correcting control when a change of the liquid surface is detected for the first time in a liquid droplet forming device 200 according to an embodiment 3D. Description about the components of the liquid droplet forming device according to the embodiment 3D the same as the components in the embodiments already described will be skipped.

A rise of the liquid surface is due to a delay of a sucking operation by a pump 2 from the start of an ejecting operation by a pump 1 as illustrated in FIG. 30. Therefore, in the operation in which the rise of the liquid surface is sensed, a control for delaying stopping the pump 2 from the stop of the pump 1 is performed in order to correct the difference corresponding to the rise of the liquid surface.

Embodiment 4D

Figure 31:
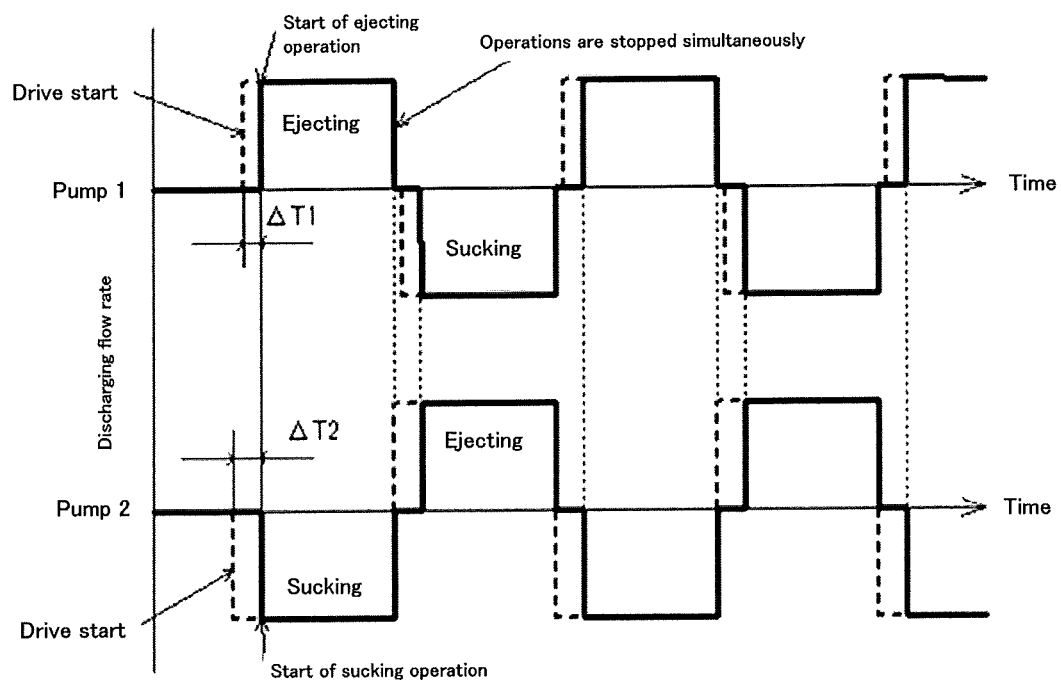
FIG. 31 is a diagram depicting an example of an operation of two sucking/ejecting members under a continuous liquid surface change correcting control in a liquid droplet forming device according to an embodiment 4D.

FIG. 31 is a diagram depicting an operation of two pumps under a continuous liquid surface change correcting control in a liquid droplet forming device 200 according to an embodiment 4D. Description about the components of the liquid droplet forming device according to the embodiment 4D the same as the components in the embodiments already described will be skipped.

Further, in the next ejecting/sucking operation, a control for bringing the timing to start driving the pump 2 to perform a sucking operation ahead of driving the pump 1 to perform an ejecting operation by a difference between $\Delta T1$ and $\Delta T2$ and stopping the pumps at the same time is performed, to synchronize the ejecting/sucking operations of the two pumps.

A fall of the liquid surface is due to a delay of an ejecting operation by one pump from the start of operation of the other sucking pump. Therefore, in the operation in which the fall of the liquid surface is sensed, a control for delaying stopping the ejecting operation of the ejecting pump from the stop of the sucking pump is performed in order to correct the difference corresponding to the fall of the liquid surface. Further, in the next sucking/ejecting operation, a control for bringing the timing to start driving the ejecting pump to operate ahead of the start of driving the sucking pump to operate by the same amount by which the previous fall of the liquid surface is corrected and stopping the pumps at the same time is performed, to synchronize the ejecting/sucking operations of the two pumps.

Afterwards, when a rise or a fall of the liquid surface is detected during constant sensing of any liquid surface changes in the liquid retaining section, the controls described above are repeated to maintain the liquid surface constant throughout continuation of the stirring operation.

By setting the same sucking velocity, the same ejecting velocity, the same liquid sucking amount, the same liquid ejecting amount, and the same timing, it is possible to stir the solution 300 while maintaining the liquid amount in the liquid retaining section 1 constant as illustrated in FIG. 4A to FIG. 4C of the embodiment 1A. With this operation, the fall velocity of the liquid droplets does not fluctuate even when the discharging operation is performed while the particles 350 contained in the solution 300 in the liquid retaining section 1 are maintained in the uniformly dispersed state, making it possible to discharge liquid droplets at a constant fall velocity with a constant concentration of particles contained.

As described above, the liquid surface detecting member constantly detects the liquid surface in the liquid retaining section. Therefore, it is always possible to perform an ejecting/sucking operation switching control conforming to the situation, whether initial difference between the two pumps or status change over time, making it possible to maintain the liquid surface height constant.

For example, when the liquid amount of the solution 300 in the liquid retaining section 1 is high, when the particle diameter of the particles 350 contained in the solution 300 is large, or when the content concentration is high, the liquid stirring amount or the sucking/ejecting velocity of the first and second liquid sucking/ejecting members 201 and 202 better be high in order to disperse the particles uniformly. On the other hand, when the particles 350 contained are particles that may be damaged by impacts, such as animal cells, the liquid stirring amount or the sucking/ejecting velocity better be as low as possible, and the stirring frequency better be low. Further, as in FIG. 4A to FIG. 4C of the embodiment 2A, the liquid stirring amount or the sucking/ejecting velocity needed varies from the case of re-dispersing the particles from the complete sedimentation state of the particles 350 to the case of suppressing sedimentation of the particles 350 that are in a dispersed state as described above. A higher liquid stirring amount or a higher sucking/ejecting velocity is needed in the former case.

As described above, the liquid stirring amount or the sucking velocity/ejecting velocity needed varies depending on, for example, the amount of the solution 300, the kind or concentration of the particles 350, or the sedimentation state. Therefore, it is preferable that the liquid stirring amount or the sucking/ejecting velocity be switchable.

Embodiment 1E

A liquid droplet forming device according to an embodiment 1E includes a liquid droplet discharging unit including: a discharging port; a liquid retaining section including the discharging port; first and second sucking/ejecting members configured to suck and eject a liquid in the liquid retaining section; a first flow path linking the liquid retaining section and the first sucking/ejecting member to each other; a second flow path linking the liquid retaining section and the second sucking/ejecting member to each other; and a sucking/ejecting control unit configured to control a sucking operation and an ejecting operation of the first and second sucking/ejecting members, wherein the first sucking/ejecting member is driven to perform sucking/ejecting operations continuously and the second sucking/ejecting member is driven to perform sucking/ejecting operations intermittently, and wherein an intermittent stop period of the second sucking/ejecting member is varied according to information on a delay time from the start of driving each sucking/ejecting member to perform a sucking/ejecting operation until the start of the sucking/ejecting operation.

Figure 32:
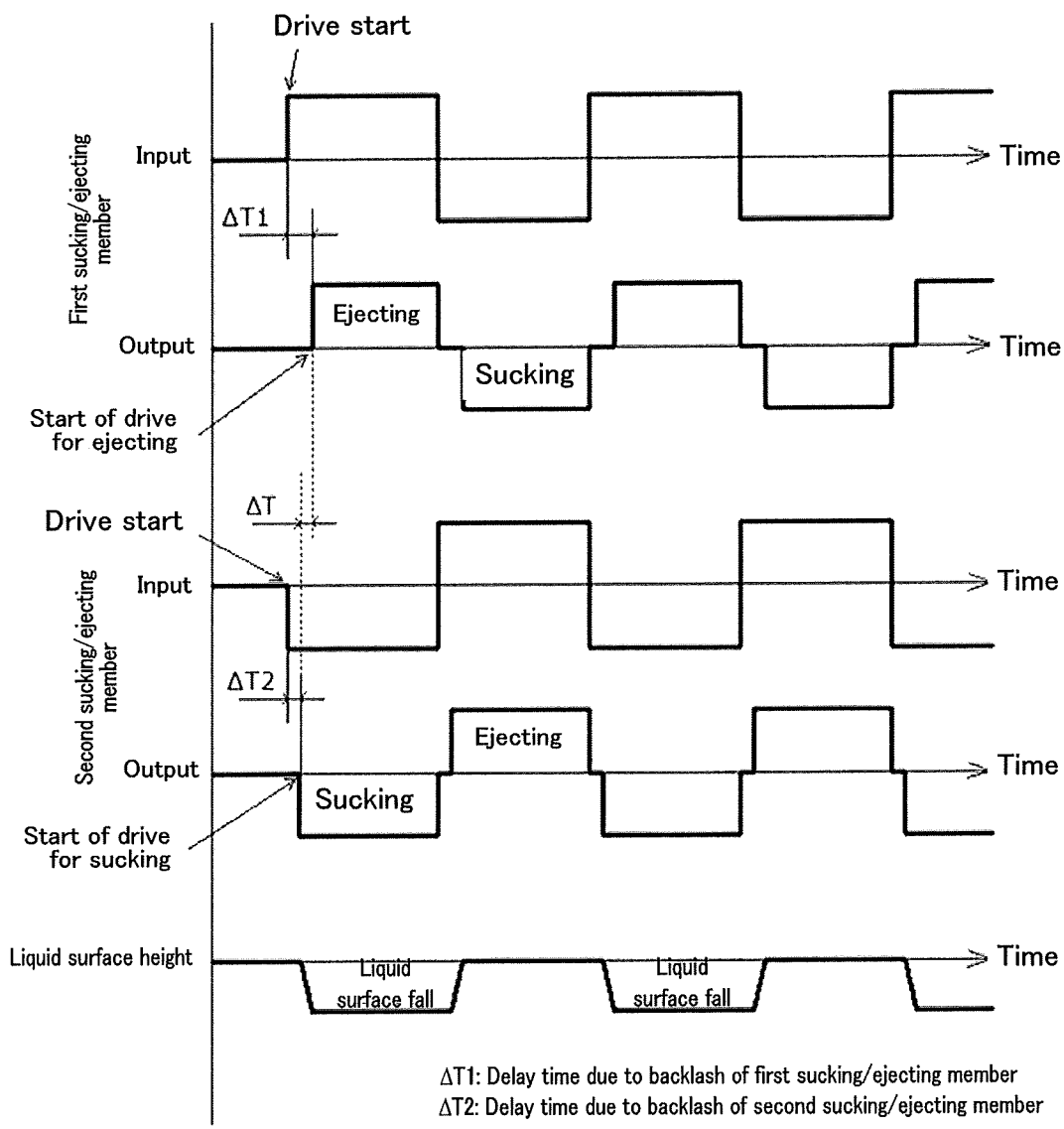
FIG. 32 is a diagram depicting delay time due to backlash that occurs when first and second sucking/ejecting members are switched in drive between sucking and ejecting operations in a liquid droplet forming device according to an embodiment 1E.

FIG. 32 is a diagram depicting a delay time due to backlash that occurs when first and second sucking/ejecting members are switched in drive between a sucking operation and an ejecting operation in a liquid droplet forming device 200 according to the embodiment 1E. The liquid droplet forming device 200 according to the embodiment 1E is the same as the liquid droplet forming device 200 according to the embodiment 1A except for the following point. Therefore, description about components that are the same as the components already described in the liquid droplet forming device according to the embodiment 1A will be skipped.

However, at the switch from an ejecting operation to a sucking operation of the first and second sucking/ejecting members 201 and 202, delay times ($\Delta T1$ and $\Delta T2$ in FIG. 32) due to backlash may occur from the start of the drive (input) until the start of the operation (output). The backlash level varies between the sucking/ejecting members. Therefore, even when the first and second sucking/ejecting members are controlled to start to be driven at the same timing, a time difference occurs between the starts of an ejecting operation or a sucking operation of the first and second sucking/ejecting members 201 and 202 (the difference between ΔT1 and ΔT2 in FIG. 32). Consequently, a gap occurs between an ejecting amount into the liquid retaining section and a sucking amount from the liquid retaining section, to fluctuate the liquid surface height and make liquid droplet discharging from the head unstable.

Embodiment 2E

Figure 33:
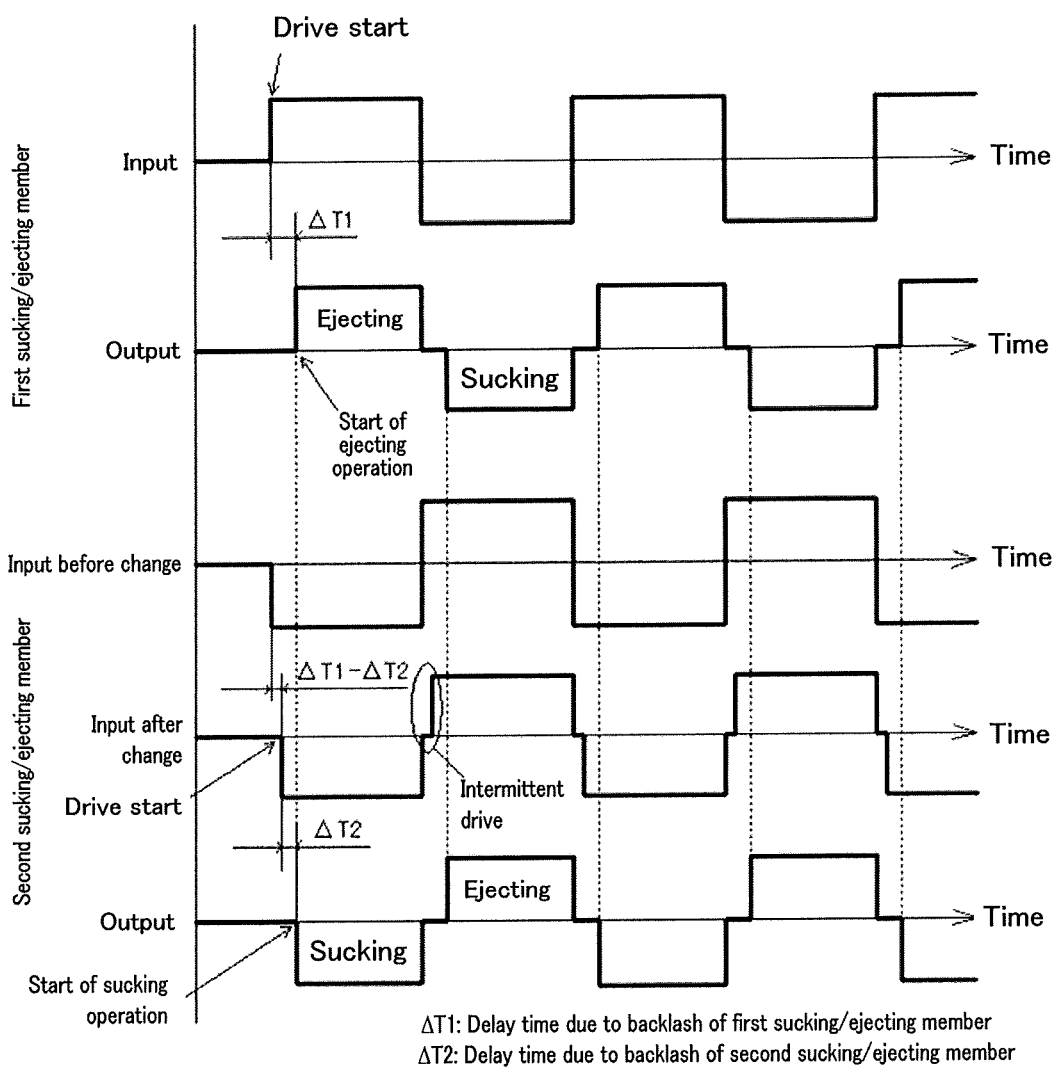
FIG. 33 is a diagram depicting a configuration for driving a first sucking/ejecting member to perform sucking/ejecting operations continuously and driving a second sucking/ejecting member to perform sucking/ejecting operations intermittently depending on an amount of backlash of each sucking/ejecting member in a liquid droplet forming device according to an embodiment 2E.

FIG. 33 is a diagram depicting a configuration for driving a first sucking/ejecting member to perform sucking/ejecting operations continuously and driving a second sucking/ejecting member to perform sucking/ejecting operations intermittently depending on an amount of backlash of each sucking/ejecting member in a liquid droplet forming device 200 according to an embodiment 2E. Description about the components of the liquid droplet forming device according to the embodiment 2E the same as the components in the embodiments already described will be skipped.

Hence, the sucking/ejecting member having a shorter delay time due to backlash is intermittently driven with a stop period set at the switch of drive between sucking/ejecting operations, whereas the sucking/ejecting member having a longer delay time due to backlash is continuously driven for continuous switching between sucking/ejecting operations. Here, the stop period is the difference between the delay times of the two sucking/ejecting members due to backlash. The second sucking/ejecting member having the shorter delay time due to backlash is stopped at the switch of drive between sucking/ejecting operations, in order to be driven to perform sucking/ejecting operations intermittently, to synchronize ejecting/sucking operations of the first sucking/ejecting member and the second sucking/ejecting member with each other, and maintain the liquid amount in the liquid retaining section of the head constant, to maintain the liquid surface height.

Embodiment 3E

Figure 34:
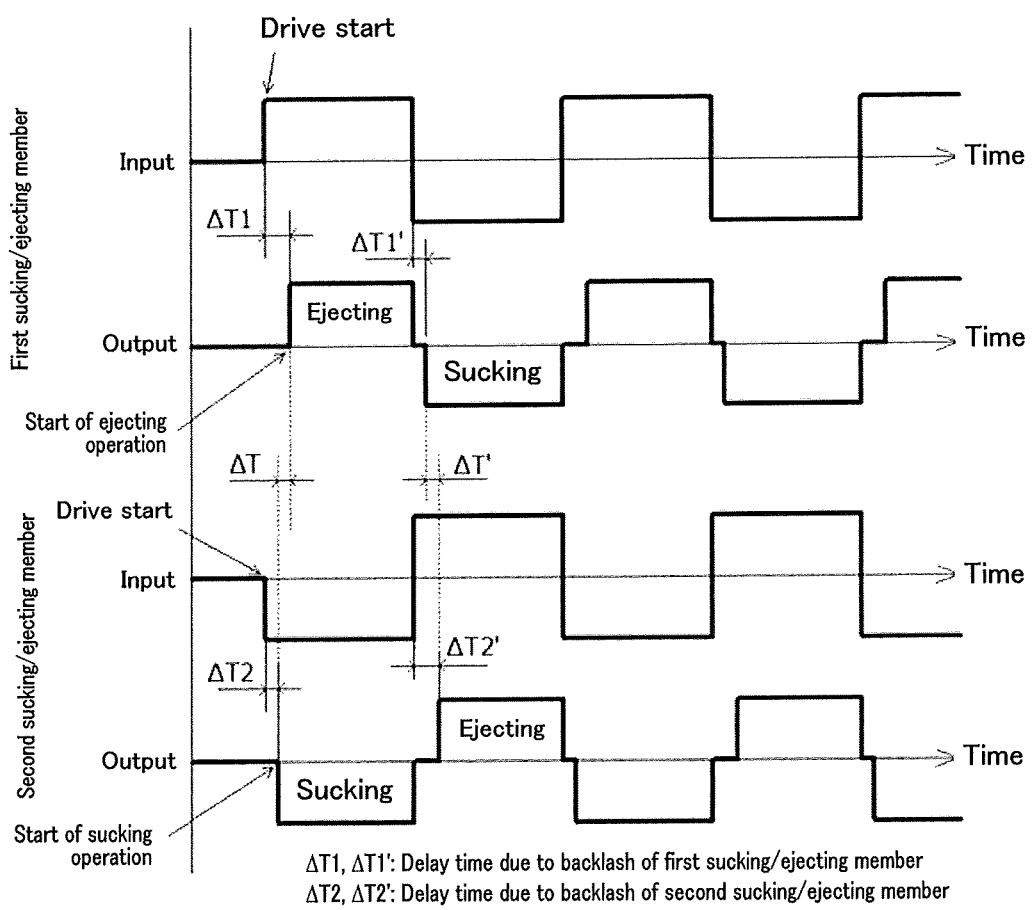
FIG. 34 is a diagram depicting a configuration for driving a first sucking/ejecting member and a second sucking/ejecting member to perform sucking/ejecting operations intermittently depending on an amount of backlash of each sucking/ejecting member in a liquid droplet forming device according to an embodiment 3E.
Figure 35:
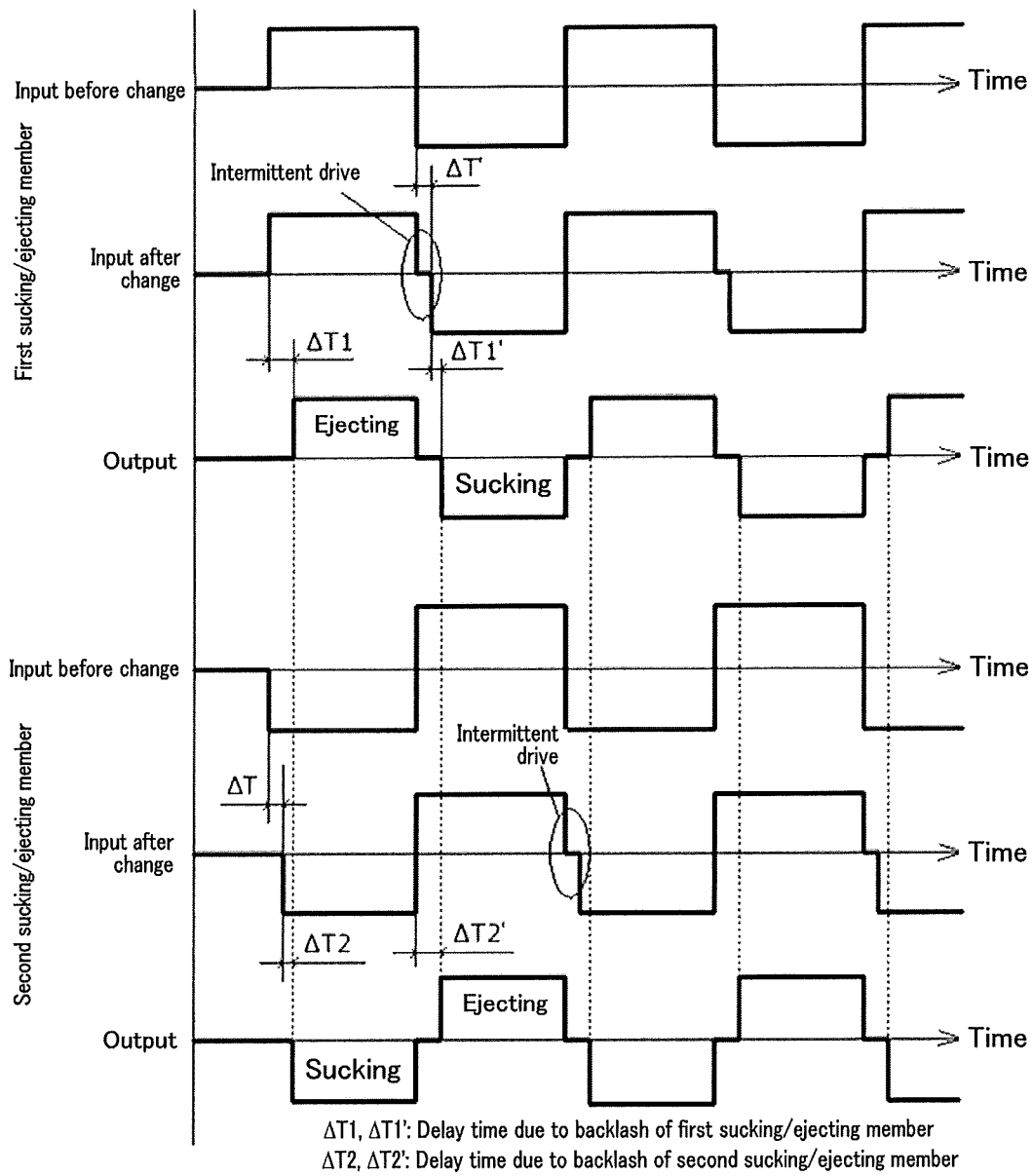
FIG. 35 is a diagram depicting a configuration for driving a first sucking/ejecting member and a second sucking/ejecting member to perform sucking/ejecting operations intermittently depending on an amount of backlash of each sucking/ejecting member in a liquid droplet forming device according to an embodiment 3E.
Figure 36:
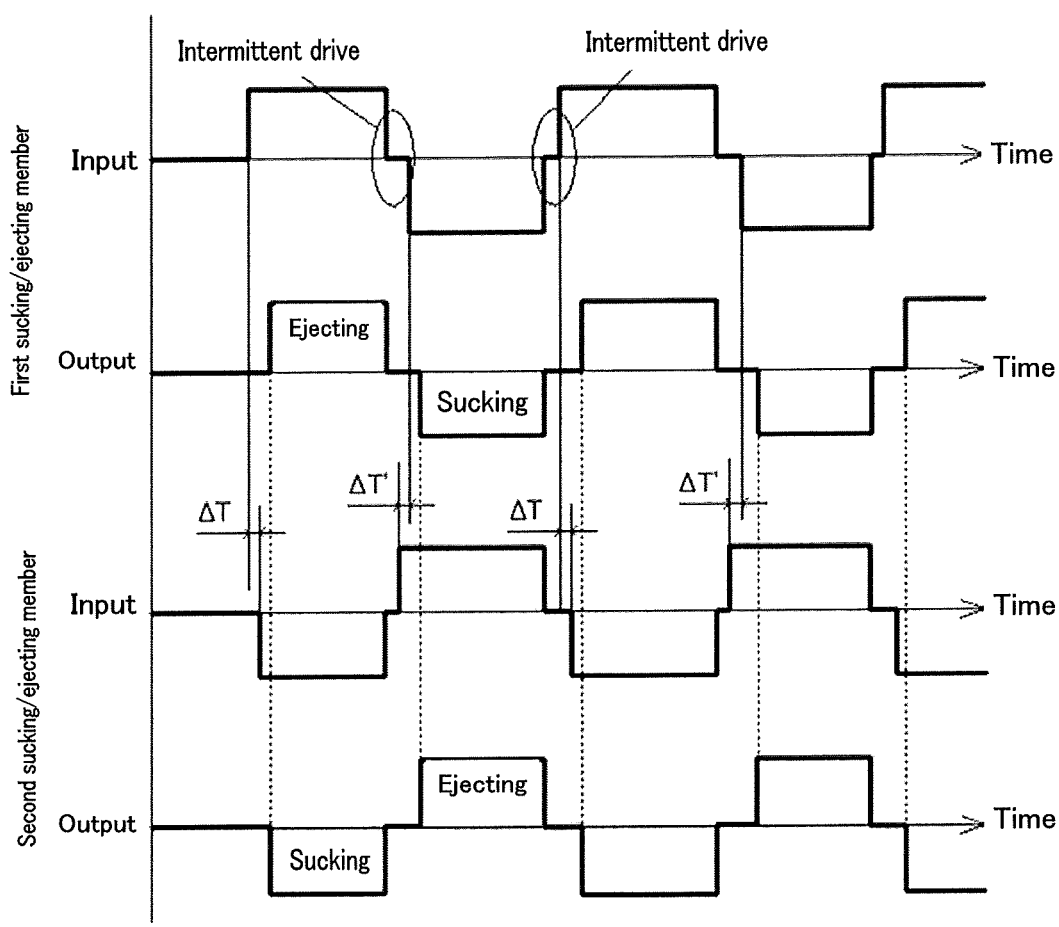
FIG. 36 is a diagram depicting a configuration for driving a first sucking/ejecting member and a second sucking/ejecting member to perform sucking/ejecting operations intermittently depending on an amount of backlash of each sucking/ejecting member in a liquid droplet forming device according to an embodiment 3E.

FIG. 34, FIG. 35, and FIG. 36 are diagrams depicting a configuration for driving a first sucking/ejecting member and a second sucking/ejecting member to perform sucking/ejecting operations intermittently depending on an amount of backlash of each sucking/ejecting member in a liquid droplet forming device 200 according to an embodiment 3E. Description about the components of the liquid droplet forming device according to the embodiment 3E the same as the components in the embodiments already described will be skipped.

As illustrated in FIG. 34, when the relationship of which is the higher or the lower of ΔT1 and ΔT2 is inconsistent with the relationship of which is the higher or the lower of ΔT1' and ΔT2', it is impossible to synchronize the sucking/ejecting members with each other only by intermittently driving one of the sucking/ejecting members, where ΔT1 represents a delay time due to backlash when the first sucking/ejecting member is switched from sucking to ejecting, ΔT1' represents a delay time due to backlash when the first sucking/ejecting member is switched from ejecting to sucking, ΔT2 represents a delay time due to backlash when the second sucking/ejecting member is switched from ejecting to switching, and ΔT2' represents a delay time due to backlash when the second sucking/ejecting member is switched from sucking to ejecting.

Hence, the first sucking/ejecting member and the second sucking/ejecting member are intermittently driven with stop periods set at the switch of drive between sucking/ejecting operations respectively, to synchronize sucking/ejecting operations.

Of the first sucking/ejecting member and the second sucking/ejecting member, the sucking/ejecting member having a shorter delay time at the switch of drive between sucking/ejecting operations is to be provided with a stop period. The stop period is the difference between delay times (ΔT, ΔT') of the first and second sucking/ejecting members at the switch of drive between sucking/ejecting operations (see FIG. 35).

The intermittent driving method described above can realize the most efficient stirring flow generation by sucking/ejecting operations. However, it is also possible to set a stop period at every switch of drive between sucking/ejecting operations of the first sucking/ejecting member and the second sucking/ejecting member (see FIG. 36).

Embodiment 4E

Figure 37:
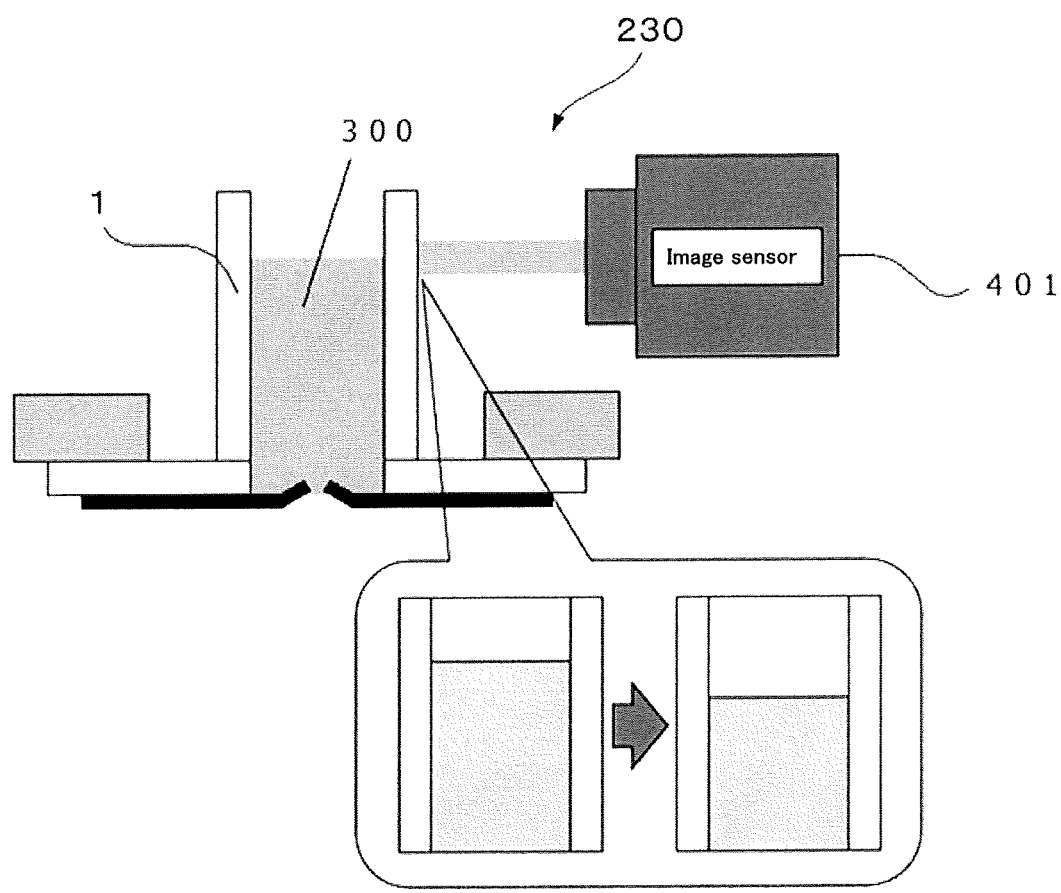
FIG. 37 is a diagram depicting a configuration in which a liquid surface sensing member is disposed in a liquid retaining section as a unit configured to sense a delay time that occurs at the switch of drive between sucking/ejecting operations of a first sucking/ejecting member and a second sucking/ejecting member in a liquid droplet forming device according to an embodiment 4E.
Figure 38:
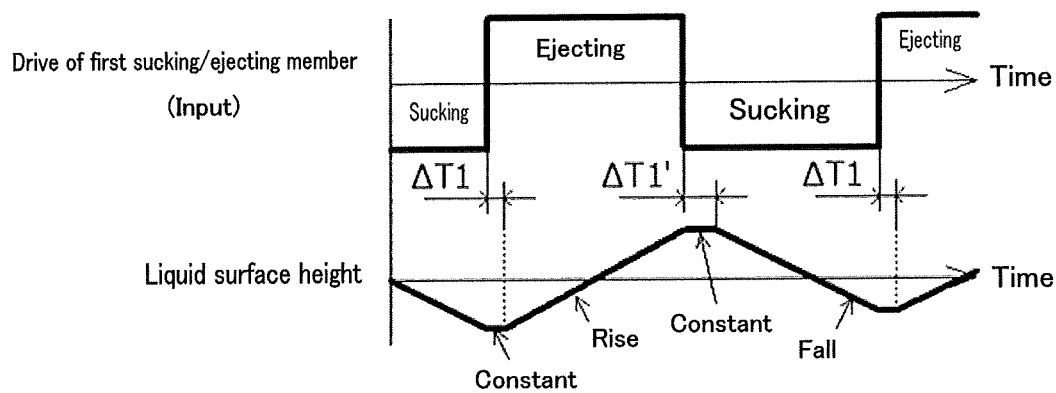
FIG. 38 is a diagram illustrating control information on a sucking/ejecting member and information on liquid surface height sensing in a liquid retaining section when only one of two sucking/ejecting members (the one being a first sucking/ejecting member in this diagram) is driven in a liquid droplet forming device according to an embodiment 4E.
Figure 39:
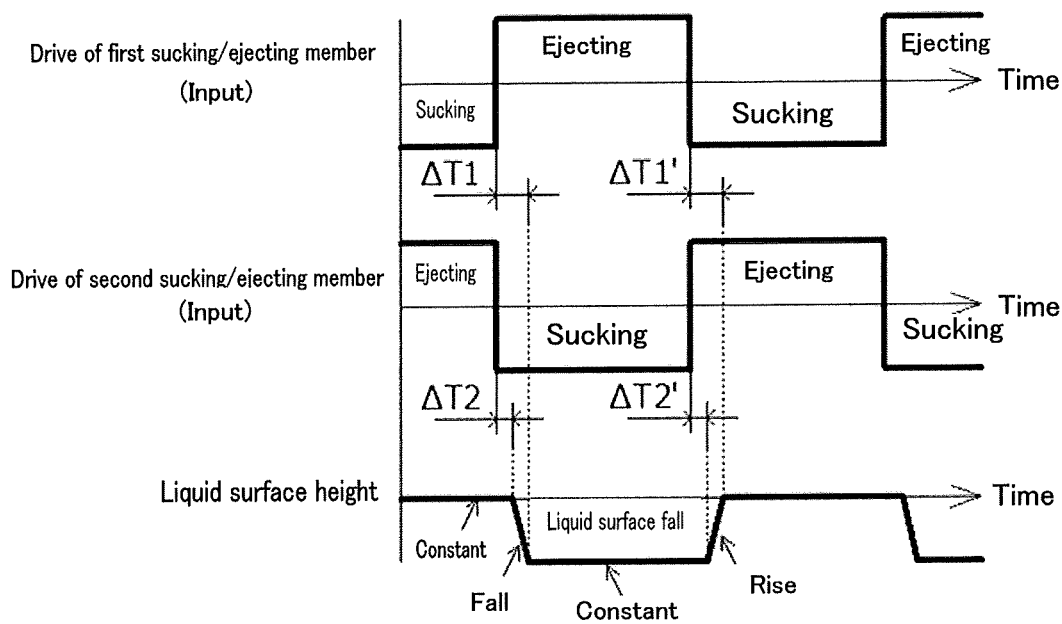
FIG. 39 is a diagram illustrating control information on sucking/ejecting members and information on liquid surface height sensing in a liquid retaining section when both of first and second sucking/ejecting members are driven in a liquid droplet forming device according to an embodiment 4E.

FIG. 37, FIG. 38, and FIG. 39 are diagrams depicting a configuration in which a liquid surface sensing member is disposed in a liquid retaining section as a unit configured to sense a delay time that occurs at the switch of drive between sucking/ejecting operations of a first sucking/ejecting member and a second sucking/ejecting member in a liquid droplet forming device 230 according to an embodiment 4E. Description about the components of the liquid droplet forming device according to the embodiment 4E the same as the components in the embodiments already described will be skipped.

As illustrated in FIG. 37, an image sensor is provided as a liquid surface sensing member capable of constantly detecting liquid surface changes in the liquid retaining section 1.

As the liquid surface sensing member, any other unit than the image sensor, such as a unit based on a light emitting element and a position sensor, and a water detection sensor by a photoelectric sensor may be used.

With reference to FIG. 38 and FIG. 39, a unit configured to detect a delay time due to backlash based on control information on the first and second sucking/ejecting members (drive switching of each sucking/ejecting member) and information on liquid surface height sensing will be described.

FIG. 38 illustrates control information on a sucking/ejecting member and information on liquid surface height sensing in the liquid retaining section when only one of the two sucking/ejecting members (the one being the first sucking/ejecting member in FIG. 38) is driven.

When the sucking/ejecting member is switched in drive between sucking and ejecting, a period of time in which the liquid surface height is constant occurs. In this period of time, the sucking/ejecting member is being unable to perform sucking/ejecting due to backlash. When the sucking/ejecting member completes an operation corresponding to an amount of backlash, the liquid surface height changes.

The difference between the timing at which drive is switched between sucking/ejecting operations based on the control information on the sucking/ejecting member and the timing at which the liquid surface height starts to change is the delay time (ΔT1, ΔT1') of the sucking/ejecting member.

By detecting any delay time of the other sucking/ejecting member in the same manner, it is possible to change control on the sucking/ejecting member (change of the intermittent stop period).

Next, FIG. 39 illustrates control information on sucking/ejecting members and information on liquid surface height sensing in a liquid retaining section when both of first and second sucking/ejecting members are driven.

First, the first sucking/ejecting member is switched in drive from a sucking operation to an ejecting operation. At the same timing, the second sucking/ejecting member is switched in drive from an ejecting operation to a sucking operation. The liquid surface height starts to fall slightly after the timing at which the first and second sucking/ejecting members are switched in drive between sucking/ejection operations, and then becomes constant.

In this case, the difference between the timing at which drive is switched between sucking/ejecting operations based on the control information on the sucking/ejecting members and the timing at which the liquid surface height starts to change is the delay time of the second sucking/ejecting member that is switched in drive from an ejecting operation to a sucking operation.

Further, the difference between the timing at which drive is switched between sucking/ejecting operations based on the control information on the sucking/ejecting members and the timing at which the liquid surface height ceases to change is the delay time of the first sucking/ejecting member that is switched in drive from a sucking operation to an ejecting operation.

Use of this measure enables detection of the delay times of both of the sucking/ejecting members with the simplest configuration (addition of only one delay sensing member) in a short time.

By operating the delay time sensing member described above during an initial operation when the power is turned on, it is possible to obtain information on the delay times of the sucking/ejecting members and change the control on the sucking/ejecting members in a manner to synchronize sucking/ejecting operations, without operations of the user.

Further, by operating the delay time sensing member described above when a predetermined operation time has passed or a sucking or ejecting operation has been performed a predetermined number of times, it is possible to change the control on the sucking/ejecting members in a manner to synchronize sucking/ejecting operations according to information on the latest delay time of the sucking/ejecting members even when the amount of backlash has changed due to, for example, wear of the gears constituting the sucking/ejecting members.

For example, when the liquid amount of the solution 300 in the liquid retaining section 1 is high, when the particle diameter of the particles 350 contained in the solution 300 is large, or when the content concentration is high, the liquid stirring amount or the sucking/ejecting velocity of the first and second sucking/ejecting members 201 and 202 better be high in order to disperse the particles uniformly. On the other hand, when the particles 350 contained are particles that may be damaged by impacts, such as animal cells, the liquid stirring amount or the sucking/ejecting velocity better be as low as possible, and the stirring frequency better be low. Further, as in FIG. 4A and FIG. 4B of the embodiment 2A, the liquid stirring amount or the sucking/ejecting velocity needed varies from the case of re-dispersing the particles from the complete sedimentation state of the particles 350 to the case of suppressing sedimentation of the particles 350 that are in a dispersed state as described above. A higher liquid stirring amount or a higher sucking/ejecting velocity is needed in the former case.

As described above, the liquid stirring amount or the sucking velocity/ejecting velocity needed varies depending on, for example, the amount of the solution 300, the kind or concentration of the particles 350, or the sedimentation state. Therefore, it is preferable that the liquid stirring amount or the sucking/ejecting velocity be switchable.

Embodiment 1F

Figure 40:
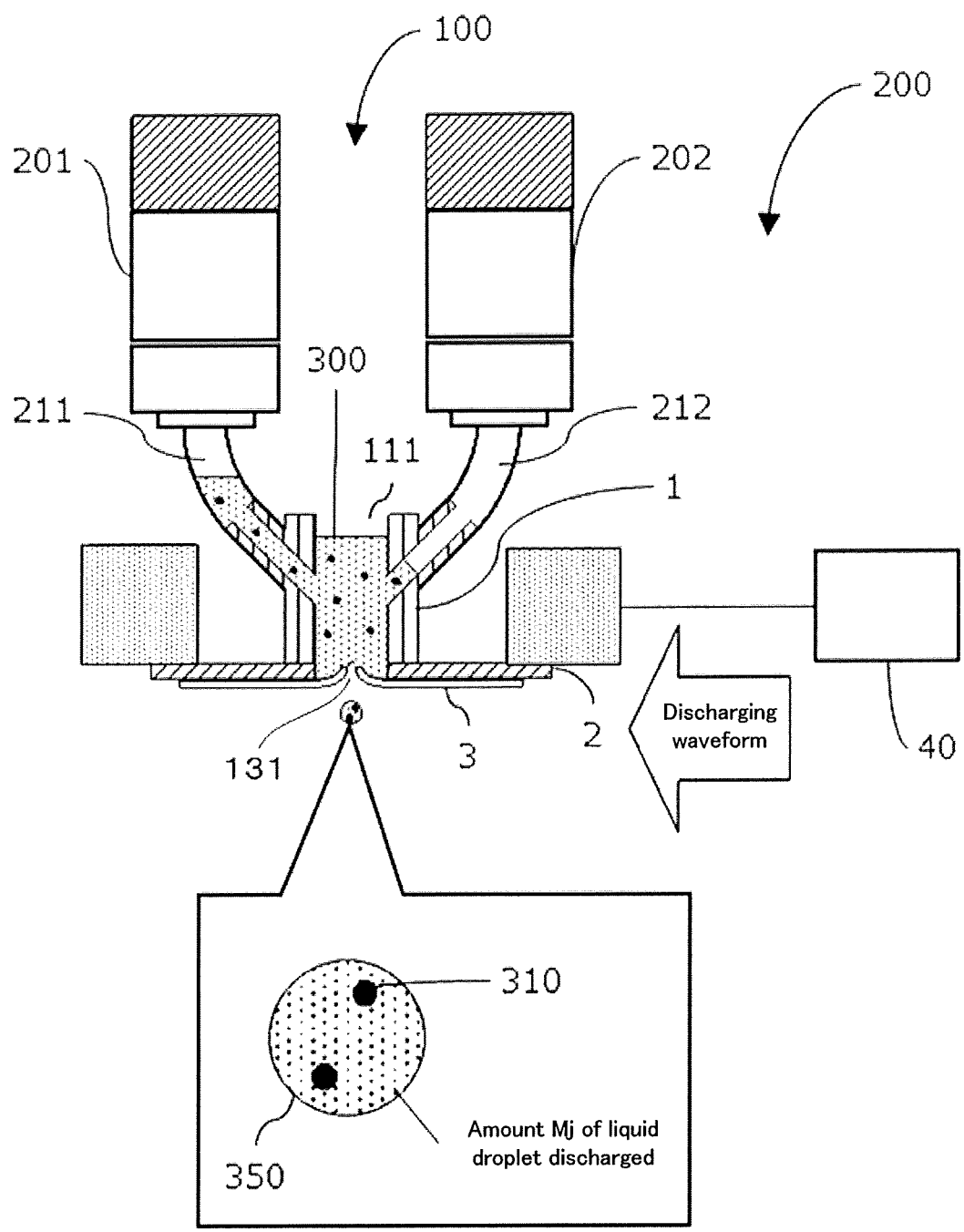
FIG. 40 is a diagram illustrating an example of a liquid droplet forming device according to an embodiment 1F, depicting a specific timing of a sucking/ejecting operation.

FIG. 40 is a diagram depicting liquid amount change in a liquid retaining section during a discharging operation of a liquid droplet forming device 200 according to an embodiment 1F. The liquid droplet forming device 200 according to the embodiment 1F is the same as the liquid droplet forming device 200 according to the embodiment 1A except for the following point. Description about components that are the same as the components already described in the liquid droplet forming device according to the embodiment 1A will be skipped.

As illustrated in FIG. 40, the amount Mj of a liquid droplet discharged, formed by the liquid droplet forming device 200, is determined by the diameter of the nozzle 131.

Figure 41:
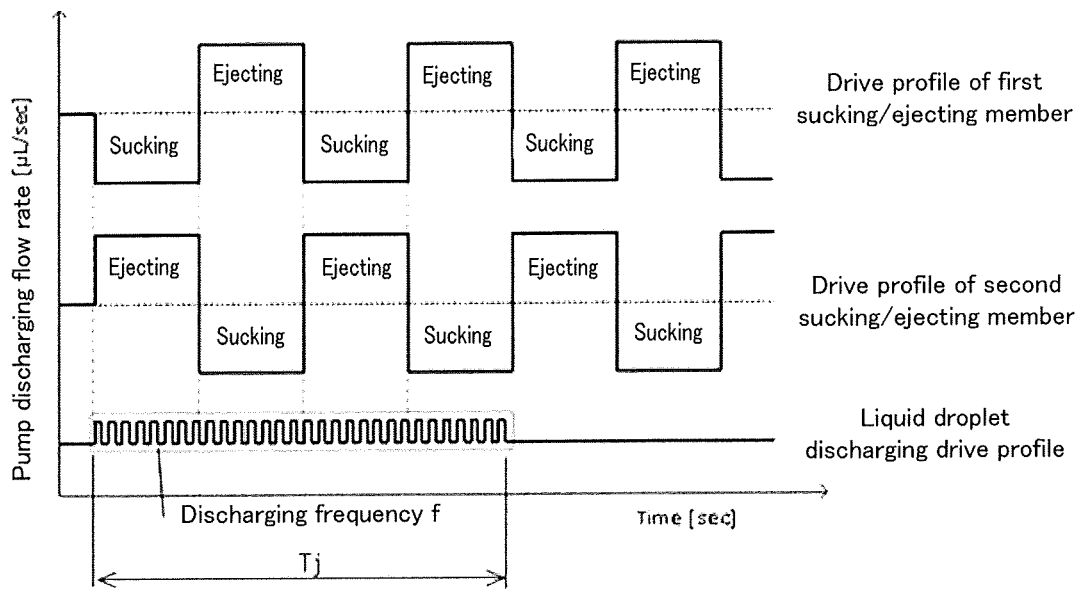
FIG. 41 is a diagram illustrating an example of a liquid droplet forming device according to an embodiment 1F, depicting a cumulative discharge amount to be discharged from a liquid retaining section during a discharging operation.

As illustrated in FIG. 41, the cumulative discharging amount $\Delta S$ to be discharged from the liquid retaining section 1 during a discharging operation is calculated according to $\Delta S = Mj \times f \times Tj = Mj \times Nj$ (Nj: total number of times of discharging), where Tj represents a discharging operation time and f represents a liquid droplet discharging frequency.

When the liquid amount Mj per droplet is low or when the total number of times of discharging Nj is low, $\Delta S$ is low. Therefore, the liquid amount change in the liquid retaining section 1 is low and not significantly influential to discharging. However, when the liquid amount Mj is high or when the total number of times of discharging Nj is high, i.e., when the cumulative discharging amount $\Delta S$ is high, the liquid amount change in the liquid retaining section 1 is high. The amount $\Delta H$ of liquid surface height change when the liquid amount in the liquid retaining section 1 has changed is calculated according to the formula below.

$$\Delta H = \Delta S / A$$

where A represents a sectional area inside the liquid retaining section 1. For example, when the internal shape of the liquid retaining section 1 is a circular cross-sectional shape having a radius r, the sectional area is calculated according to $A = \pi r^2$.

Change $\Delta P$ of the water pressure applied to the upper surface of the nozzle plate 3 when the liquid surface height in the liquid retaining section 1 has changed by $\Delta H$ is calculated according to the formula below.

$$\Delta P = \rho \Delta H$$

where $\rho$ represents the density of the liquid in the liquid retaining section 1.

Along with the change $\Delta P$ of the water pressure applied to the upper surface of the nozzle plate 3, the discharging pressure when the liquid is discharged also changes. As a result, the discharging velocity Vj of a liquid droplet to be discharged changes.

As described above, the change of the discharging velocity Vj is non-problematic in the case of continuously discharging liquid droplets to a single position. However, in the case of patterning liquid droplets at equal intervals by relatively moving the liquid droplet forming device 200 and a landing target (for example, the reference numeral 301 in FIG. 47) to which a dispensing device is configured to land liquid droplets at a constant velocity, the change of the discharging velocity Vj over time also changes the intervals between the liquid droplets landed, resulting in a problem that uniform patterning cannot be realized.

Embodiment 2F

Figure 42A:
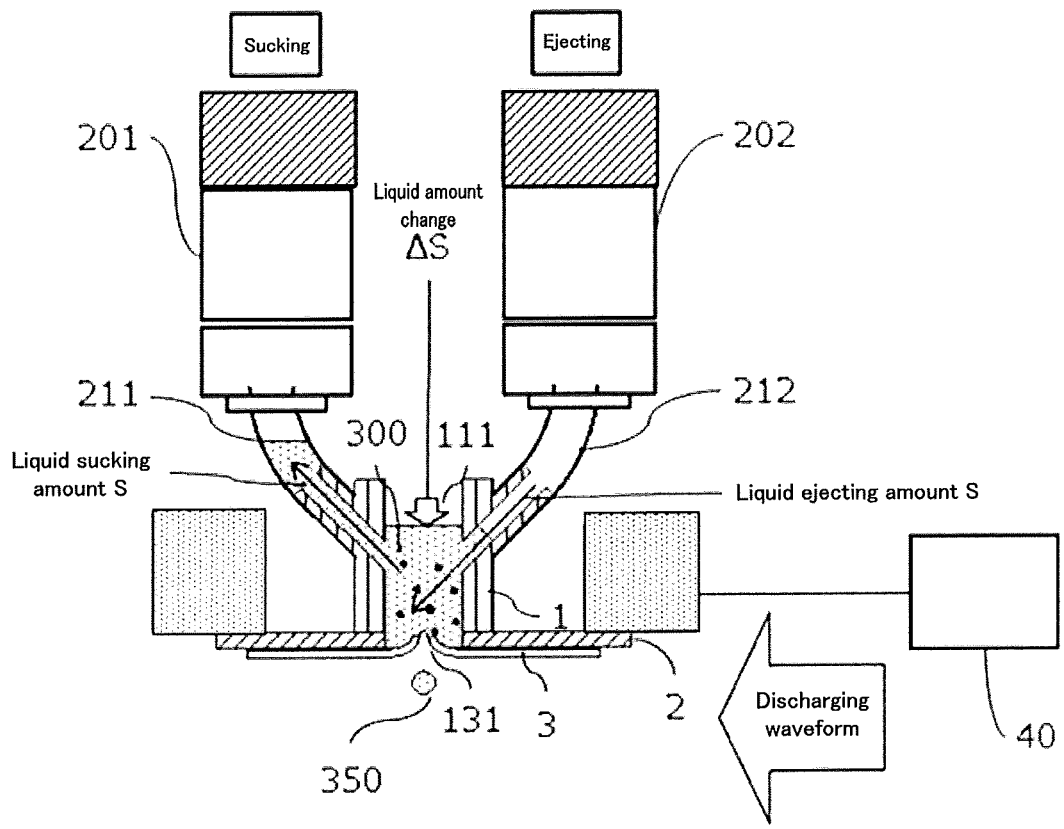
FIG. 42A is a diagram illustrating an example of a liquid droplet forming device according to an embodiment 2F, depicting a specific operation and drive profile of a liquid sending unit for maintaining a liquid surface height during a discharging operation.
Figure 42B:
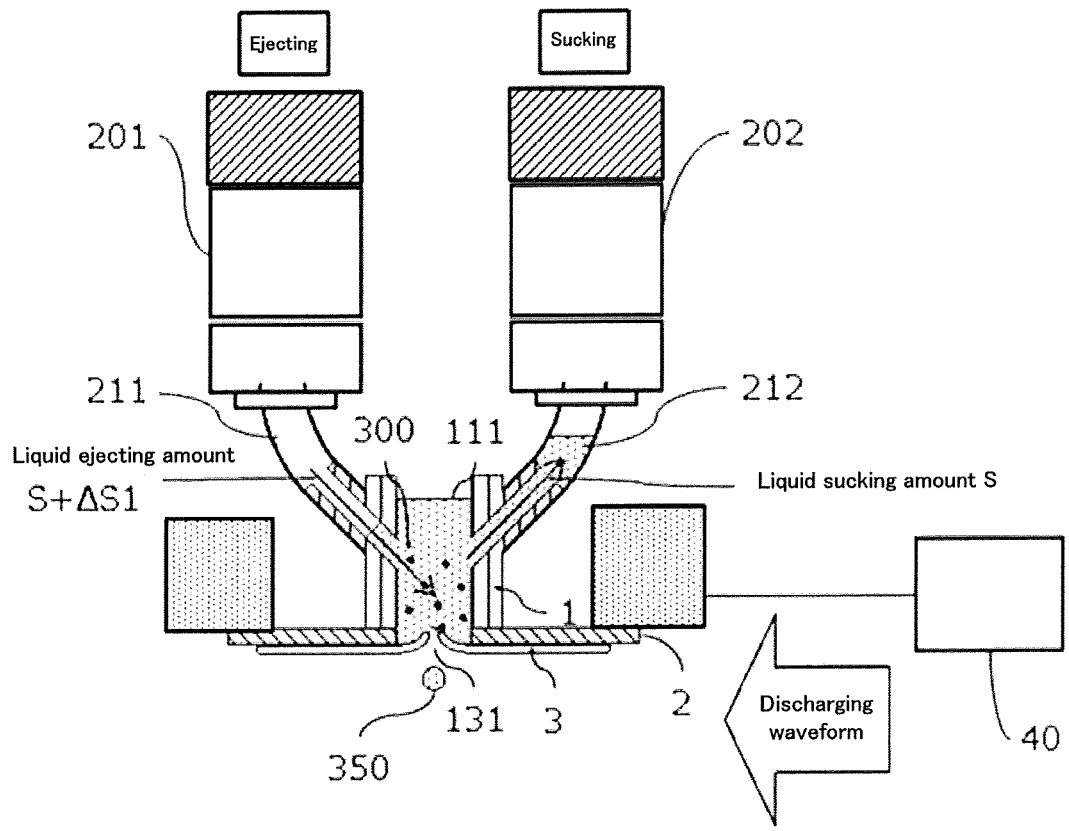
FIG. 42B is a diagram illustrating another example of a liquid droplet forming device according to the embodiment 2F, depicting a specific operation and drive profile of a liquid sending unit for maintaining a liquid surface height during a discharging operation.

FIG. 42A and FIG. 42B are diagrams depicting a specific operation and drive profile of a liquid sending unit for maintaining the liquid surface height during a discharging operation of a liquid droplet forming device 200 according to an embodiment 2F. Description about the components of the liquid droplet forming device according to the embodiment 2F the same as the components in the embodiments already described will be skipped.

Figure 43:
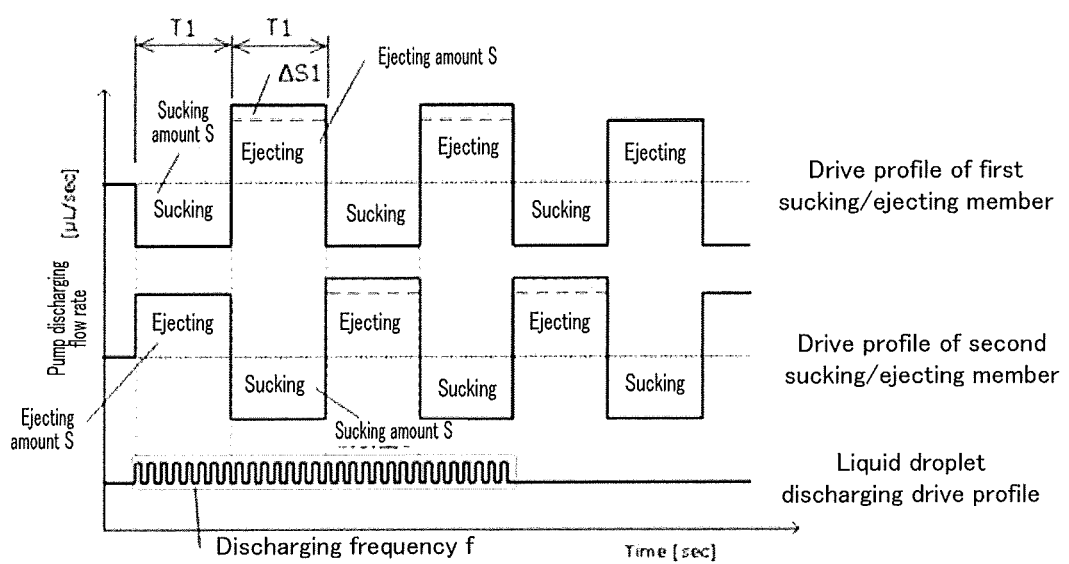
FIG. 43 is a diagram illustrating an example of profiles of discharging operations of first and second sucking/ejecting members of a liquid droplet forming device according to an embodiment 2F.
Figure 44:
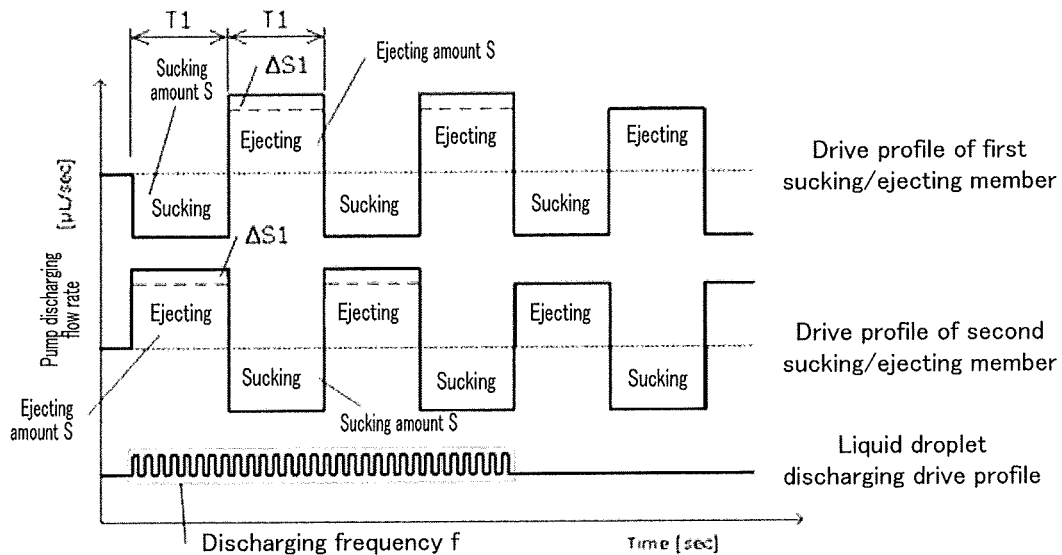
FIG. 44 is a diagram illustrating another example of profiles of discharging operations of first and second sucking/ejecting members of a liquid droplet forming device according to the embodiment 2F.

As illustrated in FIG. 43, the liquid amount $\Delta S1$ to be discharged during one sucking/ejecting operation is $\Delta S1=Mj \times f \times T1$, where T1 represents a time taken for one liquid sucking/ejecting of the first and second sucking/ejecting members 201 and 202. Therefore, as illustrated in FIG. 42A, the liquid surface height in the liquid retaining section 1 falls. Hence, by starting a sucking/ejecting operation of the first and second sucking/ejecting members 201 and 202 in synchronization with the start of the discharging operation illustrated in FIG. 43 and adding, as a correction amount, the liquid amount $\Delta S1$ to be discharged, calculated according to $\Delta S1=Mj \times f \times T1$, to an ejecting amount S in an ejecting operation of the first and second sucking/ejecting members 201 and 202 from the first ejecting operation of the first sucking/ejecting member 201 (the first sucking operation of the second sucking/ejecting member 202), it is possible to replenish an amount of liquid corresponding to the amount $\Delta S1$ discharged. As a result, it is possible to maintain the liquid surface height in the liquid retaining section 1 constant as illustrated in FIG. 42B even during the discharging operation.

After the discharging operation is stopped, by adding the liquid amount $\Delta S1$ to be discharged to the ejecting amount S only in one ejecting operation of the second sucking/ejecting member 202, and afterwards, making the sucking amount and ejecting amount of the first and second sucking/ejecting members 201 and 202 constant at S as illustrated in FIG. 43, it is possible to maintain the liquid surface height.

Alternatively, when the time T1 taken for sucking and ejecting, the discharging frequency f, and the liquid amount Mj to be discharged are known as setting values before the start of operation, by adding the amount $\Delta S1$ described above as a correction value in an ejecting operation of the second sucking/ejecting member 202 simultaneously with the start of discharging, it is possible to maintain the liquid surface constant from the start of discharging until the end of discharging.

Figure 45:
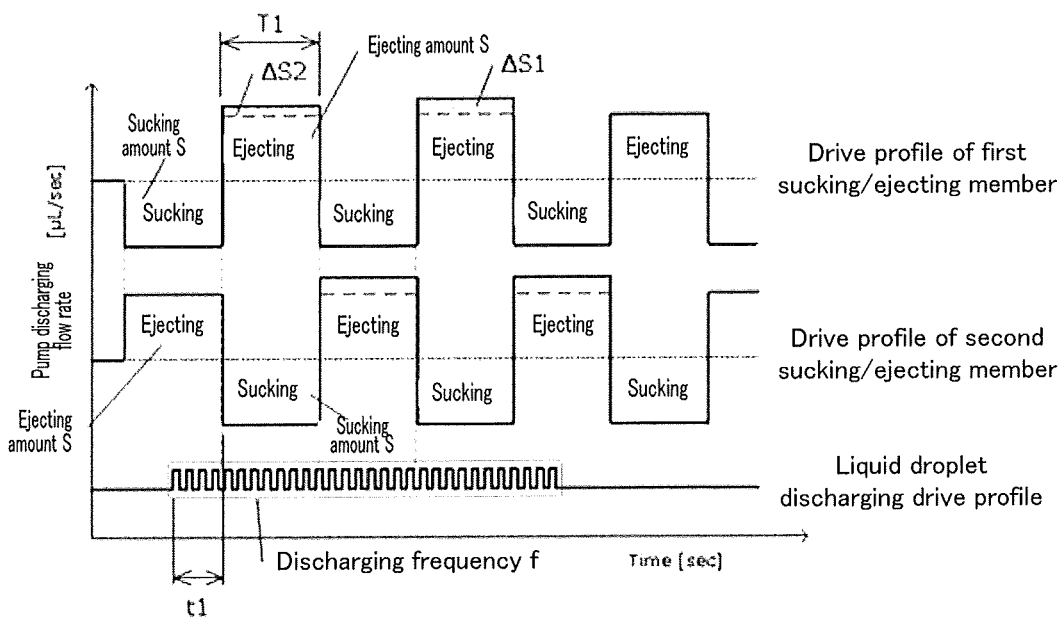
FIG. 45 is a diagram illustrating another example of profiles of discharging operations of first and second sucking/ejecting members of a liquid droplet forming device according to the embodiment 2F.

The operation time T1 of the first and second sucking/ejecting members 201 and 202 may be a preset value. However, in order to maintain the liquid surface height more accurately, a time t1 from the start of discharging until the stop of a sucking operation of the first sucking/ejecting member 201 (until the stop of an ejecting operation of the second sucking/ejecting member 202) may be actually measured by a control unit. By this actual measurement, when the timing at which discharging is started fails in coinciding with the timing at which the operation of the liquid sending unit is started as illustrated in FIG. 45, it is possible to calculate $\Delta S2=Mj \times f \times t1$, using the time t1 from the start of discharging until the stop of the liquid sending unit. Alternatively, by counting the number N1 of times of discharging performed from the start of discharging until the stop of a sucking operation of the first sucking/ejecting member 201 (until the stop of an ejecting operation of the second sucking/ejecting member 202), it is possible to calculate $\Delta S2=Mj \times N1$.

By adding $\Delta S2$ calculated based on t1 or N1 as a correction amount to the ejecting amount S in the next ejecting operation of the first sucking/ejecting member 201, it is possible to maintain the liquid surface height in the liquid retaining section 1 constant when the discharging operation is performed intermittently.

Embodiment 3F

Figure 46:
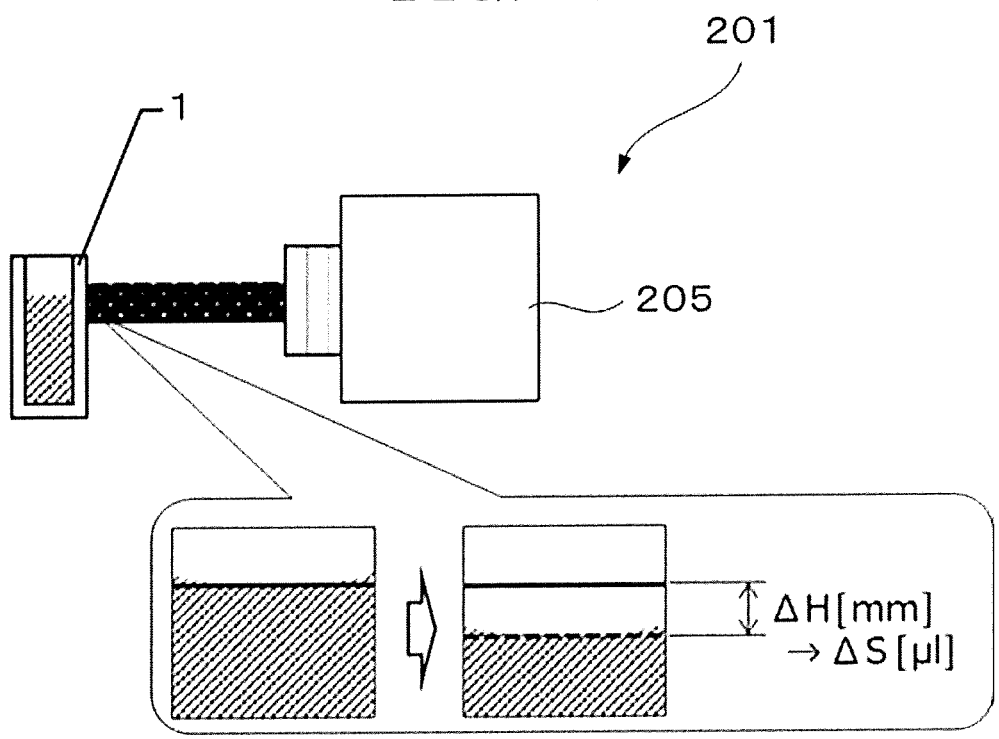
FIG. 46 is a diagram illustrating a liquid droplet forming device according to an embodiment 3F, depicting a case of detecting a change of a liquid surface height with a sensor.

FIG. 46 is a diagram depicting a case of detecting a change of the liquid surface height with a sensor in a liquid droplet forming device 201 according to an embodiment 3F. Description about the components of the liquid droplet forming device according to the embodiment 3F the same as the components in the embodiments already described will be skipped.

FIG. 46 illustrates a case where the liquid surface height in the liquid retaining section 1 of the liquid droplet forming device 201 is captured with a camera 205 and an amount $\Delta H$ of liquid surface height change is calculated by image processing. An amount $\Delta S$ of liquid amount change in the liquid retaining section 1 can be calculated according to the formula below based on the amount $\Delta H$ of liquid surface height change.

$$\Delta S = \Delta H \times A$$

where A represents a sectional area inside the liquid retaining section 1. For example, when the internal shape of the liquid retaining section 1 is a circular cross-sectional shape having a radius r, the sectional area is calculated according to $A=\pi r^2$.

By adding $\Delta S$ calculated according to the calculation formula above as $\Delta S1$ of FIG. 45 to the ejecting amount S of the first and second sucking/ejecting members 201 and 202 as a correction value, it is possible to maintain the liquid surface height constant not only when the liquid amount has changed by discharging but also when, for example, the liquid amount has changed by volatilization.

The unit configured to detect the liquid surface height in the liquid retaining section 1 is not limited to the camera 205 described above. The liquid surface height may be measured with, for example, a capacitance-type liquid amount detecting sensor, or by liquid surface height sensing with a laser displacement sensor provided above in the case of an opaque liquid.

Embodiments of a dispensing device used in the present disclosure will be described in detail with reference to the drawings.

Embodiment 1 of Dispensing Device

Figure 47:
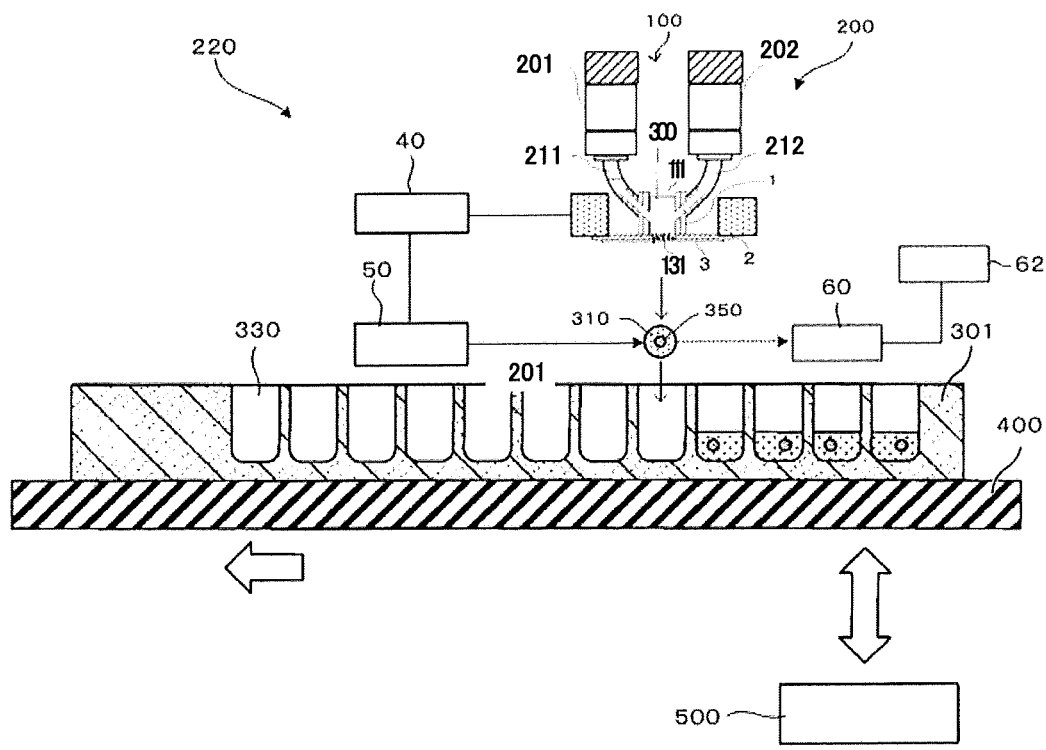
FIG. 47 is a schematic diagram illustrating an example of a dispensing device used in the present disclosure.

FIG. 47 is a schematic diagram illustrating an example of a dispensing device according to an embodiment 1. In the dispensing device according to the embodiment 1, the liquid droplet forming device of the present disclosure is used as a dispensing device configured to dispense particles into concaves of a landing target. Description about the components of the dispensing device according to the embodiment 1 the same as the components in the embodiments already described will be skipped. Such components will be denoted by the same reference numerals.

A dispensing device 220 illustrated in FIG. 47 includes a liquid droplet forming device 200, a landing target 301, a stage 400, and a control unit 500.

As the liquid droplet forming device 200, the liquid droplet forming device 200 according to the embodiment 1A illustrated in FIG. 2 is used.

Instead of the liquid droplet forming device 200, any of the liquid droplet forming devices 200A to 200C according to the embodiment 1A illustrated in FIG. 9, FIG. 13, and FIG. 14 may be used.

The landing target 301 is disposed on the stage 400 that is movable. A plurality of concaves (wells) 330 into which liquid droplets 310 discharged by the liquid droplet discharging unit 100 of the liquid droplet forming device 200 land are formed in the landing target 301.

The control unit 500 is configured to move the stage 400 and control a relative positional relationship between the liquid droplet discharging unit 100 of the liquid droplet forming device 200 and each concave 330. This enables the liquid droplet discharging unit 100 of the liquid droplet forming device 200 to discharge liquid droplets 310 containing particles 350 into each concave 330 sequentially.

The control unit 500 may include, for example, a CPU, a ROM, and a RAM. In this case, various functions of the control unit 500 can be realized by programs recorded in, for example, the ROM being read out into the main memory and executed by the CPU. However, a part or the whole of the control unit 500 may be realized only by hardware. The control unit 500 may be configured by, for example, a plurality of devices physically.

Figure 48:
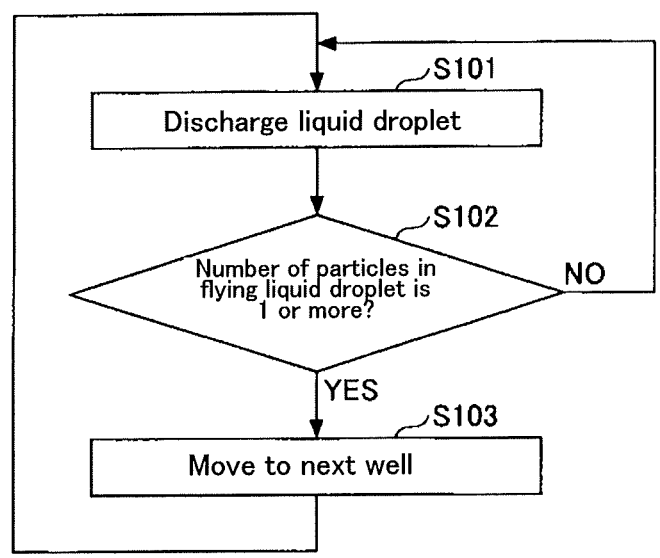
FIG. 48 is a flowchart illustrating an example of an operation of a dispensing device.

FIG. 48 is an example of a flowchart illustrating an operation of the dispensing device according to the embodiment 1. In the step S101, the liquid droplet discharging unit 100 of the liquid droplet forming device 200 discharges a liquid droplet 310 into a predetermined concave 330.

In the step S102, a particle number counting unit 62 of the liquid droplet forming device 200 senses the number of particles 350 contained in the flying liquid droplet 310, and sends the sensing result to the control unit 500. When the sensing result of the particle number counting unit 62 is not "1 or more" (i.e., the sensing result is zero), the operation of the step S101 is repeated.

When the sensing result of the particle number counting unit 62 is "1 or more" in the step S102, the flow moves to the step S103. In the step S103, the control unit 500 controls the stage 400 to move the landing target 301 to a position at which the liquid droplet discharging unit 100 of the liquid droplet forming device 200 and the next concave 330 face each other. Subsequently, the flow moves to the step S101 to repeat the same operation.

Hence, when the number of particles 350 contained in a liquid droplet 310 flying toward a concave 330 is zero, a liquid droplet 310 is discharged toward the same concave 330 again. Therefore, particles 350 can be dispensed into the plurality of concaves 330 without fail.

Instead of presence or absence of particles 350 in a flying liquid droplet 310, the number of particles 350 contained in a flying liquid droplet 310 may be sensed as illustrated in FIG. 19.

Figure 49:
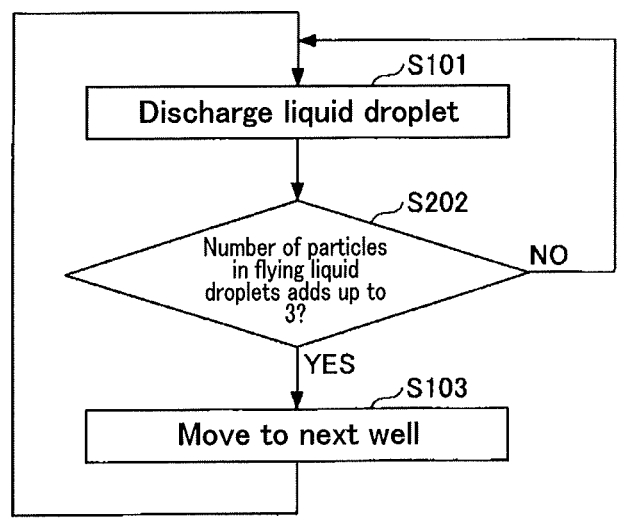
FIG. 49 is a flowchart illustrating another example of an operation of a dispensing device.

FIG. 49 is another example of a flowchart illustrating the operation of the dispensing device according to the embodiment 1.

In FIG. 49, in the step S202 after the step 101 which is the same as in FIG. 48 is performed, the particle number counting unit 62 of the liquid droplet forming device 200 senses the number of particles 350 contained in a flying liquid droplet 310 and sends the sensing result to the control unit 500. Until when the sensing result of the particle number counting unit 62 adds up to "3 particles", the operation of the step S101 is repeated.

When the number of particles 350 contained in a liquid droplet 310 is high, the sensing accuracy of the particle number counting unit 62 may be poor. Therefore, there is no indispensable need for setting the number of particles 350 to be contained in a liquid droplet 310 discharged each time to 3 particles. For example, it is possible to set the number of particles 350 to be contained in a liquid droplet 310 discharged each time to 0 particles or 1 particle. In this case, the operation of the step S101 is repeated until when the total number of particles 350 contained in liquid droplets 310 becomes 3 particles.

When the sensing result of the particle number counting unit 62 is "3 particles" in the step S202, the flow moves to the step S103. The step S103 which the same as in FIG. 48 is performed. Subsequently, the flow moves to the step S101 to repeat the same operation. This makes it possible to perform dispensing in a manner that the number of particles 350 in each concave 330 becomes 3 particles.

In the processes of FIG. 48 and FIG. 49, the function of moving the liquid droplet forming device 200 to a predetermined position along the stage 400 may be incorporated into, for example, the control unit 500 as a program.

Preferred embodiments have been described in detail above. However, the embodiments described above are non-limiting. For example, an embodiment in which the number of liquid sucking/ejecting members and the number of tubes disposed in communication with the liquid retaining section are 3 or more may be included. Various modifications and substitutions may be made to the embodiments described above without departing from the scope of the claims.

The embodiment A is as follows, for example.

<1> A liquid droplet discharging unit including:
a liquid droplet discharging port;
a liquid retaining section including the liquid droplet discharging port;
two tubes disposed in communication with the liquid retaining section; and
first and second liquid sucking/ejecting members coupled to the two tubes respectively,
wherein while the first liquid sucking/ejecting member is in a sucking or ejecting state, the second liquid sucking/ejecting member is in a non-sucking or non-ejecting state correspondingly.

<2> The liquid droplet discharging unit according to <1>, wherein the two tubes are disposed to be inclined with respect to the liquid droplet discharging port.

<3> The liquid droplet discharging unit according to <1> or <2>, including:
a nozzle plate in which the liquid droplet discharging port is provided; and
a vibration member configured to vibrate the nozzle plate to discharge a liquid droplet through the liquid droplet discharging port.

<4> The liquid droplet discharging unit according to any one of <1> to <3>,
wherein the two tubes are disposed symmetrically with respect to a center axis passing through the liquid droplet discharging port.

<5> The liquid droplet discharging unit according to any one of <1> to <4>,
wherein center axes of the two tubes are not on a same plane.

<6> The liquid droplet discharging unit according to any one of <1> to <5>,
wherein in synchronization with a liquid sucking operation of any one liquid sucking/ejecting member of the first and second liquid sucking/ejecting members, the other liquid sucking/ejecting member performs a liquid ejecting operation.
<7> The liquid droplet discharging unit according to any one of <1> to <6>,
wherein the first liquid sucking/ejecting member and the second liquid sucking/ejecting member are switchable to a plurality of liquid sending velocities.
<8> The liquid droplet discharging unit according to any one of <1> to <7>,
wherein the first liquid sucking/ejecting member and the second liquid sucking/ejecting member are switchable to a plurality of liquid sending amounts.
<9> The liquid droplet discharging unit according to any one of <3> to <8>,
wherein a surface of the liquid retaining section facing the nozzle plate is atmospherically exposed.
<10> A liquid droplet forming device including
the liquid droplet discharging unit according to any one of <1> to <9>.
<11> The liquid droplet forming device according to <10>, including
a particle number counting unit configured to count a number of particles contained in a liquid droplet.
<12> A stirring device including:
a liquid retaining section configured to retain a liquid;
two tubes disposed in communication with the liquid retaining section; and
first and second liquid sucking/ejecting members coupled to the two tubes respectively,
wherein while the first liquid sucking/ejecting member is in a sucking or ejecting state, the second liquid sucking/ejecting member is in a non-sucking or non-ejecting state correspondingly.

The embodiment B is as follows, for example.
<1> A liquid discharging unit including:
a liquid droplet discharging port;
a liquid retaining section including the liquid droplet discharging port;
first and second liquid sucking/ejecting members configured to suck and eject a liquid in the liquid retaining section;
a first tube linking the liquid retaining section and the first liquid sucking/ejecting member to each other; and
a second tube linking the liquid retaining section and the second liquid sucking/ejecting member to each other,
wherein maximum liquid sucking amounts of the first and second liquid sucking/ejecting members are lower than volumes of the first tube and the second tube respectively.
<2> The liquid droplet discharging unit according to <1>, including
a nozzle plate in which the liquid droplet discharging port is provided; and
a vibration member configured to vibrate the nozzle plate to discharge a liquid droplet through the liquid droplet discharging port.
<3> The liquid droplet discharging unit according to <1> or <2>,
wherein the first tube and the second tube are replaceable.
<4> The liquid droplet discharging unit according to any one of <1> to <3>,
wherein the volume of the first tube and the volume of the second tube are changeable.

<5> The liquid droplet discharging unit according to any one of <1> to <4>,
wherein while the first liquid sucking/ejecting member is in a sucking or ejecting state, the second liquid sucking/ejecting member is in a non-sucking or non-ejecting state correspondingly.
<6> The liquid droplet discharging unit according to any one of <1> to <5>,
wherein in synchronization with a liquid sucking operation of any one liquid sucking/ejecting member of the first liquid sucking/ejecting member and the second liquid sucking/ejecting member, the other liquid sucking/ejecting member performs a liquid ejecting operation.
<7> The liquid droplet discharging unit according to any one of <1> to <6>,
wherein the first liquid sucking/ejecting member and the second liquid sucking/ejecting member are switchable to a plurality of liquid sending velocities.
<8> The liquid droplet discharging unit according to any one of <1> to <7>,
wherein the first liquid sucking/ejecting member and the second liquid sucking/ejecting member are switchable to a plurality of liquid sending amounts.
<9> The liquid droplet discharging unit according to any one of <2> to <8>,
wherein a surface of the liquid retaining section facing the nozzle plate is atmospherically exposed.
<10> A liquid droplet forming device including
the liquid droplet discharging unit according to any one of <1> to <9>.
<11> The liquid droplet forming device according to <10>, including
a particle number counting unit configured to count a number of particles contained in a liquid droplet.
<12> A stirring device including:
a liquid retaining section configured to retain a liquid;
first and second liquid sucking/ejecting members configured to suck and eject the liquid in the liquid retaining section;
a first tube linking the liquid retaining section and the first liquid sucking/ejecting member to each other; and
a second tube linking the liquid retaining section and the second liquid sucking/ejecting member to each other,
wherein maximum liquid sucking amounts of the first and second liquid sucking/ejecting members are lower than volumes of the first tube and the second tube respectively.

The embodiment C is as follows, for example.
<1> A liquid droplet discharging unit including:
a discharging port;
a liquid retaining section including the discharging port; and
a sucking/ejecting member configured to suck and eject a liquid in the liquid retaining section,
wherein the liquid droplet discharging unit is configured to perform sucking/ejecting operations while varying an ejecting velocity of the sucking/ejecting member.
<2> The liquid droplet discharging unit according to <1>, including;
a nozzle plate in which the discharging port is provided; and
a vibration member configured to vibrate the nozzle plate to discharge a liquid droplet through the discharging port.
<3> The liquid droplet discharging unit according to <1> or <2>,
wherein the sucking/ejecting member includes at least first and second sucking/ejecting members,
wherein while the first sucking/ejecting member is in a sucking or ejecting state, the second sucking/ejecting member is in a non-sucking or non-ejecting state correspondingly, and wherein the liquid droplet discharging unit is configured to perform sucking/ejecting operations repeatedly in a first sucking or ejecting mode and a second sucking or ejecting mode in which the ejecting velocity is lower than in the first sucking or ejecting mode.

<4> The liquid droplet discharging unit according to <3>, wherein operation of the first ejecting mode and operation of the second ejecting mode are continuous.

<5> The liquid droplet discharging unit according to <3> or <4>, wherein operation of the first ejecting mode and operation of the second ejecting mode are continuous, and wherein operation of the first sucking mode is continuous from operation of the second ejecting mode.

<6> The liquid droplet discharging unit according to any one of <3> to <5>, wherein a time of the first ejecting mode is shorter than a time of the second ejecting mode.

<7> The liquid droplet discharging unit according to <1> or <2>, wherein the sucking/ejecting member includes at least first and second sucking/ejecting members, wherein while the first sucking/ejecting member is in a sucking or ejecting state, the second sucking/ejecting member is in a non-sucking or non-ejecting state correspondingly, and wherein the ejecting velocity is lower at an end of sucking/ejecting than at a start of sucking or ejecting.

<8> The liquid droplet discharging unit according to <7>, wherein an ejecting operation and a next sucking operation are continuous.

<9> The liquid droplet discharging unit according to any one of <1> to <8>, including a sensing member configured to sense a dispersion state of particles in the liquid retaining section, wherein the liquid droplet discharging unit is configured to determine the ejecting velocity in the first ejecting mode and the ejecting velocity in the second ejecting mode depending on the dispersion state of particles.

<10> The liquid droplet discharging unit according to any one of <1> to <8>, including a sensing member configured to sense a dispersion state of particles in the liquid retaining section, wherein the liquid droplet discharging unit is configured to determine an ejecting time of the first ejecting mode and an ejecting time of the second ejecting mode depending on the dispersion state of particles.

<11> The liquid droplet discharging unit according to any one of <1> to <10>, including a sensing member configured to sense a dispersion state of particles in the liquid retaining section, wherein the liquid droplet discharging unit is configured to determine the ejecting velocity at a start of sucking or ejecting depending on the dispersion state of particles.

<12> The liquid droplet discharging unit according to any one of <1> to <11>, including a sensing member configured to sense a dispersion state of particles in a liquid retaining section, wherein the liquid droplet discharging unit is configured to determine a slope between the ejecting velocity at a start of sucking or ejecting and the ejecting velocity at an end of sucking or ejecting depending on the dispersion state of particles.

<13> The liquid droplet discharging unit according to any one of <1> to <12>, including a sensing range restricting member configured to restrict a range in which the dispersion state of particles in the liquid retaining section is sensed.

<14> A liquid droplet forming device including the liquid droplet discharging unit according to any one of <1> to <13>.

<15> A stirring device including:
a liquid retaining section configured to retain a liquid; and
a sucking/ejecting member configured to suck and eject the liquid in the liquid retaining section,
wherein the stirring device is configured to perform sucking/ejecting operations while varying an ejecting velocity of the sucking/ejecting member.

<16> A dispensing device including the liquid droplet forming device according <14>.

The embodiment D is as follows, for example.

<1> A liquid droplet discharging unit including:
a discharging port;
a liquid retaining section including the discharging port;
first and second sucking/ejecting members configured to suck and eject a liquid in the liquid retaining section;
a first flow path linking the liquid retaining section and the first sucking/ejecting member to each other;
a second flow path linking the liquid retaining section and the second sucking/ejecting member to each other;
a sucking/ejecting control unit configured to control a sucking operation and an ejecting operation of the first and second sucking/ejecting members; and
a liquid surface detecting member configured to detect a position of a liquid surface in the liquid retaining section.

<2> The liquid droplet discharging unit according to <1>, including;
a nozzle plate in which the discharging port is provided; and
a vibration member configured to vibrate the nozzle plate to discharge a liquid droplet through the discharging port.

<3> The liquid droplet discharging unit according to <1> or <2>, wherein the liquid droplet discharging unit is configured to control switching between an ejecting operation and a sucking operation of the first and second sucking/ejecting members based on a liquid surface height change detection result of the liquid surface detecting member.

<4> The liquid droplet discharging unit according to any one of <1> to <3>, wherein when the liquid surface detecting member senses that a height of the liquid surface has risen above a prescribed value, the liquid droplet discharging unit is configured to bring any one sucking/ejecting member, which performs an ejecting operation, of the first and second sucking/ejecting members to operation termination first, and after the height of the liquid surface has returned to within a range of the prescribed value according to the liquid surface detecting member, bring the other sucking/ejecting member, which performs a sucking operation, to operation termination.

<5> The liquid droplet discharging unit according to any one of <1> to <3>, wherein the liquid surface detecting member senses that a height of the liquid surface has risen above a prescribed value, the liquid droplet discharging unit is configured to set any one sucking/ejecting member, which performs a sucking operation, of the first and second sucking/ejecting members at a sucking velocity that is higher than an ejecting velocity of the other sucking/ejecting member, which performs an ejecting operation.

<6> The liquid droplet discharging unit according to any one of <1> to <5>,
wherein in a next sucking/ejecting operation after an operation control according to <4> or <5> is performed, the liquid droplet discharging unit is configured to start a sucking operation of any one sucking/ejecting member, which performs a sucking operation, of the first and second sucking/ejecting members earlier than a start of an ejecting operation of the other sucking/ejecting member, which performs an ejecting operation, by a difference between times at which the operation terminations of the first and second sucking/ejecting members according to <4> occur.

<7> The liquid droplet discharging unit according to any one of <1> to <3>,
wherein when the liquid surface detecting member senses that a height of the liquid surface has fallen below a prescribed value, the liquid droplet discharging unit is configured to bring any one sucking/ejecting member, which performs a sucking operation, of the first and second sucking/ejecting members to operation termination first, and after the height of the liquid surface has returned to within a range of the prescribed value according to the liquid surface detecting member, bring the other sucking/ejecting member, which performs an ejecting operation, to operation termination.

<8> The liquid droplet discharging unit according to any one of <1> to <3>,
wherein when the liquid surface detecting member senses that a height of the liquid surface has fallen below a prescribed value, the liquid droplet discharging unit is configured to set any one sucking/ejecting member, which performs a sucking operation, of the first and second sucking/ejecting members at an ejecting velocity that is higher than an ejecting velocity of the other sucking/ejecting member, which performs a sucking operation.

<9> The liquid droplet discharging unit according to any one of <1> to <3>, <7>, and <8>,
wherein in a next sucking/ejecting operation after an operation control according to <7> or <8> is performed, the liquid droplet discharging unit is configured to start an ejecting operation of any one sucking/ejecting member, which performs an ejecting operation, of the first and second sucking/ejecting members earlier than a start of a sucking operation of the other sucking/ejecting member, which performs a sucking operation, by a difference between times at which the operation terminations of the first and second sucking/ejecting members according to <7> occur.

<10> The liquid droplet discharging unit according to any one of <1> to <9>,
wherein the first and second sucking/ejecting members are switchable to a plurality of liquid sending velocities.

<11> The liquid droplet discharging unit according to any one of <1> to <10>,
wherein the first and second sucking/ejecting members are switchable to a plurality of liquid sending amounts.

<12> The liquid droplet discharging unit according to any one of <2> to <11>,
wherein a surface of the liquid retaining section facing the nozzle plate is atmospherically exposed.

<13> A liquid droplet forming device including the liquid droplet discharging unit according to any one of <1> to <12>.

<14> The liquid droplet forming device according to <13>, including an input unit configured to input a prescribed value of a height of the liquid surface in the liquid retaining section,
wherein the prescribed value of the height of the liquid surface is at least any one of an upper limit value and a lower limit value.

<15> The liquid droplet forming device according to <13> or <14>, including
an output unit configured to output a detection result of the liquid surface detecting member,
wherein a height of the liquid surface is digitally displayable on an operation unit.

<16> The liquid droplet forming device according to <13> or <14>, including
an output unit configured to output a detection result of the liquid surface detecting member,
wherein when a height of the liquid surface has shifted from a prescribed value, the shift is displayable by luminescence.

<17> The liquid droplet forming device according to any one of <13> to <16>, including
a particle number counting unit configured to count a number of particles contained in a liquid droplet.

<18> A stirring device including:
a liquid retaining section configured to retain a liquid;
first and second sucking/ejecting members configured to suck and eject the liquid in the liquid retaining section;
a first flow path linking the liquid retaining section and the first sucking/ejecting member to each other;
a second flow path linking the liquid retaining section and the second sucking/ejecting member to each other;
a sucking/ejecting control unit configured to control a sucking operation and an ejecting operation of the first and second sucking/ejecting members; and
a liquid surface detecting member configured to detect a position of a liquid surface in the liquid retaining section.

<19> A dispensing device including the liquid droplet forming device according to any one of <13> to <17>.

The embodiment E is as follows, for example.
<1> A liquid droplet discharging unit including:
a discharging port;
a liquid retaining section including the discharging port;
first and second sucking/ejecting members configured to suck and eject a liquid in the liquid retaining section;
a first flow path linking the liquid retaining section and the first sucking/ejecting member to each other;
a second flow path linking the liquid retaining section and the second sucking/ejecting member to each other; and
a sucking/ejecting control unit configured to control a sucking operation and an ejecting operation of the first and second sucking/ejecting members,
wherein the liquid droplet discharging unit is configured to drive the first sucking/ejecting member to perform sucking/ejecting operations continuously, drive the second sucking/ejecting member to perform sucking/ejecting operations intermittently, and vary an intermittent stop period of the second sucking/ejecting member according to information on a delay time from when each sucking/ejecting member starts to be driven to perform sucking/ejecting operations until when sucking/ejecting operations start.

<2> A liquid droplet discharging unit including:
a discharging port;
a liquid retaining section including the discharging port;
first and second sucking/ejecting members configured to suck and eject a liquid in the liquid retaining section;
a first flow path linking the liquid retaining section and the first sucking/ejecting member to each other;
a second flow path linking the liquid retaining section and the second sucking/ejecting member to each other; and a sucking/ejecting control unit configured to control a sucking operation and an ejecting operation of the first and second sucking/ejecting members, wherein the liquid droplet discharging unit is configured to drive the first and second sucking/ejecting members to perform sucking/ejecting operations intermittently, and vary intermittent stop periods of the first and second sucking/ejecting members according to information on a delay time from when each sucking/ejecting member starts to be driven to perform sucking/ejecting operations until when sucking/ejecting operations start.

<3> The liquid droplet discharging unit according to <1> or <2>, including:

a nozzle plate in which the discharging port is provided; and
a vibration member configured to vibrate the nozzle plate to discharge a liquid droplet through the discharging port.

<4> The liquid droplet discharging unit according to any one of <1> to <3>, including a delay sensing member configured to sense the information on a delay time from when the first and second sucking/ejecting members start to be driven to perform sucking/ejecting operations until when sucking/ejecting operations start.

<5> The liquid droplet discharging unit according to <4>, wherein the delay sensing member is configured to sense start of plunger movement of the first and second sucking/ejecting members.

<6> The liquid droplet discharging unit according to <4>, wherein the delay sensing member is configured to sense a height of a liquid surface in the liquid retaining section.

<7> The liquid droplet discharging unit according to any one of <4> to <6>, wherein the delay sensing member is operated when power is turned on.

<8> The liquid droplet discharging unit according to any one of <4> to <6>, wherein the delay sensing member is operated when a predetermined operation time has passed.

<9> The liquid droplet discharging unit according to any one of <4> to <6>, wherein the delay sensing member is operated when a number of times a sucking or ejecting operation is performed has passed a predetermined number of times.

<10> The liquid droplet discharging unit according to any one of <3> to <9>, wherein a surface of the liquid retaining section facing the nozzle plate is atmospherically exposed.

<11> A liquid droplet forming device including
the liquid droplet discharging unit according to any one of <1> to <10>.

<12> A stirring device including:
a liquid retaining section configured to retain a liquid;
first and second sucking/ejecting members configured to suck and eject the liquid in the liquid retaining section;
a first flow path linking the liquid retaining section and the first sucking/ejecting member to each other;
a second flow path linking the liquid retaining section and the second sucking/ejecting member to each other; and
a sucking/ejecting control unit configured to control a sucking operation and an ejecting operation of the first and second sucking/ejecting members, wherein the stirring device is configured to drive the first sucking/ejecting member to perform sucking/ejecting operations continuously, drive the second sucking/ejecting member to perform sucking/ejecting operations intermittently, and vary an intermittent stop period of the second sucking/ejecting member according to information on a delay time from when each sucking/ejecting member starts to be driven to perform sucking/ejecting operations until when sucking/ejecting operations start.

<13> A stirring device including:
a liquid retaining section configured to retain a liquid;
first and second sucking/ejecting members configured to suck and eject the liquid in the liquid retaining section;
a first flow path linking the liquid retaining section and the first sucking/ejecting member to each other;
a second flow path linking the liquid retaining section and the second sucking/ejecting member to each other; and
a sucking/ejecting control unit configured to control a sucking operation and an ejecting operation of the first and second sucking/ejecting members, wherein the stirring device is configured to drive the first and second sucking/ejecting members to perform sucking/ejecting operations intermittently, and vary intermittent stop periods of the first and second sucking/ejecting members according to information on a delay time from when each sucking/ejecting member starts to be driven to perform sucking/ejecting operations until when sucking/ejecting operations start.

<14> A dispensing device including
the liquid droplet forming device according to <11>.

The embodiment F is as follows, for example.

<1> A liquid droplet discharging unit including:
a discharging port;
a liquid retaining section including the discharging port;
first and second sucking/ejecting members configured to suck and eject a liquid in the liquid retaining section;
a first flow path linking the liquid retaining section and the first sucking/ejecting member to each other;
a second flow path linking the liquid retaining section and the second sucking/ejecting member to each other; and
a correcting unit configured to determine a correcting amount by which an ejecting amount of any one sucking/ejecting member of the first and second sucking/ejecting members is corrected relative to a sucking amount of the other sucking/ejecting member, wherein the liquid droplet discharging unit is configured to set the ejecting amount of the any one sucking/ejecting member of the first and second sucking/ejecting members higher by the correcting amount than the sucking amount of the other sucking/ejecting member.

<2> The liquid droplet discharging unit according to <1>,
wherein while the first liquid sucking/ejecting member is in a sucking or ejecting state, the second liquid sucking/ejecting member is in a non-sucking or non-ejecting state correspondingly.

<3> The liquid droplet discharging unit according to <1> or <2>, including:
a nozzle plate in which the discharging port is provided; and
a vibration member configured to vibrate the nozzle plate to discharge a liquid droplet through the discharging port.

<4> The liquid droplet discharging unit according to any one of <1> to <3>,
wherein a liquid sucking operation of any one of the first and second sucking/ejecting members is performed during a discharging operation of the liquid droplet discharging unit.

<5> The liquid droplet discharging unit according to any one of <1> to <4>,
wherein a liquid in a predetermined amount is previously held in the first flow path and the second flow path.

<6> The liquid droplet discharging unit according to any one of <1> to <5>,
wherein the correcting amount of the correcting unit is determined based on any one of a liquid amount to be discharged, a discharging frequency, and a time taken by the first and second sucking/ejecting members to perform sucking or ejecting.
<7> The liquid droplet discharging unit according to any one of <1> to <6>, including
a liquid amount detecting member configured to detect a liquid amount in the liquid retaining section.
<8> The liquid droplet discharging unit according to <7>, wherein the correcting amount of the correcting unit is determined based on an amount of change in the liquid amount in the liquid retaining section detected by the liquid amount detecting member.
<9> The liquid droplet discharging unit according to <7> or <8>,
wherein the liquid amount detecting member is a sensor configured to count a number of liquid droplets discharged.
<10> The liquid droplet discharging unit according to <7> or <8>,
wherein the liquid amount detecting member is a sensor configured to capture an image of a liquid surface in the liquid retaining section and detect a position of the liquid surface by image processing.
<11> The liquid droplet discharging unit according to any one of <1> to <10>,
wherein in synchronization with a sucking operation of any one sucking/ejecting member of the first and second sucking/ejecting members, the other sucking/ejecting member performs an ejecting operation.
<12> A liquid droplet forming device including
the liquid droplet discharging unit according to any one of <1> to <11>.
<13> The liquid droplet forming device according to <12>, including
a particle number counting unit configured to count a number of particles contained in a liquid droplet.
<14> A stirring device including:
a liquid retaining section configured to retain a liquid;
first and second sucking/ejecting members configured to suck and eject the liquid in the liquid retaining section;
a first flow path linking the liquid retaining section and the first sucking/ejecting member to each other;
a second flow path linking the liquid retaining section and the second sucking/ejecting member to each other; and
a correcting unit configured to determine a correcting amount by which an ejecting amount of any one sucking/ejecting member of the first and second sucking/ejecting members is corrected relative to a sucking amount of the other sucking/ejecting member,
wherein the ejecting amount of the any one sucking/ejecting member of the first and second sucking/ejecting members is set higher by the correcting amount than the sucking amount of the other sucking/ejecting member.
<15> A dispensing device including
the liquid droplet forming device according to <12> or <13>.

What is claimed is:
1. A liquid droplet discharging unit comprising:
a liquid droplet discharging port;
a nozzle plate in which the liquid droplet discharging port is provided;
a liquid retaining section that comprises the liquid droplet discharging port;
two tubes disposed in communication with the liquid retaining section; and
first and second liquid sucking/ejecting members coupled to the two tubes respectively,
wherein while the first liquid sucking/ejecting member is in a sucking or ejecting state, the second liquid sucking/ejecting member is in a non-sucking or non-ejecting state correspondingly, and
wherein a surface of the liquid retaining section facing the nozzle plate is atmospherically exposed.
2. The liquid droplet discharging unit according to claim 1,
wherein the two tubes are disposed to be inclined with respect to the liquid droplet discharging port.
3. The liquid droplet discharging unit according to claim 1, comprising:
a vibration member configured to vibrate the nozzle plate to discharge a liquid droplet through the liquid droplet discharging port.
4. The liquid droplet discharging unit according to claim 1,
wherein the two tubes are disposed symmetrically with respect to a center axis passing through the liquid droplet discharging port.
5. The liquid droplet discharging unit according to claim 1,
wherein center axes of the two tubes are not on a same plane.
6. The liquid droplet discharging unit according to claim 1,
wherein in synchronization with a liquid sucking operation of any one liquid sucking/ejecting member of the first and second liquid sucking/ejecting members, other liquid sucking/ejecting member performs a liquid ejecting operation.
7. The liquid droplet discharging unit according to claim 1,
wherein the first liquid sucking/ejecting member and the second liquid sucking/ejecting member are switchable to a plurality of liquid sending velocities.
8. The liquid droplet discharging unit according to claim 1,
wherein the first liquid sucking/ejecting member and the second liquid sucking/ejecting member are switchable to a plurality of liquid sending amounts.
9. A liquid droplet forming device comprising
a liquid droplet discharging unit that comprises:
a liquid droplet discharging port;
a nozzle plate in which the liquid droplet discharging port is provided;
a liquid retaining section that comprises the liquid droplet discharging port;
two tubes disposed in communication with the liquid retaining section; and
first and second liquid sucking/ejecting members coupled to the two tubes respectively,
wherein while the first liquid sucking/ejecting member is in a sucking or ejecting state, the second liquid sucking/ejecting member is in a non-sucking or non-ejecting state correspondingly, and
wherein a surface of the liquid retaining section facing the nozzle plate is atmospherically exposed.
10. The liquid droplet forming device according to claim 9, comprising
a particle number counting unit configured to count a number of particles contained in a liquid droplet.
11. The liquid droplet discharging unit according to claim 9,
wherein the two tubes are disposed to be inclined with respect to the liquid droplet discharging port.

12. The liquid droplet discharging unit according to claim 9, comprising:
a vibration member configured to vibrate the nozzle plate to discharge a liquid droplet through the liquid droplet discharging port.

13. The liquid droplet discharging unit according to claim 9,
wherein the two tubes are disposed symmetrically with respect to a center axis passing through the liquid droplet discharging port.

14. The liquid droplet discharging unit according to claim 9,
wherein center axes of the two tubes are not on a same plane.

15. The liquid droplet discharging unit according to claim 9,
wherein in synchronization with a liquid sucking operation of any one liquid sucking/ejecting member of the first and second liquid sucking/ejecting members, other liquid sucking/ejecting member performs a liquid ejecting operation.

16. The liquid droplet discharging unit according to claim 9,
wherein the first liquid sucking/ejecting member and the second liquid sucking/ejecting member are switchable to a plurality of liquid sending velocities.

17. The liquid droplet discharging unit according to claim 9,
wherein the first liquid sucking/ejecting member and the second liquid sucking/ejecting member are switchable to a plurality of liquid sending amounts.

18. A stirring device comprising:
a liquid retaining section configured to retain a liquid;
a nozzle plate in which the liquid droplet discharging port is provided;
two tubes disposed in communication with the liquid retaining section; and
first and second liquid sucking/ejecting members coupled to the two tubes respectively,
wherein while the first liquid sucking/ejecting member is in a sucking or ejecting state, the second liquid sucking/ejecting member is in a non-sucking or non-ejecting state correspondingly, and
wherein a surface of the liquid retaining section facing the nozzle plate is atmospherically exposed.

* * * * *